US010578474B2

(12) United States Patent
Ruchti et al.

(10) Patent No.: US 10,578,474 B2
(45) **Date of Patent: *Mar. 3, 2020**

(54) AIR DETECTION SYSTEM AND METHOD FOR DETECTING AIR IN A PUMP OF AN INFUSION SYSTEM

(71) Applicant: ICU Medical, Inc., San Clemente, CA (US)

(72) Inventors: Timothy L. Ruchti, Gurnee, IL (US); Brian G. Markey, Park Forest, IL (US); Anatoly S. Belkin, Glenview, IL (US); Paul T. Kotnik, Commerce Township, MI (US); Mohammad M. Khair, Streamwood, IL (US)

(73) Assignee: ICU Medical, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/001,680

(22) Filed: Jun. 6, 2018

(65) Prior Publication Data

US 2019/0101425 A1 Apr. 4, 2019

Related U.S. Application Data

(63) Continuation of application No. 13/851,207, filed on Mar. 27, 2013, now Pat. No. 9,995,611.

(Continued)

(51) Int. Cl.

*G01F 1/74* (2006.01)
*F04B 51/00* (2006.01)

(Continued)

(52) U.S. Cl.

CPC .......... *G01F 1/74* (2013.01); *A61M 5/16831* (2013.01); *A61M 5/365* (2013.01);

(Continued)

(58) Field of Classification Search

None

See application file for complete search history.

(56) References Cited

U.S. PATENT DOCUMENTS

| | | | |
|---|---|---|---|
| 3,401,337 | A | 9/1968 | Beusman et al. |
| 3,484,681 | A | 12/1969 | Grady, Jr. et al. |

(Continued)

FOREIGN PATENT DOCUMENTS

| | | |
|---|---|---|
| BR | PI0704229-9 | 11/2009 |
| DE | 31 12 762 | 1/1983 |

(Continued)

OTHER PUBLICATIONS

Alaedeen et al., "Total Parenteral Nutrition-Associated Hyperglycemia Correlates with Prolonged Mechanical Ventilation and Hospital Stay in Septic Infants", Journal of Pediatric Surgery, Jan. 2006, vol. 41, No. 1, pp. 239-244.

(Continued)

*Primary Examiner* — Lina M Cordero

(74) *Attorney, Agent, or Firm* — Knobbe Martens Olson & Bear, LLP

(57) ABSTRACT

Various systems and methods for detecting air in a chamber of an infusion system are disclosed. In one embodiment, a determination is made that air is contained in the chamber on the basis of a change in the average force exerted against the plunger utilizing a derivative spike for event detection and a systematic reduction in the average force to confirm the nature of the change. In another embodiment, a determination is made that the chamber contains air when a difference between the current force profile and a baseline force profile crosses a threshold. In an additional embodiment, a force profile is classified as being an air force profile or a liquid force profile based on extracted features of the force profile.

16 Claims, 19 Drawing Sheets

Related U.S. Application Data

(60) Provisional application No. 61/618,129, filed on Mar. 30, 2012.

(51) Int. Cl.
*F04B 43/00* (2006.01)
*A61M 5/36* (2006.01)
*A61M 5/168* (2006.01)

(52) U.S. Cl.
CPC .......... *F04B 43/0081* (2013.01); *F04B 51/00* (2013.01); *A61M 2205/331* (2013.01)

(56) References Cited

U.S. PATENT DOCUMENTS 3,699,320 A 10/1972 Zimmerman et al.
3,727,074 A 4/1973 Keller et al.
3,731,679 A 5/1973 Wilhelmson et al.
3,768,084 A 10/1973 Haynes
3,770,354 A 11/1973 Tsuruta et al.
3,778,702 A 12/1973 Finger
3,806,821 A 4/1974 Niemeyer et al.
3,838,565 A 10/1974 Carlyle
3,854,038 A 12/1974 McKinley
3,886,459 A 5/1975 Hufford et al.
3,890,554 A 6/1975 Yoshitake et al.
3,898,637 A 8/1975 Wolstenholme
3,901,231 A 8/1975 Olson
3,909,693 A 9/1975 Yoshitake et al.
3,910,701 A 10/1975 Henderson
3,911,343 A 10/1975 Oster
3,919,608 A 11/1975 Usami et al.
3,921,622 A 11/1975 Cole
3,930,404 A 1/1976 Ryden, Jr.
3,933,431 A 1/1976 Trujillo et al.
3,935,876 A 2/1976 Massie et al.
3,944,963 A 3/1976 Hively
3,966,358 A 6/1976 Heimes et al.
3,971,980 A 7/1976 Jungfer et al.
3,974,681 A 8/1976 Namery
3,974,683 A 8/1976 Martin
3,985,467 A 10/1976 Lefferson
3,990,444 A 11/1976 Vial
3,997,888 A 12/1976 Kremer
4,005,724 A 2/1977 Courtot
4,014,206 A 3/1977 Taylor
4,038,982 A 8/1977 Burke
4,039,269 A 8/1977 Pickering
4,048,474 A 9/1977 Olesen
4,049,954 A 9/1977 Da Costa Vieira et al.
4,055,175 A 10/1977 Clemens et al.
4,068,521 A 1/1978 Cosentino et al.
4,078,562 A 3/1978 Friedman
4,089,227 A 5/1978 Falgari et al.
4,094,318 A 6/1978 Burke
4,105,028 A 8/1978 Sadlier et al.
4,114,144 A 9/1978 Hyman
4,151,845 A 5/1979 Clemens
4,155,362 A 5/1979 Jess
4,173,224 A 11/1979 Marx
4,181,610 A 1/1980 Shintani et al.
4,183,244 A 1/1980 Kohno et al.
4,195,515 A 4/1980 Smoll
4,210,138 A 7/1980 Jess et al.
4,213,454 A 7/1980 Shim
4,217,993 A 8/1980 Jess et al.
4,240,294 A 12/1980 Grande
4,240,438 A 12/1980 Updike et al.
4,244,365 A 1/1981 McGill
4,256,437 A 3/1981 Brown
4,261,356 A 4/1981 Turner et al.
4,264,861 A 4/1981 Radu et al.
4,265,240 A 5/1981 Jenkins
4,270,532 A 6/1981 Franetzki et al.
4,277,226 A 7/1981 Archibald et al.
4,278,085 A 7/1981 Shim
4,280,495 A 7/1981 Lampert
4,282,872 A 8/1981 Franetzki et al.
4,286,202 A 8/1981 Clancy et al.
4,290,346 A 9/1981 Bujan
4,291,692 A 9/1981 Bowman et al.
4,292,405 A 9/1981 Mascoli
4,298,357 A 11/1981 Permic
4,308,866 A 1/1982 Jeliffe
4,312,341 A 1/1982 Zissimopoulos
4,319,568 A 3/1982 Tregoning
4,322,201 A 3/1982 Archibald
4,323,849 A 4/1982 Smith
4,324,662 A 4/1982 Schnell
4,328,800 A 5/1982 Marx
4,328,801 A 5/1982 Marx
4,333,045 A 6/1982 Oltendorf
4,343,316 A 8/1982 Jespersen
4,344,429 A 8/1982 Gupton et al.
4,346,707 A 8/1982 Whitney et al.
4,360,019 A 11/1982 Portner et al.
4,366,384 A 12/1982 Jensen
4,367,736 A 1/1983 Gupton
4,370,983 A 2/1983 Lichtenstein et al.
4,373,527 A 2/1983 Fischell
4,379,452 A 4/1983 DeVries
4,381,005 A 4/1983 Bujan
4,384,578 A 5/1983 Winkler
4,385,247 A 5/1983 Satomi
4,391,598 A 7/1983 Thompson
4,392,849 A 7/1983 Petre et al.
4,394,862 A 7/1983 Shim
4,395,259 A 7/1983 Prestele et al.
4,397,194 A 8/1983 Soltz
4,399,362 A 8/1983 Cormier et al.
4,407,659 A 10/1983 Adam
4,411,651 A 10/1983 Schulman
4,418,565 A 12/1983 St. John
4,432,699 A 2/1984 Beckman et al.
4,432,761 A 2/1984 Dawe
4,432,762 A 2/1984 Dawe
4,443,218 A 4/1984 Decant, Jr. et al.
4,444,546 A 4/1984 Pazemenas
4,447,191 A 5/1984 Bilstad et al.
4,447,224 A 5/1984 Decant, Jr. et al.
4,453,931 A 6/1984 Pastrone
4,457,751 A 7/1984 Rodler
4,463,301 A 7/1984 Moriguchi et al.
4,464,170 A 8/1984 Clemens
4,467,654 A 8/1984 Murakami et al.
4,468,222 A 8/1984 Lundquist
4,468,601 A 8/1984 Chamran et al.
4,469,481 A 9/1984 Kobayashi
4,475,666 A 10/1984 Bilbrey et al.
4,475,901 A 10/1984 Kraegen et al.
4,477,756 A 10/1984 Moriguchi
4,479,760 A 10/1984 Bilstad et al.
4,480,218 A 10/1984 Hair
4,483,202 A 11/1984 Ogua et al.
4,487,601 A 12/1984 Lindemann
4,492,909 A 1/1985 Hartwig
4,496,346 A 1/1985 Mosteller
4,498,843 A 2/1985 Schneider et al.
4,501,531 A 2/1985 Bilstad et al.
4,504,263 A 3/1985 Steuer
4,507,112 A 3/1985 Hillel
4,510,266 A 4/1985 Eertink
4,515,584 A 5/1985 Abe et al.
4,519,792 A 5/1985 Dawe
4,521,212 A 6/1985 Ruschke
4,525,163 A 6/1985 Slavik et al.
4,526,568 A 7/1985 Clemens et al.
4,526,574 A 7/1985 Pekkarinen
4,529,401 A 7/1985 Leslie et al.
4,533,350 A 8/1985 Danby et al.
4,543,955 A 10/1985 Schroeppel
4,551,134 A 11/1985 Slavik et al.
4,553,958 A 11/1985 LeCocq
4,559,036 A 12/1985 Wunsch

(56) References Cited

U.S. PATENT DOCUMENTS

| | | | |
|---|---|---|---|
| 4,559,037 | A | 12/1985 | Franetzki et al. |
| 4,559,044 | A | 12/1985 | Robinson |
| 4,559,454 | A | 12/1985 | Kramer |
| 4,565,500 | A | 1/1986 | Jeensalaute et al. |
| 4,583,981 | A | 4/1986 | Urquhart et al. |
| 4,587,473 | A | 5/1986 | Turvey |
| 4,607,520 | A | 8/1986 | Dam |
| 4,617,014 | A | 10/1986 | Cannon et al. |
| 4,624,661 | A | 11/1986 | Arimond |
| 4,627,835 | A | 12/1986 | Fenton, Jr. |
| 4,633,878 | A | 1/1987 | Bombardieri |
| 4,634,426 | A | 1/1987 | Kamen |
| 4,634,427 | A | 1/1987 | Hannula et al. |
| 4,636,144 | A | 1/1987 | Abe et al. |
| 4,637,813 | A | 1/1987 | DeVries |
| 4,645,489 | A | 2/1987 | Krumme |
| 4,648,869 | A | 3/1987 | Bobo, Jr. |
| 4,652,260 | A | 3/1987 | Fenton, Jr. et al. |
| 4,658,244 | A | 4/1987 | Meijer |
| 4,668,216 | A | 5/1987 | Martin |
| 4,668,945 | A | 5/1987 | Aldrovandi et al. |
| 4,673,334 | A | 6/1987 | Allington et al. |
| 4,673,389 | A | 6/1987 | Archibald et al. |
| 4,676,776 | A | 6/1987 | Howson et al. |
| 4,677,359 | A | 6/1987 | Enami et al. |
| 4,678,979 | A | 7/1987 | Hori |
| 4,678,998 | A | 7/1987 | Muramatsu |
| 4,679,562 | A | 7/1987 | Luksha |
| 4,683,428 | A | 7/1987 | Gete |
| 4,685,903 | A | 8/1987 | Cable et al. |
| 4,690,673 | A | 9/1987 | Bloomquist |
| 4,691,153 | A | 9/1987 | Nishimura |
| 4,692,145 | A | 9/1987 | Weyant |
| 4,696,671 | A | 9/1987 | Epstein et al. |
| 4,697,129 | A | 9/1987 | Enami et al. |
| 4,702,675 | A | 10/1987 | Aldrovandi et al. |
| 4,705,506 | A | 11/1987 | Archibald et al. |
| 4,710,106 | A | 12/1987 | Iwata et al. |
| 4,714,462 | A | 12/1987 | DiDomenico |
| 4,714,463 | A | 12/1987 | Archibald et al. |
| 4,718,576 | A | 1/1988 | Tamura et al. |
| 4,720,636 | A | 1/1988 | Benner |
| 4,722,224 | A | 2/1988 | Scheller et al. |
| 4,722,734 | A | 2/1988 | Kolin |
| 4,731,051 | A | 3/1988 | Fischell |
| 4,731,057 | A | 3/1988 | Tanaka et al. |
| 4,737,711 | A | 4/1988 | O'Hare |
| 4,739,346 | A | 4/1988 | Buckley |
| 4,741,732 | A | 5/1988 | Crankshaw et al. |
| 4,741,736 | A | 5/1988 | Brown |
| 4,748,857 | A | 6/1988 | Nakagawa |
| 4,751,445 | A | 6/1988 | Sakai |
| 4,756,706 | A | 7/1988 | Kerns et al. |
| 4,758,228 | A | 7/1988 | Williams |
| 4,763,525 | A | 8/1988 | Cobb |
| 4,764,166 | A | 8/1988 | Spani et al. |
| 4,764,697 | A | 8/1988 | Christiaens |
| 4,776,842 | A | 10/1988 | Franetzki et al. |
| 4,781,687 | A | 11/1988 | Wall |
| 4,784,576 | A | 11/1988 | Bloom et al. |
| 4,785,184 | A | 11/1988 | Bien et al. |
| 4,785,799 | A | 11/1988 | Schoon et al. |
| 4,785,969 | A | 11/1988 | McLaughlin |
| 4,786,800 | A | 11/1988 | Kamen |
| 4,789,014 | A | 12/1988 | DiGianfilippo |
| 4,797,655 | A | 1/1989 | Orndal et al. |
| 4,803,389 | A | 2/1989 | Ogawa et al. |
| 4,803,625 | A | 2/1989 | Fu et al. |
| 4,818,186 | A | 4/1989 | Pastrone et al. |
| 4,820,281 | A | 4/1989 | Lawler |
| 4,821,558 | A | 4/1989 | Pastrone et al. |
| 4,828,545 | A | 5/1989 | Epstein et al. |
| 4,828,693 | A | 5/1989 | Lindsay |
| 4,829,448 | A | 5/1989 | Balding et al. |
| 4,838,856 | A | 6/1989 | Mulreany et al. |
| 4,838,857 | A | 6/1989 | Strowe et al. |
| 4,840,542 | A | 6/1989 | Abbott |
| 4,842,584 | A | 6/1989 | Pastrone et al. |
| 4,845,487 | A | 7/1989 | Frantz et al. |
| 4,846,792 | A | 7/1989 | Bobo et al. |
| 4,850,805 | A | 7/1989 | Madsen et al. |
| 4,851,755 | A | 7/1989 | Fincher |
| 4,854,324 | A | 8/1989 | Hirschman et al. |
| 4,856,339 | A | 8/1989 | Williams |
| 4,857,048 | A | 8/1989 | Simons et al. |
| 4,857,050 | A | 8/1989 | Lentz et al. |
| 4,858,154 | A | 8/1989 | Anderson et al. |
| 4,863,425 | A | 9/1989 | Slate et al. |
| 4,865,584 | A | 9/1989 | Epstein et al. |
| 4,869,722 | A | 9/1989 | Heyman |
| 4,874,359 | A | 10/1989 | White et al. |
| 4,881,413 | A | 11/1989 | Georgi et al. |
| 4,882,575 | A | 11/1989 | Kawahara |
| 4,884,013 | A | 11/1989 | Jackson et al. |
| 4,884,065 | A | 11/1989 | Crouse et al. |
| 4,886,422 | A | 12/1989 | Takeuchi et al. |
| 4,898,576 | A | 2/1990 | Philip |
| 4,898,578 | A | 2/1990 | Rubalcaba, Jr. |
| 4,906,103 | A | 3/1990 | Kao |
| 4,908,017 | A | 3/1990 | Howson et al. |
| 4,910,475 | A | 3/1990 | Lin |
| 4,919,595 | A | 4/1990 | Likuski et al. |
| 4,919,596 | A | 4/1990 | Slate et al. |
| 4,925,444 | A | 5/1990 | Orkin et al. |
| 4,927,411 | A | 5/1990 | Pastrone et al. |
| 4,930,358 | A | 6/1990 | Motegi et al. |
| 4,936,820 | A | 6/1990 | Dennehey |
| 4,936,828 | A | 6/1990 | Chiang |
| 4,938,079 | A | 7/1990 | Goldberg |
| 4,943,279 | A | 7/1990 | Samiotes et al. |
| 4,946,439 | A | 8/1990 | Eggers |
| 4,947,856 | A | 8/1990 | Beard |
| 4,950,235 | A | 8/1990 | Slate et al. |
| 4,950,244 | A | 8/1990 | Fellingham |
| 4,959,050 | A | 9/1990 | Bobo, Jr. |
| 4,966,579 | A | 10/1990 | Polaschegg |
| 4,968,941 | A | 11/1990 | Rogers |
| 4,972,842 | A | 11/1990 | Korten et al. |
| 4,976,687 | A | 12/1990 | Martin |
| 4,978,335 | A | 12/1990 | Arthur, III |
| 4,979,940 | A | 12/1990 | Lapp et al. |
| 4,981,467 | A | 1/1991 | Bobo et al. |
| 5,000,663 | A | 3/1991 | Gorton |
| 5,000,739 | A | 3/1991 | Kulisz et al. |
| 5,006,050 | A | 4/1991 | Cooke et al. |
| 5,010,473 | A | 4/1991 | Jacobs |
| 5,014,714 | A | 5/1991 | Millay et al. |
| 5,018,945 | A | 5/1991 | D'Silva |
| 5,026,348 | A | 6/1991 | Venegas |
| 5,028,857 | A | 7/1991 | Taghezout |
| 5,032,112 | A | 7/1991 | Fairchild et al. |
| 5,034,004 | A | 7/1991 | Crankshaw |
| 5,035,143 | A | 7/1991 | Latimer et al. |
| 5,041,086 | A | 8/1991 | Koenig et al. |
| 5,043,706 | A | 8/1991 | Oliver |
| 5,045,069 | A | 9/1991 | Imparato |
| 5,049,047 | A | 9/1991 | Polaschegg et al. |
| 5,052,230 | A | 10/1991 | Lang |
| 5,053,747 | A | 10/1991 | Slate et al. |
| 5,055,761 | A | 10/1991 | Mills |
| 5,056,992 | A | 10/1991 | Simons |
| 5,058,161 | A | 10/1991 | Weiss |
| 5,059,171 | A | 10/1991 | Bridge |
| 5,063,603 | A | 11/1991 | Burt |
| 5,064,412 | A | 11/1991 | Henke et al. |
| 5,078,683 | A | 1/1992 | Sancoff et al. |
| 5,084,663 | A | 1/1992 | Olsson |
| 5,084,828 | A | 1/1992 | Kaufman et al. |
| 5,088,981 | A | 2/1992 | Howson et al. |
| 5,096,385 | A | 3/1992 | Georgi et al. |
| 5,097,505 | A | 3/1992 | Weiss |
| 5,100,380 | A | 3/1992 | Epstein et al. |
| 5,102,392 | A | 4/1992 | Sakai et al. |
| 5,103,211 | A | 4/1992 | Daoud et al. |

(56) References Cited

U.S. PATENT DOCUMENTS 5,104,374 A 4/1992 Bishko et al.
5,108,367 A 4/1992 Epstein et al.
5,109,850 A 5/1992 Blanco et al.
5,116,203 A 5/1992 Nartwick et al.
5,116,312 A 5/1992 Blakenship et al.
5,116,316 A 5/1992 Sertic
5,123,275 A 6/1992 Daoud et al.
5,124,627 A 6/1992 Okada
5,125,499 A 6/1992 Saathoff et al.
5,131,816 A 7/1992 Brown
5,132,603 A 7/1992 Yoshimoto
5,153,827 A 10/1992 Coutre et al.
5,158,441 A 10/1992 Aid
5,161,222 A 11/1992 Montejo et al.
5,174,472 A 12/1992 Raque et al.
5,176,631 A 1/1993 Koenig
5,176,646 A 1/1993 Kuroda
5,179,340 A 1/1993 Rogers
5,180,287 A 1/1993 Natwick et al.
5,181,910 A 1/1993 Scanlon
5,186,057 A 2/1993 Everhart
5,188,603 A 2/1993 Vaillancourt
5,190,522 A 3/1993 Wocicki et al.
5,191,795 A 3/1993 Fellingham et al.
5,192,340 A 3/1993 Grant et al.
5,194,796 A 3/1993 Domeki et al.
5,198,776 A 3/1993 Carr
5,200,090 A 4/1993 Ford
5,205,819 A 4/1993 Ross et al.
5,206,522 A 4/1993 Danby et al.
5,207,642 A 5/1993 Orkin et al.
5,211,626 A 5/1993 Frank et al.
5,213,573 A 5/1993 Sorich et al.
5,215,450 A 6/1993 Tamari
5,216,597 A 6/1993 Beckers
5,219,099 A 6/1993 Spence et al.
5,219,327 A 6/1993 Okada
5,221,268 A 6/1993 Barton et al.
5,229,713 A 7/1993 Bullock et al.
5,232,476 A 8/1993 Grant
5,233,571 A 8/1993 Wirtschafter
5,237,309 A 8/1993 Frantz et al.
5,242,406 A 9/1993 Gross et al.
5,242,408 A 9/1993 Jhuboo et al.
5,243,982 A 9/1993 Möstl et al.
5,244,463 A 9/1993 Cordner, Jr. et al.
5,244,568 A 9/1993 Lindsay et al.
5,254,096 A 10/1993 Rondelet et al.
5,256,155 A 10/1993 Yerlikaya et al.
5,256,156 A 10/1993 Kern et al.
5,256,157 A 10/1993 Samiotes et al.
5,260,665 A 11/1993 Goldberg
5,257,206 A 12/1993 Hanson
5,267,980 A 12/1993 Dirr et al.
5,274,316 A 12/1993 Evans et al.
5,276,610 A 1/1994 Maeda et al.
5,280,728 A 1/1994 Sato et al.
5,283,510 A 2/1994 Tamaki et al.
5,287,851 A 2/1994 Beran et al.
5,292,306 A 3/1994 Wynkoop et al.
5,295,967 A 3/1994 Rondelet et al.
5,298,021 A 3/1994 Sherer
5,303,585 A 4/1994 Lichte
5,304,126 A 4/1994 Epstein et al.
5,308,333 A 5/1994 Skakoon
5,317,506 A 5/1994 Coutre et al.
5,319,363 A 6/1994 Welch et al.
5,319,979 A 6/1994 Abrahamson
5,321,392 A 6/1994 Skakoon et al.
5,325,728 A 7/1994 Zimmerman et al.
5,328,460 A 7/1994 Lord et al.
5,330,634 A 7/1994 Wong et al.
5,333,497 A 8/1994 Braend et al.
5,336,051 A 8/1994 Tamari
5,338,157 A 8/1994 Blomquist
5,342,298 A 8/1994 Michaels
5,343,734 A 9/1994 Maeda et al.
5,343,885 A 9/1994 Grant
5,346,466 A 9/1994 Yerlikaya et al.
5,356,378 A 10/1994 Doan et al.
5,359,271 A 10/1994 Husher
D352,778 S 11/1994 Irvin et al.
5,364,346 A 11/1994 Schrezenmeir
5,366,346 A 11/1994 Danby
5,368,562 A 11/1994 Blomquist et al.
5,374,865 A 12/1994 Yoshimura et al.
5,376,070 A 12/1994 Purvis et al.
5,378,231 A 1/1995 Johnson et al.
5,382,232 A 1/1995 Hague et al.
5,383,369 A 1/1995 Khuri-Yakub et al.
5,389,071 A 2/1995 Kawahara et al.
5,389,078 A 2/1995 Zalesky et al.
5,392,638 A 2/1995 Kawahara
5,394,732 A 3/1995 Johnson et al.
5,395,320 A 3/1995 Padda et al.
5,399,171 A 3/1995 Bowman et al.
5,406,954 A 4/1995 Tomita
5,408,326 A 4/1995 Priestley
5,415,528 A 5/1995 Ogden et al.
5,417,119 A 5/1995 Smoll
5,417,222 A 5/1995 Dempsey et al.
5,417,395 A 5/1995 Fowler et al.
5,418,443 A 5/1995 Kikuchi
5,421,208 A 6/1995 Packard et al.
5,423,748 A 6/1995 Uhala
5,423,759 A 6/1995 Campbell
5,428,284 A 6/1995 Kaneda et al.
5,429,485 A 7/1995 Dodge
5,429,601 A 7/1995 Conley
5,429,602 A 7/1995 Hauser
5,431,627 A 7/1995 Pastrone et al.
5,434,508 A 7/1995 Ishida
5,437,624 A 8/1995 Langley et al.
5,444,316 A 8/1995 Ohya et al.
5,444,378 A 8/1995 Rogers
5,445,621 A 8/1995 Poli et al.
5,450,758 A 9/1995 Smoll
5,451,881 A 9/1995 Finger
5,455,423 A 10/1995 Mount et al.
5,455,851 A 10/1995 Chaco et al.
5,463,906 A 11/1995 Spani et al.
5,464,392 A 11/1995 Epstein et al.
5,465,082 A 11/1995 Chaco
5,469,851 A 11/1995 Lipschutz
5,473,948 A 12/1995 Moss et al.
5,480,294 A 1/1996 Di Perna et al.
5,482,438 A 1/1996 Anderson et al.
5,485,408 A 1/1996 Blomquist
5,486,286 A 1/1996 Peterson et al.
5,489,265 A 2/1996 Montalvo et al.
5,495,566 A 2/1996 Kwatinetz
5,496,273 A 3/1996 Pastrone et al.
5,505,696 A 4/1996 Miki
5,505,828 A 4/1996 Wong et al.
5,507,288 A 4/1996 Bocker et al.
5,507,412 A 4/1996 Ebert et al.
5,520,637 A 5/1996 Pager et al.
5,522,798 A 6/1996 Johnson et al.
5,522,799 A 6/1996 Furukawa
5,527,630 A 6/1996 Nagata
5,533,389 A 7/1996 Kamen et al.
5,537,853 A 7/1996 Finburgh et al.
5,542,040 A 7/1996 Chang et al.
5,545,140 A 8/1996 Conero et al.
5,547,470 A 8/1996 Johnson et al.
5,551,850 A 9/1996 Williamson et al.
5,554,013 A 9/1996 Owens et al.
5,554,115 A 9/1996 Thomas et al.
5,558,638 A 9/1996 Evers et al.
5,562,615 A 10/1996 Nassif
5,563,486 A 10/1996 Yamamoto et al.
5,572,105 A 11/1996 Nojima et al.
5,573,502 A 11/1996 LeCocq et al.
5,583,280 A 12/1996 Mo et al.

(56) References Cited

U.S. PATENT DOCUMENTS 5,584,667 A 12/1996 Davis
5,584,806 A 12/1996 Amano
5,586,868 A 12/1996 Lawless et al.
5,590,653 A 1/1997 Aida et al.
5,594,786 A 1/1997 Chaco et al.
5,600,073 A 2/1997 Hill
5,601,420 A 2/1997 Warner et al.
5,609,575 A 3/1997 Larson et al.
5,609,576 A 3/1997 Voss
5,611,784 A 3/1997 Barresi et al.
5,616,124 A 4/1997 Hague et al.
5,620,312 A 4/1997 Hyman et al.
5,620,608 A 4/1997 Rosa et al.
5,626,140 A 5/1997 Feldman et al.
5,626,151 A 5/1997 Linden
5,626,563 A 5/1997 Dodge et al.
5,627,443 A 5/1997 Kimura et al.
5,628,309 A 5/1997 Brown
5,628,731 A 5/1997 Dodge et al.
5,630,710 A 5/1997 Tune et al.
5,634,896 A 6/1997 Bryant et al.
5,637,095 A 6/1997 Nason et al.
5,640,075 A 6/1997 Brasseur et al.
5,640,150 A 6/1997 Atwater
5,643,212 A 7/1997 Coutre et al.
5,648,710 A 7/1997 Ikeda
5,649,536 A 7/1997 Ogura et al.
5,651,775 A 7/1997 Walker et al.
5,657,000 A 8/1997 Ellingboe
5,658,133 A 8/1997 Anderson et al.
5,658,250 A 8/1997 Blomquist et al.
5,659,234 A 8/1997 Cresens
5,661,245 A 8/1997 Svoboda et al.
5,662,612 A 9/1997 Niehoff
5,665,065 A 9/1997 Colman et al.
5,669,877 A 9/1997 Blomquist
5,672,154 A 9/1997 Sillén et al.
5,672,832 A 9/1997 Cucci et al.
5,681,285 A 10/1997 Ford et al.
5,681,286 A 10/1997 Niehoff
5,685,844 A 11/1997 Marttila
5,687,717 A 11/1997 Halpern et al.
5,689,229 A 11/1997 Chaco et al.
5,691,613 A 11/1997 Gutwillinger
5,695,464 A 12/1997 Viallet
5,695,473 A 12/1997 Olsen
5,697,899 A 12/1997 Hillman et al.
5,697,916 A 12/1997 Schraga
5,712,795 A 1/1998 Layman et al.
5,713,856 A 2/1998 Eggers et al.
5,714,691 A 2/1998 Hill
5,718,562 A 2/1998 Lawless et al.
5,718,569 A 2/1998 Holst
5,720,721 A 2/1998 Dumas et al.
5,722,417 A 3/1998 Rudolph
5,728,074 A 3/1998 Castellano et al.
5,728,948 A 3/1998 Bignell et al.
5,733,257 A 3/1998 Stemby
5,733,259 A 3/1998 Valcke et al.
5,738,659 A 4/1998 Neer et al.
5,743,856 A 4/1998 Oka et al.
5,744,027 A 4/1998 Connell et al.
5,744,929 A 4/1998 Miyazaki
5,745,378 A 4/1998 Barker et al.
5,752,813 A 5/1998 Tyner et al.
5,752,918 A 5/1998 Fowler et al.
5,752,919 A 5/1998 Schrimpf
5,755,691 A 5/1998 Hilborne
5,758,643 A 6/1998 Wong et al.
5,761,072 A 6/1998 Bardsley, Jr. et al.
5,764,034 A 6/1998 Bowman et al.
5,766,155 A 6/1998 Hyman et al.
5,772,635 A 6/1998 Dastur et al.
5,778,256 A 7/1998 Darbee
5,781,442 A 7/1998 Engleson et al.
5,782,805 A 7/1998 Meinzer et al.
5,788,669 A 8/1998 Peterson
5,788,674 A 8/1998 McWilliams
5,789,923 A 8/1998 Shimoyama et al.
5,792,069 A 8/1998 Greenwald et al.
5,793,211 A 8/1998 Shimoyama et al.
5,795,327 A 8/1998 Wilson et al.
5,798,934 A 8/1998 Saigo et al.
5,800,387 A 9/1998 Duffy et al.
5,803,712 A 9/1998 Davis et al.
5,803,917 A 9/1998 Butterfield
5,805,455 A 9/1998 Lipps
5,807,322 A 9/1998 Lindsey et al.
5,810,770 A 9/1998 Chin et al.
5,813,972 A 9/1998 Nazarian et al.
5,814,004 A 9/1998 Tamari
5,814,015 A 9/1998 Gargano et al.
5,816,779 A 10/1998 Lawless et al.
5,822,715 A 10/1998 Worthington et al.
5,827,179 A 10/1998 Lichter et al.
5,827,223 A 10/1998 Butterfield
5,832,448 A 11/1998 Brown
5,836,910 A 11/1998 Duffy et al.
5,841,261 A 11/1998 Nojima et al.
5,841,284 A 11/1998 Takahashi
5,843,035 A 12/1998 Bowman
5,848,971 A 12/1998 Fowler et al.
5,850,344 A 12/1998 Conkright
5,857,843 A 1/1999 Leason et al.
5,864,330 A 1/1999 Haynes
5,865,805 A 2/1999 Ziemba
5,867,821 A 2/1999 Ballantyne et al.
5,871,465 A 2/1999 Vasko
5,872,453 A 2/1999 Shimoyama et al.
5,875,195 A 2/1999 Dixon
5,882,300 A 3/1999 Malinouskas et al.
5,882,339 A 3/1999 Beiser et al.
5,885,245 A 3/1999 Lynch et al.
5,889,379 A 3/1999 Yanagi et al.
5,891,051 A 4/1999 Han et al.
5,894,209 A 4/1999 Takagi et al.
5,897,493 A 4/1999 Brown
5,897,498 A 4/1999 Canfield, II et al.
5,898,292 A 4/1999 Takemoto et al.
5,899,665 A 5/1999 Makino et al.
5,901,150 A 5/1999 Jhuboo et al.
5,904,666 A 5/1999 DeDecker et al.
5,904,668 A 5/1999 Hyman et al.
5,905,207 A 5/1999 Schalk
5,906,598 A 5/1999 Giesier
5,910,252 A 6/1999 Truitt et al.
5,915,240 A 6/1999 Karpf
5,920,263 A 7/1999 Huttenhoff et al.
5,923,159 A 7/1999 Ezell
5,924,074 A 7/1999 Evans
5,927,349 A 7/1999 Martucci
5,932,119 A 8/1999 Kaplan et al.
5,932,987 A 8/1999 McLoughlin
5,935,099 A 8/1999 Peterson et al.
5,935,106 A * 8/1999 Olsen ................ A61M 5/16859
604/153
5,938,634 A 8/1999 Packard
5,938,636 A 8/1999 Kramer et al.
5,941,846 A 8/1999 Duffy et al.
5,944,660 A 8/1999 Kimball et al.
5,947,911 A 9/1999 Wong et al.
5,954,527 A 9/1999 Jhuboo et al.
5,954,696 A 9/1999 Ryan et al.
5,956,023 A 9/1999 Lyle et al.
5,956,501 A 9/1999 Brown
5,957,885 A 9/1999 Bollish et al.
5,957,890 A 9/1999 Mann et al.
5,971,594 A 10/1999 Sahai et al.
5,973,497 A 10/1999 Bergk et al.
5,975,081 A 11/1999 Hood et al.
5,989,222 A 11/1999 Cole et al.
5,990,838 A 11/1999 Burns et al.
5,991,525 A 11/1999 Shah et al.
5,993,393 A 11/1999 Ryan et al.

(56) References Cited

U.S. PATENT DOCUMENTS 5,994,876 A 11/1999 Canny et al.
5,997,476 A 12/1999 Brown
6,000,828 A 12/1999 Leet
6,003,006 A 12/1999 Colella et al.
6,003,388 A 12/1999 Oeftering
6,012,034 A 1/2000 Hamparian et al.
6,017,318 A 1/2000 Gauthier et al.
6,017,493 A 1/2000 Cambron
6,021,392 A 2/2000 Lester et al.
6,023,977 A 2/2000 Langdon et al.
6,024,539 A 2/2000 Blomquist
6,027,441 A 2/2000 Cantu
6,032,676 A 3/2000 Moore
6,033,561 A 3/2000 Schoendorfer
6,036,017 A 3/2000 Bayliss, IV
6,068,612 A 5/2000 Bowman
6,068,615 A 5/2000 Brown et al.
6,073,106 A 6/2000 Rozen et al.
6,077,246 A 6/2000 Kullas et al.
6,083,206 A 7/2000 Molko
6,089,104 A 7/2000 Chang
6,104,295 A 8/2000 Gaisser et al.
6,110,152 A 8/2000 Kovelman
6,110,153 A 8/2000 Davis
RE36,871 E 9/2000 Epstein et al.
6,120,459 A 9/2000 Nitzan et al.
6,122,536 A 9/2000 Sun et al.
6,142,008 A 11/2000 Cole et al.
6,150,942 A 11/2000 O'Brien
6,157,914 A 12/2000 Seto et al.
6,158,288 A 12/2000 Smith
6,158,965 A 12/2000 Butterfield et al.
6,159,147 A 12/2000 Lichter et al.
6,159,186 A 12/2000 Wickham et al.
6,164,921 A 12/2000 Moubayed et al.
6,168,561 B1 1/2001 Cantu
6,178,827 B1 1/2001 Feller
6,182,667 B1 2/2001 Hanks et al.
6,186,141 B1 2/2001 Pike et al.
6,189,105 B1 2/2001 Lopes
6,192,752 B1 2/2001 Blaine
6,195,589 B1 2/2001 Ketcham
6,202,711 B1 3/2001 Martucci
6,203,528 B1 3/2001 Deckert
6,208,107 B1 3/2001 Maske et al.
6,212,936 B1 4/2001 Meisberger
6,213,972 B1 4/2001 Butterfield
6,231,320 B1 5/2001 Lawless et al.
6,234,176 B1 5/2001 Domae et al.
6,236,326 B1 5/2001 Murphy et al.
6,237,398 B1 5/2001 Porat et al.
6,241,704 B1 6/2001 Peterson et al.
6,248,067 B1 6/2001 Causey, III et al.
6,250,132 B1 6/2001 Drzewiecki
6,259,355 B1 7/2001 Chaco et al.
6,259,587 B1 7/2001 Sheldon et al.
6,261,065 B1 7/2001 Nayak
6,262,946 B1 7/2001 Khuri-Yakub et al.
6,267,559 B1 7/2001 Mossman et al.
6,267,725 B1 7/2001 Dubberstein et al.
6,269,340 B1 7/2001 Ford et al.
6,270,455 B1 8/2001 Brown
6,271,813 B1 8/2001 Palalau
6,277,072 B1 8/2001 Bardy
6,277,099 B1 8/2001 Strowe et al.
6,280,380 B1 8/2001 Bardy
6,280,391 B1 8/2001 Olson et al.
6,280,408 B1 8/2001 Sipin
6,283,761 B1 9/2001 Joao
6,285,155 B1 9/2001 Maske et al.
6,312,378 B1 11/2001 Bardy
6,322,516 B1 11/2001 Masuda et al.
6,330,351 B1 12/2001 Yasunaga
6,337,675 B1 1/2002 Toffolo et al.
6,345,539 B1 2/2002 Rawes et al.
6,347,553 B1 2/2002 Morris et al.
6,349,740 B1 2/2002 Cho et al.
6,358,225 B1 3/2002 Butterfield
6,362,591 B1 3/2002 Moberg
6,385,505 B1 5/2002 Lipps
6,386,050 B1 5/2002 Yin et al.
6,394,958 B1 5/2002 Bratteli et al.
6,396,583 B1 5/2002 Clare
6,398,760 B1 6/2002 Danby
6,405,076 B1 6/2002 Taylor et al.
6,408,679 B1 6/2002 Kline-Schoder et al.
6,413,238 B1 7/2002 Maget
6,416,291 B1 7/2002 Butterfield et al.
6,418,334 B1 7/2002 Unger et al.
6,418,535 B1 7/2002 Kulakowski et al.
6,445,053 B1 9/2002 Cho
6,456,245 B1 9/2002 Crawford
6,457,346 B1 10/2002 Kline-Schoder et al.
6,463,785 B1 10/2002 Kline-Schoder et al.
6,467,331 B1 10/2002 Kline-Schoder et al.
6,468,242 B1 10/2002 Wilson et al.
6,475,178 B1 11/2002 Krajewski
6,481,980 B1 11/2002 Vandlik
6,482,158 B2 11/2002 Mault
6,482,185 B1 11/2002 Hartmann
6,485,263 B1 11/2002 Bryant et al.
6,485,418 B2 11/2002 Yasushi et al.
6,485,465 B2 11/2002 Moberg et al.
6,487,916 B1 12/2002 Gomm et al.
6,489,896 B1 12/2002 Platt
6,494,694 B2 12/2002 Lawless et al.
6,494,831 B1 12/2002 Koritzinsky
6,497,680 B1 12/2002 Holst et al.
6,503,221 B1 1/2003 Briggs
6,512,944 B1 1/2003 Kovtun et al.
6,516,667 B1 2/2003 Broad et al.
6,517,482 B1 2/2003 Eiden et al.
6,519,569 B1 2/2003 White et al.
6,529,751 B1 3/2003 Van Driel et al.
6,531,708 B1 3/2003 Malmstrom
6,539,315 B1 3/2003 Adams et al.
6,540,672 B1 4/2003 Simonsen et al.
6,544,212 B2 4/2003 Galley et al.
6,544,228 B1 4/2003 Heitmeier
6,558,125 B1 5/2003 Futterknecht
6,558,351 B1 5/2003 Steil et al.
6,562,012 B1 5/2003 Brown et al.
6,564,825 B2 5/2003 Lowery et al.
6,565,509 B1 5/2003 Say et al.
6,568,416 B2 5/2003 Tucker et al.
6,572,542 B1 6/2003 Houben et al.
6,572,545 B2 6/2003 Knobbe et al.
6,572,576 B2 6/2003 Brugger et al.
6,578,422 B2 6/2003 Lam et al.
6,578,435 B2 6/2003 Gould et al.
6,581,117 B1 6/2003 Klein et al.
RE38,189 E 7/2003 Walker et al.
6,585,675 B1 7/2003 O'Mahony et al.
6,589,229 B1 7/2003 Connelly et al.
6,589,792 B1 7/2003 Malachowski
6,599,281 B1 7/2003 Struys et al.
6,599,282 B2 7/2003 Burko
6,602,191 B2 8/2003 Quy
6,605,072 B2 8/2003 Struys et al.
6,609,047 B1 8/2003 Lipps
6,615,674 B2 9/2003 Ohnishi
6,616,633 B1 9/2003 Butterfield et al.
6,617,564 B2 9/2003 Ockerse et al.
6,618,916 B1 9/2003 Eberle et al.
6,622,542 B2 9/2003 Derek
6,622,561 B2 9/2003 Lam et al.
D481,121 S 10/2003 Evans
6,629,449 B1 10/2003 Kline-Schoder et al.
6,634,233 B2 10/2003 He
6,640,246 B1 10/2003 Gardy, Jr. et al.
6,641,533 B2 11/2003 Causey, III et al.
6,641,541 B1 11/2003 Lovett et al.
6,648,861 B2 11/2003 Platt et al.
6,652,455 B1 11/2003 Kocher

(56) References Cited

U.S. PATENT DOCUMENTS

| | | |
|---|---|---|
| 6,653,937 B2 | 11/2003 | Nelson et al. |
| 6,659,980 B2 | 12/2003 | Moberg et al. |
| D485,356 S | 1/2004 | Evans |
| 6,685,668 B1 | 2/2004 | Cho et al. |
| 6,685,678 B2 | 2/2004 | Evans et al. |
| 6,689,069 B2 | 2/2004 | Bratteli et al. |
| 6,689,091 B2 | 2/2004 | Bui et al. |
| 6,692,241 B2 | 2/2004 | Watanabe et al. |
| 6,716,004 B2 | 4/2004 | Vandlik |
| 6,719,535 B2 | 4/2004 | Rakestraw et al. |
| 6,721,582 B2 | 4/2004 | Trepagnier et al. |
| 6,722,211 B1 | 4/2004 | Ciobanu et al. |
| 6,725,200 B1 | 4/2004 | Rost |
| 6,725,721 B2 | 4/2004 | Venczel |
| 6,731,989 B2 | 5/2004 | Engleson et al. |
| 6,732,595 B2 | 5/2004 | Lynnworth |
| 6,738,052 B1 | 5/2004 | Manke et al. |
| 6,740,072 B2 | 5/2004 | Starkweather et al. |
| 6,741,212 B2 | 5/2004 | Kralovec et al. |
| 6,748,808 B2 | 6/2004 | Lam et al. |
| 6,749,403 B2 | 6/2004 | Bryant et al. |
| 6,752,787 B1 | 6/2004 | Causey, III et al. |
| 6,753,842 B1 | 6/2004 | Williams et al. |
| 6,759,007 B1 | 7/2004 | Westberg |
| 6,760,643 B2 | 7/2004 | Lipps |
| 6,768,920 B2 | 7/2004 | Lange |
| 6,773,412 B2 | 8/2004 | O'Mahony |
| 6,780,156 B2 | 8/2004 | Haueter et al. |
| 6,783,328 B2 | 8/2004 | Lucke et al. |
| 6,785,573 B2 | 8/2004 | Kovtun et al. |
| 6,786,885 B2 | 9/2004 | Hochman et al. |
| 6,789,426 B2 | 9/2004 | Yaralioglu et al. |
| 6,790,198 B1 | 9/2004 | White et al. |
| 6,793,625 B2 | 9/2004 | Cavallaro et al. |
| 6,801,227 B2 | 10/2004 | Bocionek et al. |
| 6,805,671 B2 | 10/2004 | Stergiopoulos et al. |
| 6,807,965 B1 | 10/2004 | Hickle |
| 6,809,653 B1 | 10/2004 | Mann et al. |
| 6,813,964 B1 | 11/2004 | Clark et al. |
| 6,814,547 B2 | 11/2004 | Childers |
| 6,824,528 B1 | 11/2004 | Faries |
| 6,830,558 B2 | 12/2004 | Flaherty et al. |
| 6,840,113 B2 | 1/2005 | Fukumura et al. |
| 6,846,161 B2 | 1/2005 | Kline |
| 6,852,094 B2 | 2/2005 | Beck |
| 6,852,104 B2 | 2/2005 | Blomquist |
| 6,854,338 B2 | 2/2005 | Khuri-Yakub et al. |
| 6,857,318 B1 | 2/2005 | Silber et al. |
| 6,869,425 B2 | 3/2005 | Briggs et al. |
| 6,873,268 B2 | 3/2005 | Lebel et al. |
| 6,883,376 B2 | 4/2005 | He |
| 6,885,881 B2 | 4/2005 | Leonhardt |
| 6,887,216 B2 | 5/2005 | Hochman et al. |
| 6,898,301 B2 | 5/2005 | Iwanaga |
| 6,907,361 B2 | 6/2005 | Molenaar |
| 6,907,792 B2 | 6/2005 | Ohnishi |
| 6,915,170 B2 | 7/2005 | Engleson et al. |
| 6,920,795 B2 | 7/2005 | Bischoff et al. |
| 6,923,763 B1 | 8/2005 | Kovatchev et al. |
| 6,928,338 B1 | 8/2005 | Buchser et al. |
| 6,929,619 B2 | 8/2005 | Fago et al. |
| 6,929,751 B2 | 8/2005 | Bowman |
| 6,932,114 B2 | 8/2005 | Sparks |
| 6,932,796 B2 | 8/2005 | Sage et al. |
| 6,935,192 B2 | 8/2005 | Sobek et al. |
| 6,936,029 B2 | 8/2005 | Mann et al. |
| 6,941,005 B2 | 9/2005 | Lary et al. |
| 6,942,636 B2 | 9/2005 | Holst et al. |
| 6,945,954 B2 | 9/2005 | Hochman et al. |
| 6,958,705 B2 | 10/2005 | Lebel et al. |
| 6,964,204 B2 | 11/2005 | Clark et al. |
| 6,973,374 B2 | 12/2005 | Ader |
| 6,974,437 B2 | 12/2005 | Lebel et al. |
| 6,975,922 B2 | 12/2005 | Duncan et al. |
| 6,978,779 B2 | 12/2005 | Haveri et al. |
| 6,979,326 B2 | 12/2005 | Mann et al. |
| 6,981,960 B2 | 1/2006 | Cho et al. |
| 6,984,218 B2 | 1/2006 | Nayak et al. |
| 6,985,768 B2 | 1/2006 | Hemming et al. |
| 6,985,870 B2 | 1/2006 | Martucci et al. |
| 6,986,347 B2 | 1/2006 | Hickle |
| 6,986,753 B2 | 1/2006 | Bui |
| 6,997,905 B2 | 2/2006 | Gillespie, Jr. et al. |
| 6,997,920 B2 | 2/2006 | Mann et al. |
| 7,006,005 B2 | 2/2006 | Nazarian et al. |
| 7,017,623 B2 | 3/2006 | Tribble et al. |
| 7,021,148 B2 | 4/2006 | Kuhn |
| 7,025,743 B2 | 4/2006 | Mann et al. |
| 7,029,455 B2 | 4/2006 | Flaherty |
| 7,029,456 B2 | 4/2006 | Ware et al. |
| 7,059,184 B2 | 6/2006 | Kanouola et al. |
| 7,060,059 B2 | 6/2006 | Keith et al. |
| 7,069,793 B2 | 7/2006 | Ishikawa et al. |
| 7,072,725 B2 | 7/2006 | Bristol et al. |
| 7,074,209 B2 | 7/2006 | Evans et al. |
| 7,080,557 B2 | 7/2006 | Adnan |
| 7,082,843 B2 | 8/2006 | Clark et al. |
| 7,092,796 B2 | 8/2006 | Vanderveen |
| 7,092,797 B2 | 8/2006 | Gaines et al. |
| 7,093,502 B2 | 8/2006 | Kupnik et al. |
| 7,096,729 B2 | 8/2006 | Repko et al. |
| 7,103,419 B2 | 9/2006 | Engleson et al. |
| 7,104,763 B2 | 9/2006 | Bouton et al. |
| 7,104,769 B2 | 9/2006 | Davis |
| 7,108,680 B2 | 9/2006 | Rohr et al. |
| 7,109,878 B2 | 9/2006 | Mann et al. |
| 7,115,113 B2 | 10/2006 | Evans et al. |
| 7,117,041 B2 | 10/2006 | Engleson et al. |
| 7,137,964 B2 | 11/2006 | Flaherty |
| 7,141,037 B2 | 11/2006 | Butterfield et al. |
| 7,152,490 B1 | 12/2006 | Freund, Jr. et al. |
| 7,154,397 B2 | 12/2006 | Zerhusen et al. |
| 7,161,488 B2 | 1/2007 | Frasch |
| 7,162,290 B1 | 1/2007 | Levin |
| 7,162,927 B1 | 1/2007 | Selvan et al. |
| 7,171,277 B2 | 1/2007 | Engleson et al. |
| 7,174,789 B2 | 2/2007 | Orr et al. |
| 7,185,288 B2 | 2/2007 | McKeever |
| 7,197,943 B2 | 4/2007 | Lee et al. |
| 7,201,734 B2 | 4/2007 | Hickle |
| 7,204,823 B2 | 4/2007 | Estes et al. |
| 7,206,715 B2 | 4/2007 | Vanderveen et al. |
| 7,213,009 B2 | 5/2007 | Pestotnik |
| 7,220,240 B2 | 5/2007 | Struys et al. |
| 7,229,430 B2 | 6/2007 | Hickle et al. |
| 7,230,529 B2 | 6/2007 | Ketcherside |
| 7,232,430 B2 | 6/2007 | Carlisle |
| 7,238,164 B2 | 7/2007 | Childers et al. |
| 7,247,154 B2 | 7/2007 | Hickle |
| 7,253,779 B2 | 8/2007 | Greer et al. |
| 7,254,425 B2 | 8/2007 | Lowery et al. |
| 7,258,534 B2 | 8/2007 | Fathallah et al. |
| 7,267,664 B2 | 9/2007 | Rizzo |
| 7,267,665 B2 | 9/2007 | Steil et al. |
| 7,272,529 B2 | 9/2007 | Hogan et al. |
| 7,278,983 B2 | 10/2007 | Ireland et al. |
| 7,291,123 B2 | 11/2007 | Baraldi et al. |
| 7,293,461 B1 | 11/2007 | Girndt |
| 7,294,109 B2 | 11/2007 | Lovett et al. |
| 7,296,482 B2 | 11/2007 | Schaffer et al. |
| 7,300,418 B2 | 11/2007 | Zaleski |
| 7,305,883 B2 | 12/2007 | Khuri-Yakub et al. |
| 7,327,273 B2 | 2/2008 | Hung et al. |
| 7,338,470 B2 | 3/2008 | Katz |
| 7,347,836 B2 | 3/2008 | Peterson et al. |
| 7,354,420 B2 | 4/2008 | Steil et al. |
| 7,356,382 B2 | 4/2008 | Vanderveen |
| 7,360,999 B2 | 4/2008 | Nelson et al. |
| 7,364,562 B2 | 4/2008 | Braig et al. |
| 7,367,942 B2 | 5/2008 | Grage et al. |
| 7,369,948 B1 | 5/2008 | Ferenczi et al. |
| 7,384,410 B2 | 6/2008 | Eggers et al. |
| 7,397,166 B1 | 7/2008 | Morgan et al. |
| 7,398,183 B2 | 7/2008 | Holland et al. |

(56) References Cited

U.S. PATENT DOCUMENTS 7,399,277 B2 7/2008 Saidara et al.
7,402,153 B2 7/2008 Steil et al.
7,402,154 B2 7/2008 Mendez
7,407,489 B2 8/2008 Mendez
7,414,534 B1 8/2008 Kroll et al.
7,415,895 B2 8/2008 Kurisaki et al.
7,426,443 B2 9/2008 Simon
7,430,675 B2 9/2008 Lee et al.
7,447,566 B2 11/2008 Knauper et al.
7,447,643 B1 11/2008 Olson
7,452,190 B2 11/2008 Bouton et al.
7,454,314 B2 11/2008 Holland et al.
7,471,994 B2 12/2008 Ford et al.
7,482,818 B2 1/2009 Greenwald et al.
7,483,756 B2 1/2009 Engleson et al.
7,490,021 B2 2/2009 Holland et al.
7,491,187 B2 2/2009 Van Den Berghe et al.
7,503,903 B2 3/2009 Carlisle et al.
7,517,332 B2 4/2009 Tonelli et al.
7,523,401 B1 4/2009 Aldridge
7,545,075 B2 6/2009 Huang et al.
7,556,616 B2 7/2009 Fathallah et al.
7,561,986 B2 7/2009 Vanderveen et al.
7,571,024 B2 8/2009 Duncan et al.
7,645,258 B2 1/2010 White et al.
7,654,127 B2 2/2010 Krulevitch et al.
7,657,443 B2 2/2010 Crass
7,668,731 B2 2/2010 Martucci et al.
7,678,048 B1 3/2010 Urbano et al.
7,693,697 B2 4/2010 Westenkow et al.
7,699,806 B2 4/2010 Ware et al.
7,705,727 B2 4/2010 Pestotnik
7,766,873 B2 8/2010 Moberg et al.
7,775,126 B2 8/2010 Eckhardt
7,775,127 B2 8/2010 Wade
7,785,284 B2 8/2010 Baralsi et al.
7,785,313 B2 8/2010 Mastrototaro
7,786,909 B2 8/2010 Udupa et al.
7,806,886 B2 10/2010 Kanderian, Jr. et al.
7,826,981 B2 11/2010 Goode, Jr. et al.
7,847,276 B2 12/2010 Carlisle
7,860,583 B2 12/2010 Condurso et al.
7,871,394 B2 1/2011 Halbert et al.
7,876,443 B2 1/2011 Bernacki
7,895,053 B2 2/2011 Holland et al.
7,895,882 B2 3/2011 Carlisle
7,896,834 B2 3/2011 Smisson, III
7,896,842 B2 3/2011 Palmroos et al.
7,905,710 B2 3/2011 Wang et al.
7,933,780 B2 4/2011 de la Huerga
7,945,452 B2 5/2011 Fathallah et al.
7,981,073 B2 7/2011 Mollstam
7,981,082 B2 7/2011 Wang et al.
8,034,020 B2 10/2011 Dewey
8,038,593 B2 10/2011 Friedman et al.
8,065,161 B2 11/2011 Howard et al.
8,067,760 B2 11/2011 Carlisle
8,075,546 B2 12/2011 Carlisle et al.
8,078,983 B2 12/2011 Davis et al.
8,121,857 B2 2/2012 Galasso et al.
8,149,131 B2 4/2012 Blomquist
8,175,668 B1 5/2012 Nabutovsky et al.
8,177,739 B2 5/2012 Cartledge et al.
8,185,322 B2 5/2012 Schroeder et al.
8,219,413 B2 7/2012 Martinez et al.
8,226,597 B2 7/2012 Jacobson et al.
8,231,578 B2 7/2012 Fathallah et al.
8,234,128 B2 7/2012 Martucci et al.
8,271,106 B2 9/2012 Wehba et al.
8,287,514 B2 10/2012 Miller et al.
8,291,337 B2 10/2012 Gannin et al.
8,313,308 B2 11/2012 Lawless et al.
8,317,698 B2 11/2012 Lowery
8,317,750 B2 11/2012 Ware et al.
8,317,752 B2 11/2012 Cozmi et al.
8,340,792 B2 12/2012 Condurso et al.
8,347,731 B2 1/2013 Genosar
8,359,338 B2 1/2013 Butterfield et al.
8,361,021 B2 1/2013 Wang et al.
8,378,837 B2 2/2013 Wang et al.
8,388,598 B2 3/2013 Steinkogler
8,398,616 B2 3/2013 Budiman
8,403,908 B2 3/2013 Jacobson et al.
8,449,524 B2 5/2013 Braig et al.
8,494,879 B2 7/2013 Davis et al.
8,504,179 B2 8/2013 Blomquist
8,517,990 B2 8/2013 Teel et al.
8,518,021 B2 8/2013 Stewart et al.
8,539,812 B2 9/2013 Stringham et al.
8,543,416 B2 9/2013 Palmroos et al.
8,577,692 B2 11/2013 Silkaitis et al.
8,622,990 B2 1/2014 Estes et al.
8,630,722 B2 1/2014 Condurso et al.
8,665,214 B2 3/2014 Forutanpour et al.
8,666,769 B2 3/2014 Butler et al.
8,700,421 B2 4/2014 Feng et al.
8,706,233 B2 4/2014 Su et al.
8,721,584 B2 5/2014 Braithwaite et al.
8,761,906 B2 6/2014 Condurso et al.
8,768,719 B2 7/2014 Wehba et al.
8,771,251 B2 7/2014 Ruchti et al.
8,792,981 B2 7/2014 Yudovsky et al.
8,821,432 B2 9/2014 Unverdorben
8,823,382 B2 9/2014 Rondoni et al.
8,857,269 B2 10/2014 Johnson et al.
8,858,185 B2 10/2014 Johnson et al.
8,964,185 B1 2/2015 Luo et al.
9,005,150 B2 4/2015 Ware et al.
9,026,370 B2 5/2015 Rubalcaba et al.
9,084,855 B2 7/2015 Ware et al.
9,114,217 B2 8/2015 Sur et al.
9,134,735 B2 9/2015 Lowery et al.
9,134,736 B2 9/2015 Lowery et al.
9,138,526 B2 9/2015 Ware et al.
9,190,010 B2 11/2015 Vik et al.
9,240,002 B2 1/2016 Hume et al.
9,272,089 B2 3/2016 Jacobson et al.
9,333,291 B2 5/2016 Jacobson et al.
9,381,296 B2 7/2016 Arrizza et al.
9,393,362 B2 7/2016 Cozmi et al.
9,468,718 B2 10/2016 Hung et al.
9,498,583 B2 11/2016 Sur et al.
9,707,341 B2 7/2017 Dumas, III et al.
9,943,269 B2 4/2018 Muhsin et al.
9,995,611 B2 6/2018 Ruchti et al.
2001/0007636 A1 7/2001 Butterfield
2001/0014769 A1 8/2001 Bufe et al.
2001/0015099 A1 8/2001 Blaine
2001/0016056 A1 8/2001 Westphal et al.
2001/0032099 A1 10/2001 Joao
2001/0037060 A1 11/2001 Thompson et al.
2001/0041869 A1 11/2001 Causey et al.
2001/0044731 A1 11/2001 Coffman et al.
2002/0003892 A1 1/2002 Iwanaga
2002/0007116 A1 1/2002 Zatezalo et al.
2002/0013545 A1 1/2002 Soltanpour et al.
2002/0013551 A1 1/2002 Zaitsu et al.
2002/0015018 A1 2/2002 Shimazu et al.
2002/0018720 A1 2/2002 Carlisle et al.
2002/0029776 A1 3/2002 Blomquist
2002/0032583 A1 3/2002 Joao
2002/0040208 A1 4/2002 Flaherty et al.
2002/0044059 A1 4/2002 Reeder et al.
2002/0045806 A1 4/2002 Baker, Jr. et al.
2002/0077852 A1 6/2002 Ford et al.
2002/0082728 A1 6/2002 Mueller et al.
2002/0083771 A1 7/2002 Khuri-Yakub et al.
2002/0085952 A1 7/2002 Ellingboe et al.
2002/0087115 A1 7/2002 Hartlaub
2002/0095486 A1 7/2002 Bahl
2002/0099282 A1 7/2002 Knobbe et al.
2002/0099334 A1 7/2002 Hanson et al.
2002/0143580 A1 10/2002 Bristol et al.
2002/0147389 A1 10/2002 Cavallaro et al.

(56) References Cited

U.S. PATENT DOCUMENTS

2002/0152239 A1 10/2002 Bautista-Lloyd et al.
2002/0168278 A1 11/2002 Jeon et al.
2002/0173703 A1 11/2002 Lebel et al.
2002/0183693 A1 12/2002 Peterson et al.
2003/0009244 A1 1/2003 Engleson
2003/0013959 A1 1/2003 Grunwald et al.
2003/0018308 A1 1/2003 Tsai
2003/0025602 A1 2/2003 Medema et al.
2003/0028082 A1 2/2003 Thompson
2003/0030001 A1 2/2003 Cooper et al.
2003/0045840 A1 3/2003 Burko
2003/0050621 A1 3/2003 Lebel et al.
2003/0060688 A1 3/2003 Ciarniello et al.
2003/0060765 A1 3/2003 Campbell et al.
2003/0065537 A1 4/2003 Evans
2003/0065589 A1 4/2003 Giacchetti
2003/0073954 A1 4/2003 Moberg et al.
2003/0079746 A1 5/2003 Hickle
2003/0083583 A1 5/2003 Kovtun et al.
2003/0091442 A1 5/2003 Bush et al.
2003/0104982 A1 6/2003 Wittmann et al.
2003/0106553 A1 6/2003 Vanderveen
2003/0125662 A1 7/2003 Bui
2003/0130616 A1 7/2003 Steil
2003/0135087 A1 7/2003 Hickle et al.
2003/0136193 A1 7/2003 Fujimoto
2003/0139701 A1 7/2003 White et al.
2003/0140928 A1 7/2003 Bui et al.
2003/0141981 A1 7/2003 Bui et al.
2003/0143746 A1 7/2003 Sage, Jr.
2003/0144878 A1 7/2003 Wilkes et al.
2003/0158508 A1 8/2003 DiGianfilippo
2003/0160683 A1 8/2003 Blomquist
2003/0163789 A1 8/2003 Blomquist
2003/0173408 A1 9/2003 Mosher, Jr. et al.
2003/0187338 A1 10/2003 Say et al.
2003/0200116 A1 10/2003 Forrester
2003/0204274 A1 10/2003 Ullestad et al.
2003/0204416 A1 10/2003 Acharya
2003/0212364 A1 11/2003 Mann et al.
2003/0212379 A1 11/2003 Bylund et al.
2003/0217962 A1 11/2003 Childers et al.
2003/0233071 A1 12/2003 Gillespie, Jr. et al.
2004/0030277 A1 2/2004 O'Mahony et al.
2004/0047736 A1 3/2004 Nose et al.
2004/0057226 A1 3/2004 Berthou et al.
2004/0064342 A1 4/2004 Browne et al.
2004/0073125 A1 4/2004 Lovett et al.
2004/0073161 A1 4/2004 Tachibana
2004/0077996 A1 4/2004 Jasperson et al.
2004/0082908 A1 4/2004 Whitehurst
2004/0082918 A1 4/2004 Evans et al.
2004/0104271 A1 6/2004 Martucci et al.
2004/0119753 A1 6/2004 Zencke
2004/0120825 A1 6/2004 Bouton et al.
2004/0145114 A1 6/2004 Ippolito et al.
2004/0128162 A1 7/2004 Schlotterbeck et al.
2004/0133166 A1 7/2004 Moberg et al.
2004/0147034 A1 7/2004 Gore et al.
2004/0149823 A1 8/2004 Aptekar
2004/0152970 A1 8/2004 Hunter et al.
2004/0158193 A1 8/2004 Bui et al.
2004/0167464 A1 8/2004 Ireland et al.
2004/0167465 A1 8/2004 Kohler
2004/0167804 A1 8/2004 Simpson
2004/0172222 A1 9/2004 Simpson et al.
2004/0172283 A1 9/2004 Vanderveen
2004/0172289 A1 9/2004 Kozic et al.
2004/0172302 A1 9/2004 Martucci et al.
2004/0176984 A1 9/2004 White et al.
2004/0181314 A1 9/2004 Zaleski
2004/0193025 A1 9/2004 Steil et al.
2004/0193325 A1 9/2004 Bonderud
2004/0193328 A1 9/2004 Butterfield et al.
2004/0193453 A1 9/2004 Butterfield et al.
2004/0204638 A1 10/2004 Diab et al.
2004/0204673 A1 10/2004 Flaherty et al.
2004/0220517 A1 11/2004 Starkweather et al.
2004/0225252 A1 11/2004 Gillespie et al.
2004/0225409 A1 11/2004 Duncan et al.
2004/0232219 A1 11/2004 Fowler
2004/0247445 A1 12/2004 Nelson et al.
2004/0253123 A1 12/2004 Xie et al.
2004/0254434 A1 12/2004 Goodnow et al.
2004/0254513 A1 12/2004 Shang et al.
2005/0021006 A1 1/2005 Tonnies
2005/0021297 A1 1/2005 Hartlaub
2005/0022274 A1 1/2005 Campbell et al.
2005/0038680 A1 2/2005 McMahon
2005/0055242 A1 3/2005 Bello et al.
2005/0055244 A1 3/2005 Mullan et al.
2005/0065465 A1 3/2005 Lebel et al.
2005/0075544 A1 4/2005 Shapiro et al.
2005/0096593 A1 5/2005 Pope et al.
2005/0099624 A1 5/2005 Staehr
2005/0107923 A1 5/2005 Vanderveen
2005/0119914 A1 6/2005 Batch
2005/0131739 A1 6/2005 Rabinowitz et al.
2005/0137522 A1 6/2005 Aoki
2005/0143864 A1 6/2005 Blomquist
2005/0145010 A1 7/2005 Vanderveen et al.
2005/0171503 A1 8/2005 Van Den Berghe et al.
2005/0171815 A1 8/2005 Vanderveen
2005/0177045 A1 8/2005 Degertekin et al.
2005/0177096 A1 8/2005 Bollish et al.
2005/0182306 A1 8/2005 Sloan
2005/0182355 A1 8/2005 Bui
2005/0182366 A1 8/2005 Vogt et al.
2005/0187515 A1 8/2005 Varrichio et al.
2005/0192529 A1 9/2005 Butterfield et al.
2005/0192557 A1 9/2005 Brauker et al.
2005/0197554 A1 9/2005 Polcha
2005/0197621 A1 9/2005 Poulsen et al.
2005/0209563 A1 9/2005 Hopping et al.
2005/0209793 A1 9/2005 Yamada
2005/0224083 A1 10/2005 Crass
2005/0235732 A1 10/2005 Rush
2005/0235733 A1 10/2005 Holst et al.
2005/0238497 A1 10/2005 Holst et al.
2005/0238506 A1 10/2005 Mescher et al.
2005/0240305 A1 10/2005 Bogash et al.
2005/0273059 A1 12/2005 Mernoe et al.
2005/0277890 A1 12/2005 Stewart et al.
2005/0279419 A1 12/2005 Tribble et al.
2006/0002799 A1 1/2006 Schann et al.
2006/0009727 A1 1/2006 O'Mahony et al.
2006/0009734 A1 1/2006 Martin
2006/0042633 A1 3/2006 Bishop et al.
2006/0047270 A1 3/2006 Shelton
2006/0053036 A1 3/2006 Coffman et al.
2006/0064020 A1 3/2006 Burnes et al.
2006/0064053 A1 3/2006 Bollish et al.
2006/0079768 A1 4/2006 Small et al.
2006/0079831 A1 4/2006 Gilbert
2006/0100746 A1 5/2006 Leibner-Druska
2006/0100907 A1 5/2006 Holland et al.
2006/0106649 A1 5/2006 Eggers et al.
2006/0116639 A1 6/2006 Russell
2006/0117856 A1 6/2006 Orr et al.
2006/0117867 A1 6/2006 Froehlich et al.
2006/0122867 A1 6/2006 Eggers et al.
2006/0135939 A1 6/2006 Brown
2006/0135940 A1 6/2006 Joshi
2006/0136271 A1 6/2006 Eggers et al.
2006/0140798 A1 6/2006 Kutsuzawa
2006/0143051 A1 6/2006 Eggers et al.
2006/0173260 A1 8/2006 Gaoni et al.
2006/0173406 A1 8/2006 Hayes et al.
2006/0180916 A1 8/2006 Wyland
2006/0181695 A1 8/2006 Sage, Jr.
2006/0187069 A1 8/2006 Duan
2006/0190302 A1 8/2006 Eggers et al.
2006/0195022 A1 8/2006 Trepagnier et al.
2006/0200007 A1 9/2006 Brockway et al.

(56) References Cited

U.S. PATENT DOCUMENTS

2006/0200369 A1 9/2006 Batch et al.
2006/0211404 A1 9/2006 Cromp et al.
2006/0224141 A1 10/2006 Rush et al.
2006/0224181 A1 10/2006 McEwen et al.
2006/0226088 A1 10/2006 Robinson et al.
2006/0226089 A1 10/2006 Robinson et al.
2006/0226090 A1 10/2006 Robinson et al.
2006/0229557 A1 10/2006 Fathallah et al.
2006/0229918 A1 10/2006 Fotsch et al.
2006/0235353 A1 10/2006 Gelfand et al.
2006/0258985 A1 11/2006 Russell
2006/0260416 A1 11/2006 Sage et al.
2006/0264895 A1 11/2006 Flanders
2006/0265246 A1 11/2006 Hoag
2006/0266128 A1 11/2006 Clark et al.
2006/0270971 A1 11/2006 Gelfand et al.
2006/0271286 A1 11/2006 Rosenberg
2006/0272421 A1 12/2006 Frinak et al.
2006/0275142 A1 12/2006 Bouton et al.
2007/0015972 A1 1/2007 Wang et al.
2007/0060796 A1 3/2007 Kim
2007/0060871 A1 3/2007 Istoc
2007/0060872 A1 3/2007 Hall et al.
2007/0060874 A1 3/2007 Nesbitt et al.
2007/0062250 A1 3/2007 Krulevitch et al.
2007/0065363 A1 3/2007 Dalal et al.
2007/0078314 A1 4/2007 Grounsell
2007/0083152 A1 4/2007 Williams, Jr. et al.
2007/0084288 A1 4/2007 Thomas et al.
2007/0088333 A1 4/2007 Levin et al.
2007/0093753 A1* 4/2007 Krulevitch ........ A61M 5/16831
604/131
2007/0100222 A1 5/2007 Mastrototaro et al.
2007/0100665 A1 5/2007 Brown
2007/0112298 A1 5/2007 Mueller et al.
2007/0118405 A1 5/2007 Campbell et al.
2007/0129618 A1 6/2007 Goldberger et al.
2007/0142822 A1 6/2007 Remde
2007/0156452 A1 7/2007 Batch
2007/0179436 A1 8/2007 Braig et al.
2007/0191817 A1 8/2007 Martin
2007/0214003 A1 9/2007 Holland et al.
2007/0215545 A1 9/2007 Bissler et al.
2007/0233035 A1 10/2007 Wehba et al.
2007/0233049 A1 10/2007 Wehba et al.
2007/0240497 A1 10/2007 Robinson et al.
2007/0255250 A1 11/2007 Moberg et al.
2007/0257788 A1 11/2007 Carlson
2007/0267945 A1 11/2007 Sudol
2007/0270747 A1 11/2007 Remde
2007/0274843 A1 11/2007 Vanderveen et al.
2007/0289384 A1 12/2007 Sakai et al.
2008/0009684 A1 1/2008 Corsetti et al.
2008/0028868 A1 2/2008 Konzelmann et al.
2008/0033361 A1 2/2008 Evans et al.
2008/0039777 A1 2/2008 Katz et al.
2008/0048211 A1 2/2008 Khuri-Yakub et al.
2008/0058773 A1 3/2008 John
2008/0060448 A1 3/2008 Wiest et al.
2008/0065420 A1 3/2008 Tirinato et al.
2008/0071210 A1 3/2008 Moubayed et al.
2008/0071496 A1 3/2008 Glascock
2008/0071580 A1 3/2008 Marcus et al.
2008/0091466 A1 4/2008 Butler et al.
2008/0097288 A1 4/2008 Levin et al.
2008/0097289 A1 4/2008 Steil et al.
2008/0097317 A1 4/2008 Alholm et al.
2008/0098798 A1 5/2008 Riley et al.
2008/0119822 A1 5/2008 Knauper
2008/0125701 A1 5/2008 Moberg et al.
2008/0139907 A1 6/2008 Rao et al.
2008/0145249 A1 6/2008 Smisson
2008/0172030 A1 7/2008 Blomquist et al.
2008/0177254 A1 7/2008 Shelton et al.
2008/0184784 A1 8/2008 Dam
2008/0188789 A1 8/2008 Galavotti et al.
2008/0188796 A1 8/2008 Steil et al.
2008/0200870 A1 8/2008 Palmroos et al.
2008/0208484 A1 8/2008 Butterfield et al.
2008/0214919 A1 9/2008 Harmon et al.
2008/0221521 A1 9/2008 Getz et al.
2008/0221522 A1 9/2008 Moberg et al.
2008/0243055 A1 10/2008 Fathallah et al.
2008/0262469 A1 10/2008 Bristol et al.
2008/0269663 A1 10/2008 Arnold et al.
2008/0269714 A1 10/2008 Mastrototaro et al.
2008/0269723 A1 10/2008 Mastrototaro et al.
2008/0275384 A1 11/2008 Mastrototaro et al.
2008/0300572 A1 12/2008 Rankers et al.
2009/0001908 A1 1/2009 Shubinsky et al.
2009/0005703 A1 1/2009 Fasciano
2009/0006061 A1 1/2009 Thukral et al.
2009/0006129 A1 1/2009 Thukral
2009/0006133 A1 1/2009 Weinert
2009/0015824 A1 1/2009 Shubinsky et al.
2009/0043171 A1 2/2009 Rule
2009/0053071 A1 2/2009 Wang et al.
2009/0054743 A1 2/2009 Stewart
2009/0054754 A1 2/2009 McMahon et al.
2009/0069743 A1 3/2009 Krishnamoorthy et al.
2009/0077248 A1 3/2009 Castellucci et al.
2009/0082676 A1 3/2009 Bennison
2009/0088731 A1 4/2009 Campbell et al.
2009/0097029 A1 4/2009 Tokhtuev et al.
2009/0112155 A1 4/2009 Zhao
2009/0124963 A1 5/2009 Hogard et al.
2009/0124964 A1 5/2009 Leach et al.
2009/0131861 A1 5/2009 Braig et al.
2009/0135196 A1 5/2009 Holland et al.
2009/0143726 A1 6/2009 Bouton et al.
2009/0144025 A1 6/2009 Bouton et al.
2009/0144026 A1 6/2009 Bouton et al.
2009/0149743 A1 6/2009 Barron et al.
2009/0153058 A1 6/2009 Feng et al.
2009/0156922 A1 6/2009 Goldberger et al.
2009/0156975 A1 6/2009 Robinson et al.
2009/0177146 A1 7/2009 Nesbitt et al.
2009/0177188 A1 7/2009 Steinkogler
2009/0177248 A1 7/2009 Roberts
2009/0177769 A1 7/2009 Roberts
2009/0177992 A1 7/2009 Rubalcaba et al.
2009/0178485 A1 7/2009 Thomas et al.
2009/0183147 A1 7/2009 Davis et al.
2009/0192367 A1 7/2009 Braig et al.
2009/0205426 A1 8/2009 Balschat et al.
2009/0209938 A1 8/2009 Aalto-Setala
2009/0209945 A1 8/2009 Lobl et al.
2009/0212966 A1 8/2009 Panduro
2009/0221890 A1 9/2009 Saffer et al.
2009/0223294 A1 9/2009 Thomas et al.
2009/0227939 A1 9/2009 Memoe et al.
2009/0264720 A1 10/2009 Torjman et al.
2009/0270810 A1 10/2009 DeBelser
2009/0270833 A1 10/2009 DeBelser
2010/0022988 A1 1/2010 Wochner
2010/0280430 A1 1/2010 Caleffi et al.
2010/0036310 A1 2/2010 Hillman
2010/0056992 A1 3/2010 Hayter
2010/0069892 A1 3/2010 Steinbach et al.
2010/0077866 A1 4/2010 Graboi et al.
2010/0079760 A1 4/2010 Bernacki
2010/0094251 A1 4/2010 Estes et al.
2010/0106082 A1 4/2010 Zhou
2010/0121170 A1 5/2010 Rule
2010/0121415 A1 5/2010 Skelton et al.
2010/0130933 A1 5/2010 Holland et al.
2010/0131434 A1 5/2010 Magent et al.
2010/0141460 A1 6/2010 Tokhtuev et al.
2010/0147081 A1 6/2010 Thomas et al.
2010/0152554 A1 6/2010 Steine et al.
2010/0160854 A1 6/2010 Gauthier
2010/0168535 A1 7/2010 Robinson et al.
2010/0177375 A1 7/2010 Seyfried
2010/0185142 A1 7/2010 Kamen et al.

(56) References Cited

U.S. PATENT DOCUMENTS

2010/0198034 A1 8/2010 Thomas et al.
2010/0198182 A1 8/2010 Lanigan et al.
2010/0198183 A1 8/2010 Lanigan et al.
2010/0211002 A1 8/2010 Davis
2010/0212407 A1 8/2010 Stringham et al.
2010/0212675 A1 8/2010 Walling et al.
2010/0214110 A1 8/2010 Wang et al.
2010/0217154 A1 8/2010 Deshmukh et al.
2010/0217621 A1 8/2010 Schoenberg
2010/0271479 A1 10/2010 Heydlauf
2010/0273738 A1 10/2010 Valcke et al.
2010/0292634 A1 11/2010 Kircher
2010/0295686 A1 11/2010 Sloan et al.
2010/0298765 A1 11/2010 Budiman et al.
2010/0317093 A1 12/2010 Turewicz et al.
2010/0318025 A1 12/2010 John
2011/0000560 A1 1/2011 Miller et al.
2011/0001605 A1 1/2011 Kiani et al.
2011/0004186 A1 1/2011 Butterfield
2011/0009797 A1 1/2011 Kelly et al.
2011/0028885 A1 2/2011 Eggers et al.
2011/0040247 A1 2/2011 Mandro et al.
2011/0046558 A1 2/2011 Gravesen et al.
2011/0062703 A1 3/2011 Lopez et al.
2011/0064612 A1 3/2011 Franzoni et al.
2011/0071464 A1 3/2011 Palerm
2011/0072379 A1 3/2011 Gannon
2011/0077480 A1 3/2011 Bloom et al.
2011/0078608 A1 3/2011 Gannon et al.
2011/0099313 A1 4/2011 Bolanowski
2011/0105983 A1 5/2011 Kelly et al.
2011/0137241 A1 6/2011 DelCastilio et al.
2011/0144595 A1 6/2011 Cheng
2011/0160649 A1 6/2011 Pan
2011/0162647 A1 7/2011 Huby et al.
2011/0172918 A1 7/2011 Tome
2011/0175728 A1 7/2011 Baker, Jr.
2011/0190598 A1 8/2011 Shusterman
2011/0190694 A1 8/2011 Lanier et al.
2011/0264006 A1 10/2011 Ali et al.
2011/0264043 A1 10/2011 Kotnick et al.
2011/0282321 A1 11/2011 Steil et al.
2011/0320049 A1 12/2011 Chossat et al.
2012/0025995 A1 2/2012 Moberg et al.
2012/0035535 A1 2/2012 Johnson et al.
2012/0059234 A1 3/2012 Barrett et al.
2012/0068001 A1 3/2012 Pushkarsky et al.
2012/0095433 A1 4/2012 Hungerford et al.
2012/0123322 A1 5/2012 Scarpaci et al.
2012/0143116 A1 6/2012 Ware et al.
2012/0180790 A1 7/2012 Montgomery
2012/0185267 A1 7/2012 Kamen et al.
2012/0191059 A1 7/2012 Cummings et al.
2012/0194341 A1 8/2012 Peichel et al.
2012/0203177 A1 8/2012 Lanier
2012/0226350 A1 9/2012 Rudser et al.
2012/0245525 A1 9/2012 Pope et al.
2012/0259278 A1 10/2012 Hayes et al.
2013/0006666 A1 1/2013 Schneider
2013/0009551 A1 1/2013 Knapp
2013/0012917 A1 1/2013 Miller et al.
2013/0041342 A1 2/2013 Bernini et al.
2013/0083191 A1 4/2013 Lowery et al.
2013/0085443 A1 4/2013 Lowery et al.
2013/0085689 A1 4/2013 Sur et al.
2013/0110538 A1 5/2013 Butterfield et al.
2013/0150766 A1 6/2013 Olde et al.
2013/0150821 A1 6/2013 Bollish et al.
2013/0158504 A1 6/2013 Ruchti et al.
2013/0201482 A1 8/2013 Munro
2013/0116649 A1 9/2013 Kouyoumjian et al.
2013/0253430 A1 9/2013 Kouyoumjian et al.
2013/0291116 A1 10/2013 Homer
2013/0296823 A1 11/2013 Melker et al.
2013/0296984 A1 11/2013 Burnett et al.
2013/0318158 A1 11/2013 Teng et al.
2013/0345658 A1 12/2013 Browne et al.
2013/0345666 A1 12/2013 Panduro et al.
2014/0039446 A1 2/2014 Day
2014/0224829 A1 8/2014 Capone et al.
2014/0267563 A1 9/2014 Baca et al.
2014/0350513 A1 11/2014 Oruklu et al.
2014/0358077 A1 12/2014 Oruklu et al.
2015/0025453 A1 1/2015 Ledford et al.
2015/0033073 A1 1/2015 Yang et al.
2015/0168958 A1 6/2015 Downie et al.
2015/0246175 A1 9/2015 Shubinsky et al.
2015/0343141 A1 12/2015 Lindo et al.
2016/0042264 A1 2/2016 Borges et al.
2016/0103960 A1 4/2016 Hume et al.
2016/0110088 A1 4/2016 Vik et al.
2016/0151560 A1 6/2016 Toro et al.
2016/0151562 A1 6/2016 Magers et al.
2016/0175517 A1 6/2016 Sileika et al.
2016/0256622 A1 9/2016 Day et al.
2017/0043089 A1 2/2017 Handler
2018/0028749 A1 2/2018 Dumas, III et al.

FOREIGN PATENT DOCUMENTS

DE 34 35 647 7/1985
DE 35 30 747 3/1987
DE 37 20 664 1/1989
DE 38 27 444 2/1990
DE 197 34 002 9/1998
DE 199 01 078 2/2000
DE 198 40 965 3/2000
DE 198 44 252 3/2000
DE 199 32 147 1/2001
DE 102 49 238 5/2004
DE 103 52 456 7/2005
EP 0 282 323 9/1988
EP 0 291 727 11/1988
EP 0 319 272 6/1989
EP 0 319 275 6/1989
EP 0 335 385 10/1989
EP 0 337 092 10/1989
EP 0 341 582 11/1989
EP 0 370 162 5/1990
EP 0 387 724 9/1990
EP 0 429 866 6/1991
EP 0 441 323 8/1991
EP 0 453 211 10/1991
EP 0 462 405 12/1991
EP 0 501 234 9/1992
EP 0 516 130 12/1992
EP 0 519 765 12/1992
EP 0 643 301 3/1995
EP 0 683 465 11/1995
EP 0 431 310 1/1996
EP 0 589 439 8/1998
EP 0 880 936 12/1998
EP 0 954 090 11/1999
EP 0 960 627 12/1999
EP 1 174 817 1/2002
EP 1 177 802 2/2002
EP 1 197 178 4/2002
EP 1 500 025 4/2003
EP 1 813 188 8/2007
EP 2 062 527 5/2009
EP 2 228 004 9/2010
EP 2 243 506 10/2010
EP 2 381 260 10/2011
ES 254513 10/1981
FR 2 717 919 9/1995
GB 2 121 971 1/1984
GB 2 303 706 2/1997
GB 2 312 022 10/1997
GB 2 312 046 10/1997
JP 01-301118 12/1989
JP 01-308568 12/1989
JP 04-231966 8/1992
JP 07-289638 11/1995
JP 11-128344 5/1999

(56) References Cited

FOREIGN PATENT DOCUMENTS

| | | |
|---|---|---|
| JP | 2000-111374 | 4/2000 |
| JP | 2000-510575 | 8/2000 |
| JP | 2001-356034 | 12/2001 |
| JP | 2002-131105 | 5/2002 |
| JP | 2003-038642 | 2/2003 |
| JP | 2003-050144 | 2/2003 |
| JP | 2005-021463 | 1/2005 |
| JP | 2005-524081 | 3/2005 |
| JP | 2006-517423 | 7/2006 |
| JP | 2007-071695 | 3/2007 |
| JP | 2008-249400 | 10/2008 |
| JP | 4322661 | 6/2009 |
| WO | WO 84/000690 | 3/1984 |
| WO | WO 84/000894 | 3/1984 |
| WO | WO 90/007942 | 7/1990 |
| WO | WO 91/000113 | 1/1991 |
| WO | WO 91/016087 | 10/1991 |
| WO | WO 91/016416 | 10/1991 |
| WO | WO 93/004284 | 3/1993 |
| WO | WO 95/016200 | 6/1995 |
| WO | WO 95/031233 | 11/1995 |
| WO | WO 96/008755 | 3/1996 |
| WO | WO 96/025186 | 8/1996 |
| WO | WO 96/041156 | 12/1996 |
| WO | WO 97/010013 | 3/1997 |
| WO | WO 97/030333 | 8/1997 |
| WO | WO 98/004304 | 2/1998 |
| WO | WO 98/012670 | 3/1998 |
| WO | WO 98/014234 | 4/1998 |
| WO | WO 98/019263 | 5/1998 |
| WO | WO 98/044320 | 10/1998 |
| WO | WO 98/056441 | 12/1998 |
| WO | WO 99/015216 | 4/1999 |
| WO | WO 99/051003 | 10/1999 |
| WO | WO 99/052575 | 10/1999 |
| WO | WO 00/013580 | 3/2000 |
| WO | WO 00/013726 | 3/2000 |
| WO | WO 00/041621 | 7/2000 |
| WO | WO 01/014974 | 3/2001 |
| WO | WO 01/033484 | 5/2001 |
| WO | WO 01/033710 | 5/2001 |
| WO | WO 02/005702 | 1/2002 |
| WO | WO 02/009795 | 2/2002 |
| WO | WO 02/027276 | 4/2002 |
| WO | WO 02/066101 | 8/2002 |
| WO | WO 02/087664 | 11/2002 |
| WO | WO 03/006091 | 1/2003 |
| WO | WO 03/053498 | 7/2003 |
| WO | WO 03/093780 | 11/2003 |
| WO | WO 2004/035115 | 4/2004 |
| WO | WO 2004/060455 | 7/2004 |
| WO | WO 2004/112579 | 12/2004 |
| WO | WO 2005/018716 | 3/2005 |
| WO | WO 2005/030489 | 4/2005 |
| WO | WO 2005/036447 | 4/2005 |
| WO | WO 2005/050526 | 6/2005 |
| WO | WO 2005/057175 | 6/2005 |
| WO | WO 2005/065146 | 7/2005 |
| WO | WO 2005/065749 | 7/2005 |
| WO | WO 2005/082450 | 9/2005 |
| WO | WO 2005/118015 | 12/2005 |
| WO | WO 2006/016122 | 2/2006 |
| WO | WO 2006/022906 | 3/2006 |
| WO | WO 2007/000426 | 1/2007 |
| WO | WO 2007/033025 | 3/2007 |
| WO | WO 2007/035567 | 3/2007 |
| WO | WO 2007/087443 | 8/2007 |
| WO | WO 2008/004560 | 1/2008 |
| WO | WO 2008/053193 | 5/2008 |
| WO | WO 2008/059492 | 5/2008 |
| WO | WO 2008/063429 | 5/2008 |
| WO | WO 2008/067245 | 6/2008 |
| WO | WO 2008/088490 | 7/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/026420 | 2/2009 |
| WO | WO 2009/039203 | 3/2009 |
| WO | WO 2009/039214 | 3/2009 |
| WO | WO 2009/049252 | 4/2009 |
| WO | WO 2009/127683 | 10/2009 |
| WO | WO 2010/017279 | 2/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/135646 | 11/2010 |
| WO | WO 2010/135654 | 11/2010 |
| WO | WO 2010/135670 | 11/2010 |
| WO | WO 2010/135686 | 11/2010 |
| WO | WO 2010/148205 | 12/2010 |
| WO | WO 2011/017778 | 2/2011 |
| WO | WO 2011/080188 | 7/2011 |
| WO | WO 2011/109774 | 9/2011 |
| WO | WO 2012/042763 | 4/2012 |
| WO | WO 2013/028524 | 2/2013 |
| WO | WO 2013/096769 | 6/2013 |
| WO | WO 2015/134478 | 9/2015 |
| WO | WO 2017/051271 | 3/2017 |
| WO | WO 2017/197024 | 11/2017 |

OTHER PUBLICATIONS

Allegro, "3955—Full-Bridge PWM Microstepping Motor Drive", Datasheet, 1997, pp. 16.

Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.

Baxter, "Baxter Receives 510(k) Clearance for Next-Generation SIGMA Spectrum Infusion Pump with Master Drug Library" Press Release, May 8, 2014, pp. 2. http://web.archive.org/web/20160403140025/http://www.baxter.com/news-media/newsroom/press-releases/2014/05_08_14_sigma.page.

Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.

Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.

Binder et al., "Insulin Infusion with Parenteral Nutrition in Extremely Low Birth Weight Infants with Hyperglycemia", Journal of Pediatrics, Feb. 1989, vol. 114, No. 2, pp. 273-280.

Bode et al., "Intravenous Insulin Infusion Therapy: Indications, Methods, and Transition to Subcutaneous Insulin Therapy", Endocrine Practice, Mar./Apr. 2004, vol. 10, Supplement 2, pp. 71-80.

Cannon, MD et al., "Automated Heparin-Delivery System to Control Activated Partial Thromboplastin Time", Circulation, Feb. 16, 1999, vol. 99, pp. 751-756.

"CareAware® Infusion Management", Cerner Store, as printed May 12, 2011, pp. 3, https://store.cerner.com/items/7.

Chen et al., "Enabling Location-Based Services on Wireless LANs", The 11th IEEE International Conference on Networks, ICON 2003, Sep. 28-Oct. 1, 2003, pp. 567-572.

Cheung et al., "Hyperglycemia is Associated with Adverse Outcomes in Patients Receiving Total Parenteral Nutrition", Diabetes Care, Oct. 2005, vol. 28, No. 10, pp. 2367-2371.

Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.

Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.

(56) References Cited

OTHER PUBLICATIONS

Fogt et al., Development and Evaluation of a Glucose Analyzer for a Glucose-Controlled Insulin Infusion System (Biostator®), Clinical Chemistry, 1978, vol. 24, No. 8, pp. 1366-1372.
Goldberg et al., "Clinical Results of an Updated Insulin Infusion Protocol in Critically III Patients", Diabetes Spectrum, 2005, vol. 18, No. 3, pp. 188-191.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hospira, "Plum A+ ™ Infusion System" as archived Dec. 1, 2012, pp. 2. www.hospira.com/products_and_services/infusion_pumps/plum/index.
International Search Report and Written Opinion received in PCT Application No. PCT/US2013/034041, dated Jun. 19, 2013 in 11 pages.
Lamsdale et al., "A Usability Evaluation of an Infusion Pump by Nurses Using a Patient Simulator", Proceedings of the Human Factors and Ergonomics Society 49th Annual Meeting, Sep. 2005, pp. 1024-1028.
Magaji et al., "Inpatient Management of Hyperglycemia and Diabetes", Clinical Diabetes, 2011, vol. 29, No. 1, pp. 3-9.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
Maynard et al., "Subcutaneous Insulin Order Sets and Protocols: Effective Design and Implementation Strategies", Journal of Hospital Medicine, Sep./Oct. 2008, vol. 3, Issue 5, Supplement 5, pp. S29-S41.
Moghissi, Etie, MD, FACP, FACE, "Hyperglycemia in Hospitalized Patients", A Supplement to ACP Hospitalist, Jun. 15, 2008, pp. 32.
Nuckols et al., "Programmable Infusion Pumps in ICUs: An Analysis of Corresponding Adverse Drug Events", Journal of General Internal Medicine, 2007, vol. 23, Supp. 1, pp. 41-45.
Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
SGS-Thomson Microelectronics, "L6219—Stepper Motor Drive", Datasheet, Dec. 1996, pp. 10.
SGS-Thomson Microelectronics, "PBL3717A—Stepper Motor Drive", Datasheet, Apr. 1993, pp. 11.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Smith, Joe, "Infusion Pump Informatics", CatalyzeCare: Transforming Healthcare, as printed May 12, 2011, pp. 2.
Tang et al., "Linear Dimensionality Reduction Using Relevance Weighted LDA", Pattern Recognition, 2005, vol. 38, pp. 485-493, http://staff.ustc.edu.cn/~ketang/papers/TangSuganYaoQin_PR04.pdf.
Thomas et al., "Implementation of a Tight Glycaemic Control Protocol Using a Web-Based Insulin Dose Calculator", Anaesthesia, 2005, vol. 60, pp. 1093-1100.
Van Den Berghe, M.D., Ph.D., et al., "Intensive Insulin Therapy in Critically III Patients", The New England Journal of Medicine, Nov. 8, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.
Westbrook et al., "Errors in the Administration of Intravenous Medications in Hospital and the Role of Correct Procedures and Nurse Experience", BMJ Quality & Safety, 2011, vol. 20, pp. 1027-1034.
Zakariah et al., "Combination of Biphasic Transmittance Waveform with Blood Procalcitonin Levels for Diagnosis of Sepsis in Acutely III Patients", Critical Care Medicine, 2008, vol. 36, No. 5, pp. 1507-1512.
Alaris® Medical Systems, "Signature Edition® GOLD—Single & Dual Channel Infusion System", San Diego, CA, USA, date unknown, but believed to be at least as early as Nov. 29, 2008, pp. 70-74, 2-88 & 2-91.
Buhrdorf et al., "Capacitive Micromachined Ultrasonic Transducers and their Application", Proceedings of the IEEE Ultrasonics Symposium, Feb. 2001, vol. 2, pp. 933-940.
Coley et al., "Performance of Three Portable Infusion-Pump Devices Set to Deliver 2 mL/hr", American Journal of Health-System Pharmacy, Jun. 1, 1997, vol. 54, No. 11, pp. 1277-1280.
"Continually vs Continuously", https://web.archive.org/web/20090813092423/http://www.diffen.com/difference/Continually_vs_Continuously, as accessed Aug. 13, 2009 in 4 pages.
"CritiCore® Monitor: Critical Fluid Output and Core Bladder Temperature Monitor", BARD Urological Catheter Systems, Advertisement, 2005, pp. 2.
"Differential Pressure Transmitter, Series PD-39 X", SensorsOne Ltd., Advertisement, Dec. 2005, pp. 2.
Dunster et al., "Flow Continuity of Infusion Systems at Low Flow Rates", Anaesthesia and Intensive Care, Oct. 1995, vol. 23, No. 5, pp. 5.
"Froth", http://www.merriam-webster.com/dictionary/froth, as accessed May 13, 2015 in 1 page.
Hospira, "Plum XL™ Series Infusion System" Technical Service Manual, Feb. 2005, Lake Forest, Illinois, USA, pp. i-vii, 5-14, 8-3.
Ilfeld et al., "Delivery Rate Accuracy of Portable, Bolus-Capable Infusion Pumps Used for Patient-Controlled Continuous Regional Analgesia", Regional Anesthesia and Pain Medicine, Jan.-Feb. 2003, vol. 28, No. 1, pp. 17-23.
Ilfeld et al., "Portable Infusion Pumps Used for Continuous Regional Analgesia: Delivery Rate Accuracy and Consistency", Regional Anesthesia and Pain Medicine, Sep.-Oct. 2003, vol. 28, No. 5, pp. 424-432.
International Preliminary Report on Patentability and Written Opinion received in PCT Application No. PCT/US2013/034041, dated Oct. 9, 2014 in 10 pages.
JMS Co., Ltd., "Infusion Pump: OT-701", Tokyo, Japan, 2002, pp. 4.
Kutcher et al., "The Effect of Lighting Conditions on Caries Interpretation with a Laptop Computer in a Clinical Setting", Elsevier, Oct. 2006, vol. 102, No. 4, pp. 537-543.
Logan et al., "Fabricating Capacitive Micromachined Ultrasonic Transducers with a Novel Silicon-Nitride-Based Wafer Bonding Process", IEEE Transactions on Ultrasonics, Ferroelectrics, and Frequency Control, May 2009, vol. 56, No. 5, pp. 1074-1084.
Merry et al., "A New, Safety-Oriented, Integrated Drug Administration and Automated Anesthesia Record System", Anesthesia & Analgesia, Aug. 2001, vol. 93, No. 2 pp. 385-390.
Microchip Technology Inc., "MTA11200B; TrueGauge™ Intelligent Battery Management I.C.", https://www.elektronik.ropla.eu/pdf/stock/mcp/mta11200b.pdf, 1995, pp. 44.

* cited by examiner

AIR DETECTION SYSTEM AND METHOD FOR DETECTING AIR IN A PUMP OF AN INFUSION SYSTEM

BACKGROUND OF THE INVENTION

Field of the Invention

The disclosure relates to systems and methods for detecting air in an infusion system.

Description of the Related Art

Existing systems and methods for detecting air in the line of an infusion device generally involve the use of ultrasonic sensors that detect the open circuit caused when air fills the volume between two sensor pairs. When the air sensor signal moves beyond a pre-defined air/fluid threshold, an alarm condition occurs and IV infusion is paused. Unfortunately, a variety of situations exist which either mask the presence of air, leading to false negatives, or generate false alarms. Fundamentally, this problem occurs because a single sensor with a univariate signal is applied to a relatively complex problem with multiple dimensions.

A system and method is needed which more accurately detects air in the line of an infusion device.

SUMMARY OF THE INVENTION

In one embodiment of the disclosure, a method for detecting air in a chamber of an infusion system is disclosed. In one step, a plunger is moved against a chamber containing fluid with an actuator device. In another step, a force acting on the plunger, as it moves against the chamber, is detected with a sensor. In an additional step, a measurement of the force acting on the plunger is electronically communicated from the sensor to a processor. In yet another step, a determination is made, with the processor, that the chamber contains air when: (1) a trigger event occurs in which a change in the force exceeds a threshold; and (2) subsequent to the trigger event a differential between a baseline average force acting on the plunger and a current average force acting on the plunger exceeds an expected force differential within a defined delay range.

In another embodiment of the disclosure, a method for detecting air in a chamber of an infusion system is disclosed. In one step, a plunger is moved against a chamber containing fluid with an actuator device. In another step, a force acting on the plunger, as it moves against the chamber, is detected with a sensor. In an additional step, a measurement of the force acting on the plunger is electronically communicated from the sensor to a processor. In yet another step, the processor is used to determine: (1) a baseline force profile; (2) a current force profile representing the current force acting on the plunger against the chamber; (3) a difference between the current force profile and the baseline force profile; and (4) that the chamber contains air when the calculated difference crosses a threshold.

In still another embodiment of the disclosure, a method for detecting air in a chamber of an infusion system is disclosed. In one step, a plunger is moved against a chamber containing fluid using an actuator device. In another step, a force acting on the plunger, as it moves against the chamber, is detected with a sensor. In yet another step, a measurement of the force acting on the plunger is electronically communicated from the sensor to a processor. In another step, the processor is used to: (1) preprocess a force profile detected by the sensor; (2) extract features from the force profile; and (3) classify the force profile as being an air force profile or a liquid force profile based on the extracted features of the force profile.

These and other features, aspects and advantages of the disclosure will become better understood with reference to the following drawings, description and claims.

DETAILED DESCRIPTION OF THE PREFERRED EMBODIMENT

Figure 1:
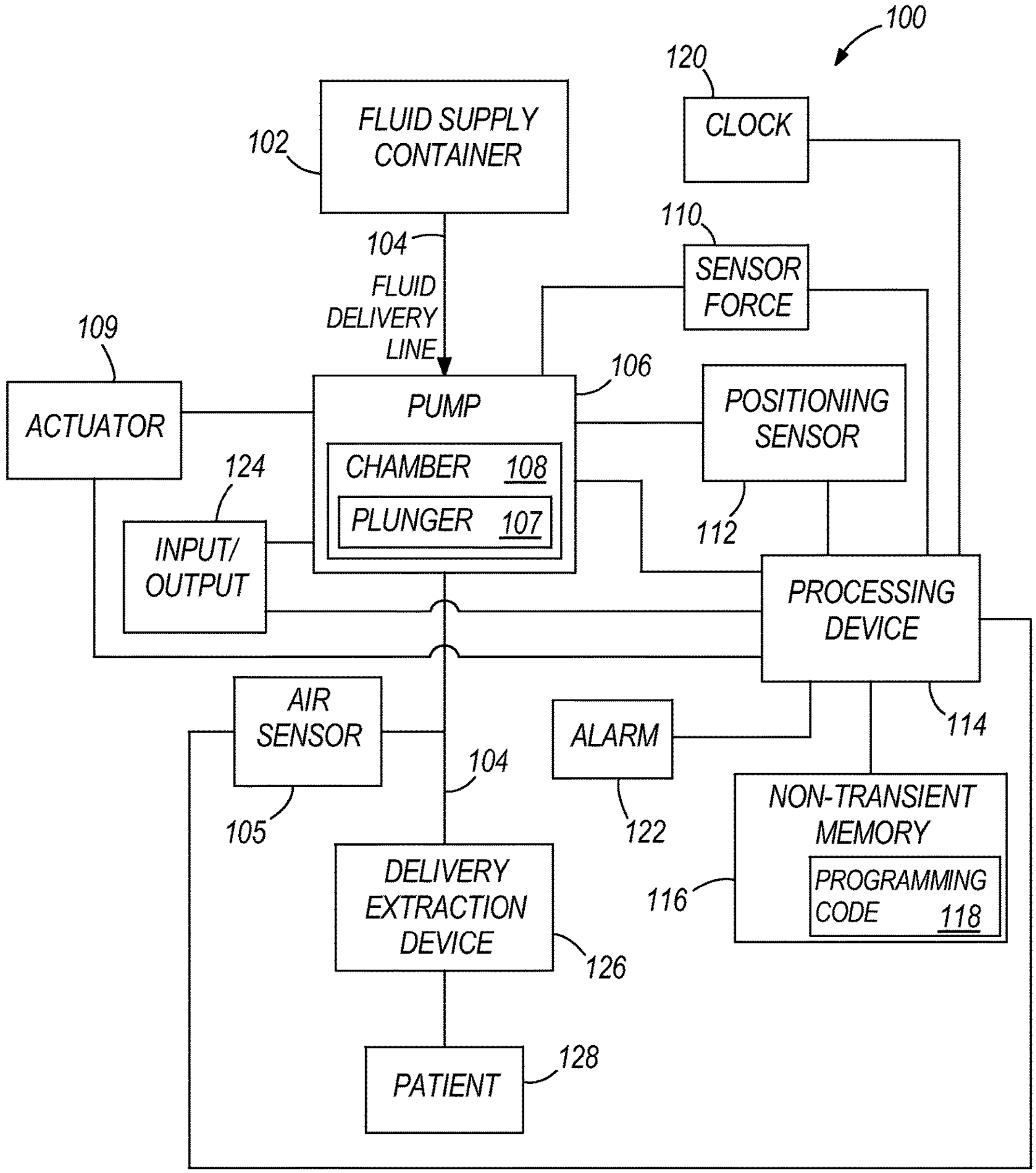
FIG. 1 illustrates a block diagram of a drug delivery infusion system under one embodiment of the disclosure.

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims. It is noted that the Figures are purely for illustrative purposes and are not to scale.

The instant disclosure provides methods and apparatus for determining whether air is present in an infusion system. Several types of pumps, such as Symbig™ Plum™, and Gemstar™ pumps sold by Hospira, Inc., involve the use of a cassette with a chamber that is compressed by an actuated plunger to pump fluid at a controlled rate from the drug container to the patient. The chamber is surrounded by valves which open and close in a complimentary manner to ensure unidirectional flow. The measured force during a pumping cycle is directly related to the type of fluid in the chamber. Fluids are relatively incompressible and generate a higher and different force profile than air. Similarly, a combination of fluid and air in the chamber results in a hybrid shape profile which is indicative of the mixture percentages of both fluid and air. The instant disclosure discloses algorithms for utilizing the plunger force to detect the presence of air in the chamber to detect an air embolism prior to its infusion into a patient.

In one embodiment of the disclosure, an event detection algorithm is disclosed which determines a change from fluid to air in the pumping chamber on the basis of a change in the average force exerted against the plunger. The algorithm utilizes a derivative spike for event detection and a systematic reduction in the average force to confirm the nature of the change.

In another embodiment of the disclosure, a pattern recognition system/method is provided for recognizing fluid, air, or a mixture thereof in a pumping chamber. The system normalizes the force signal/profile acting on the plunger against the chamber to a baseline. The system then preprocesses the force signal/profile to smooth and re-samples the x-axis to a standard sampling interval with respect to plunger position. The system then extracts features such as the maximum absolute difference between the baseline and each subsequent force profile, or other types of features. The system then classifies the force profile as being air, fluid, or a combination thereof using linear discriminate analysis or another type of analysis system/method.

In still another embodiment of the disclosure, a varied pattern recognition system/method is provided for recognizing fluid, air, or a mixture thereof in a pumping chamber. The system, without normalizing to a baseline, preprocesses the force signal/profile acting on the plunger against the chamber by applying a low pass filter or by applying another type of preprocessing system/method. The system then extracts features from the entire force profile or a subset thereof such as the signal frequency content, the signal phase, the standard deviation or variance, the maximum, the range, the plunger position of critical points, the scores based on a principal component analysis, or extracts other types of features. The system then classifies the force profile as being air, fluid, or a combination thereof using linear discriminate analysis, k-nearest neighbor, support vector machines, or another type of analysis system/method.

One or more systems/methods of the disclosure include components that are optimized/customized according to a delivery rate of the fluid within the pumping chamber. Some of the existing algorithms fail to account for the profound impact of delivery rate on the observed plunger sensor force profile and the detection electronics. One or more systems/methods of the disclosure provide normalization or clustering states that reduce this impact and thereby improve sensitivity.

One or more systems/methods of the disclosure may be combined with any existing systems/methods for detecting air in an infusion system to improve the reliability of air detection systems. For instance, many current systems/methods use acoustic or ultrasonic sensors to detect the presence of air in tubing segments. However, these systems/methods often do not consider the possibility of an acoustic short circuit or a bubble that is stuck or repetitively passes in front of the sensor. Many systems/methods rely on a single air ultrasonic sensor with a fixed threshold which separates the air sensor signal into two regions representing air and fluid. When a voltage is measured that is within the air signal region, the volume of air represented by the signal is accumulated until an alarm condition is met. The disclosure allows for the combination of the output of a force sensor signal with one or more air sensors to improve the reliability of existing air detection systems/methods. In doing so, the disclosed system/method does not require additional hardware modifications but instead leverages the acquired force signal. Additionally, the disclosure does not necessarily require the replacement of existing software modules for air detection but adds an additional safety and/or reliability layer to improve the robustness of existing air detection systems and methods.

FIG. 1 illustrates a block diagram of a drug delivery infusion system 100 under one embodiment of the disclosure. The drug delivery infusion system 100 comprises: a fluid supply container 102; a fluid delivery line 104; an air sensor 105 connected to the fluid delivery line 104; a pump 106 comprising a plunger 107 moveably disposed against a chamber 108; an actuator device 109; a sensor 110; a positional sensor 112; a processing device 114; a nontransient memory 116 storing programming code 118; a clock 120; an alarm 122; an input/output device 124; and a delivery/extraction device 126. The drug delivery infusion system 100 may comprise a drug delivery infusion system such as the Plum A+™, Gemstar™, Symbig™, or other type of drug delivery infusion system. The fluid supply container 102 comprises a container for delivering fluid such as IV fluid or a drug to the patient 128 through the chamber 108 due to movement of the plunger 107 against the chamber 108. The fluid delivery line 104 comprises one or more tubes, connected between the fluid supply container 102, the pump 106, and the delivery/extraction device 126, for transporting fluid from the fluid supply container 102, through the pump 106, through the delivery/extraction device 126 to the patient 128. The fluid delivery line 104 may also be used to transport blood, extracted from the patient 128 using the delivery/extraction device 126, as a result of a pumping action of the pump 106. The pump 106 comprises a pump for pumping fluid from the supply container 102 or for pumping blood from the patient 128.

The pump 106 may comprise a plunger based pump, a peristaltic pump, or another type of pump. The chamber 108 comprises an inner cavity of the pump 106 into which fluid from the fluid supply container 102 is pumped into and through due to the moveably disposed plunger 107 moving against the chamber 108 as a result of the actuator device 109. The actuator device 109 may comprise a motor or another type of actuating device for moving the plunger 107 against the chamber 108. The sensor 110 is contained within the chamber 108 and detects the force acting on the plunger 107 as it moves against the chamber 108. The sensor 110 may comprise a force sensor signal comprising a pressure sensor, an elastic column, a strain gauge, or a piezoelectric crystal force transducer. The positional sensor 112 is used to determine a position of the plunger 107 against the chamber 108. The positional sensor 112 may comprise an encoder or may utilize the expected position based upon the commands sent to the actuator.

The processing device 114 is in electronic communication with the pump 106, the actuator device 109, the sensor 110, the positional sensor 112, the non-transient memory 116 storing the programming code 118, the clock 120, the alarm 122, and the input/output device 124. The processing device 114 comprises a processor for processing information received from the pump 106, the sensor 110, the positional sensor 112, and the clock 120, and for executing a software algorithm, contained in the programming code 118 stored in the nontransient memory 116, to determine if air, liquid (fluid), or a combination thereof is located in the chamber 108 of the pump 106. The non-transient memory 116 may be located within or outside of the processing device 114.

The clock 120 keeps time of activities of the drug delivery infusion system 100 including the plunger 107, the sensor 110, the positional sensor 112, and its other components. The alarm 122, when triggered by the processing device 114, is configured to notify the clinician as to the presence of air in the chamber 108, and to stop the pump 106 prior to an air embolism being delivered through the fluid delivery line 104 and the delivery/extraction device 126 to the patient 128. The input/output device 124 comprises a device which allows a clinician to input information, such as a user-inputted medication infusion program, to the processing device 114, and which also outputs information to the clinician. The delivery/extraction device 126 comprises a patient vascular access point device for delivering fluid from the fluid supply container 102 to the patient 128, or for extracting blood from the patient 128. The delivery/extraction device 126 may comprise a needle, a catheter, or another type of delivery/extraction device.

In one embodiment of the disclosure, the drug delivery infusion system 100 of FIG. 1 may determine when air is present in the chamber 108 by analyzing the force on the plunger 107 and the derivative of the force acting on the plunger 107 per delivered volume of the fluid or air exiting the chamber 108. This is because it has been discovered that when air reaches the chamber 108, the derivative force acting on the plunger 107 per the delivered volume of the fluid exiting the chamber 108 spikes in the downward direction and then returns to a baseline value, and that the average force on the plunger 107 then proceeds to drop slightly as the chamber 108 fills with air. To process this information, six data points per cycle of the plunger 107 may be gathered. In other embodiments, a varying number of data points per cycle of the plunger 107 may be gathered.

Figure 2:
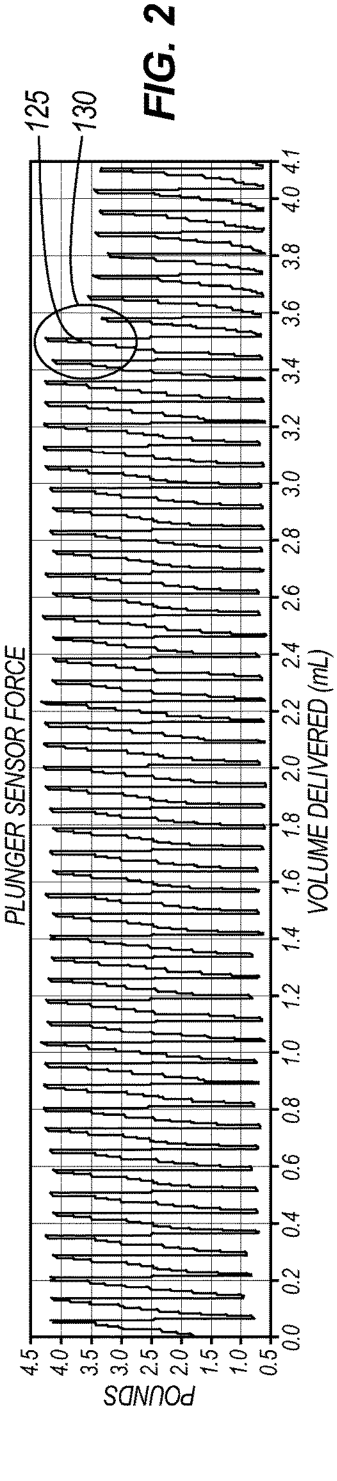
FIG. 2 illustrates a graph plotting a plunger sensor force curve per volume of fluid delivered.
Figure 3:
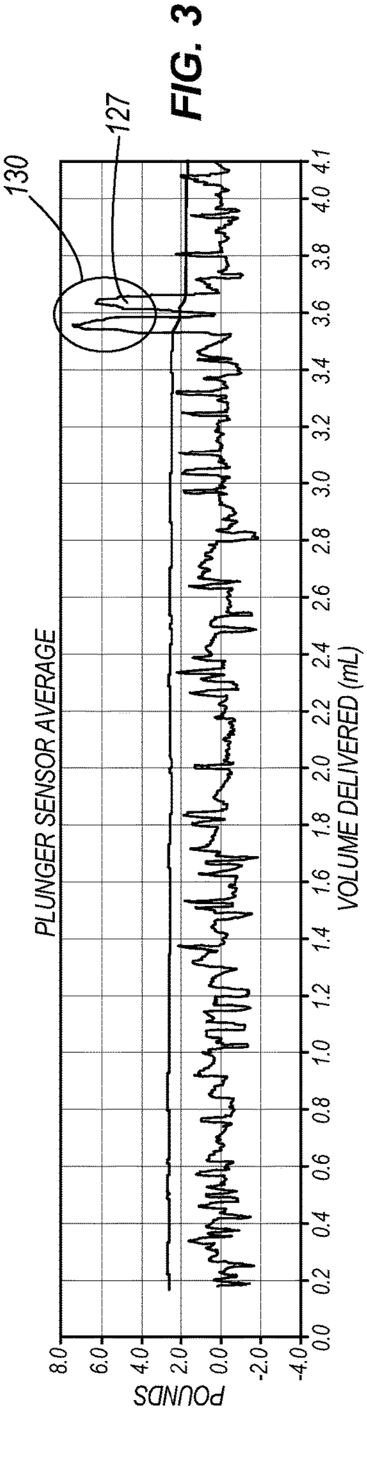
FIG. 3 illustrates a corresponding graph to FIG. 2 plotting a plunger sensor force negative derivative curve per volume of fluid delivered.
Figure 4:
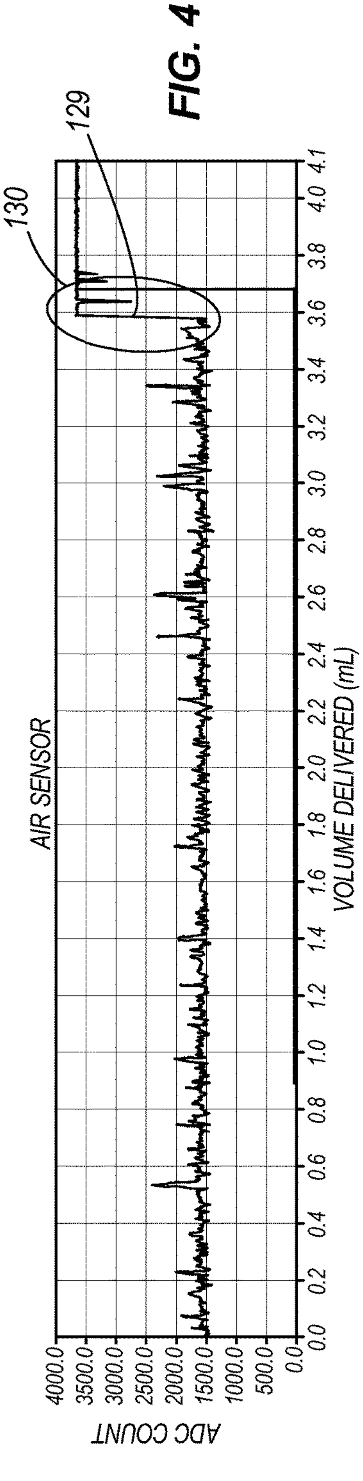
FIG. 4 illustrates a corresponding graph to FIGS. 2 and 3 plotting an in-line sensor ADC curve per volume of fluid delivered.

Corresponding FIGS. 2-4 illustrate typical data for one embodiment of a single iteration and end-of-bag event in which air is discovered in the chamber of FIG. 1. FIG. 2 illustrates a graph plotting a plunger sensor force curve 125 per volume of fluid delivered. The Y-axis represents pounds of force on the plunger detected by a plunger force sensor and the X-axis represents volume in milliliters of the fluid delivered from the chamber. FIG. 3 illustrates a corresponding graph to FIG. 2 plotting a plunger sensor force negative derivative curve 127 per volume of fluid delivered. The Y-axis represents a derivative of the average force on the plunger of FIG. 2 in pounds per unit volume and the X-axis represents volume in milliliters of the fluid delivered from the chamber. FIG. 4 illustrates a corresponding graph to FIGS. 2 and 3 plotting an in-line air sensor ADC curve 129 per volume of fluid delivered. The Y-axis represents an ADC count (also referred to as Analog-to-Digital-Count) of the fluid in-line as detected by an air sensor and the X-axis represents volume in milliliters of the fluid delivered from the chamber. As illustrated by FIG. 3, the transition from fluid to air occurs at the point in volume where the derivative of the force on the plunger spikes at location 130. As illustrated by FIG. 2, the force on the plunger drops at this same location 130. As illustrated by FIG. 4, the ADC count dramatically increases at this same location 130.

Figure 5:
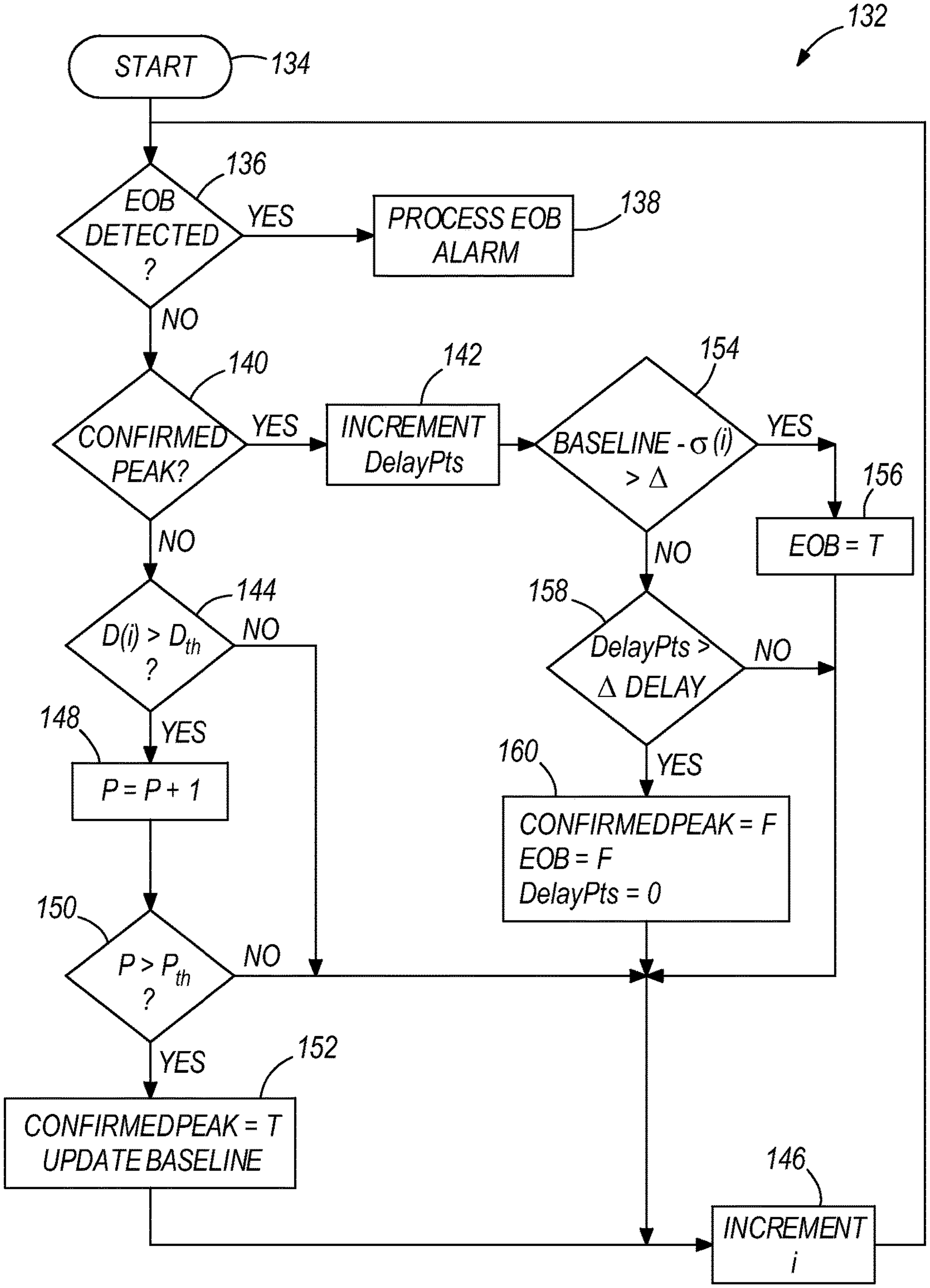
FIG. 5 illustrates one embodiment of a method, comprising a continuous flow chart, under the disclosure for determining whether air is contained in a chamber of a pump.

FIG. 5 illustrates one embodiment of a method 132, comprising a continuous flow chart, under the disclosure for determining whether air is contained in a chamber of a pump. The method 132 may be implemented using the drug delivery infusion system 100 of FIG. 1 with the plunger being moved with the actuator device against the chamber containing fluid, the sensor detecting a force acting on the plunger as it moves against the chamber, the processor processing the force measurements taken by the sensor and implementing programming code stored in a non-transient memory in order to determine whether air is contained in the chamber using the algorithm set forth in method 132, and the alarm being turned on if the processor determines that air is contained in the chamber which may trigger the pump being shut down. Moreover, the method 132 may utilize the clock of the drug delivery infusion system 100 of FIG. 1 to keep time of activities of the plunger or the sensor, and may use the positional sensor to determine a position of the plunger. In other embodiments, the method 132 may utilize varying components to implement the method.

In step 134, the method starts. After step 134, in step 136 a determination is made as to whether the end-of-bag (EOB), or equivalent situation in which the chamber contains air, has been detected. If the answer to the determination in step 136 is 'yes' and the end of the bag has been detected, the method proceeds to step 138 and an end-of-bag alarm is turned on to indicate that air is in the chamber. This end-of-bag (EOB) event may pause the pump infusion or be used by another algorithm to qualify an air-in-line alarm. If the answer to the determination in step 136 is 'no' and the end of the bag has not been detected, the method proceeds to step 140 in which a determination is made as to whether there is a previously confirmed peak. If the answer to the determination in step 140 is 'yes' and there is a confirmed peak, the method proceeds to step 142 which is discussed more thoroughly below. If the answer to the determination in step 140 is 'no' and there is not a previously confirmed peak, the method proceeds to step 144 in which a determination is made as to whether a trigger event has occurred in which the current negative derivative (of the average force) D(i) of the force of the plunger per delivered volume of the fluid exiting the chamber exceeds a derivative threshold Dih which indicates the beginning of a possible end-of-bag (EOB) event signifying that air may have entered the chamber. It should be noted that variable i is initially set to 1. The derivative threshold Dih is flow dependent. The derivative threshold Dih may be set to 1.5 for a flow rate of the fluid below 200 milliliters per hour and to 3.0 for a flow rate of the fluid above 200 milliliters per hour. In other embodiments, the derivative threshold Dih may be varied as a direct function of flow rate.

If the answer to the determination in step 144 is 'no,' the method proceeds to step 146, increments variable i using the equation i=i+1, and then proceeds back to and repeats step 136. If the answer to the determination in step 144 is 'yes,' the method proceeds to step 148 and increments variable P applying using the equation P=P+1. It should be noted that variable P is initially set to 0. After step 148, the method proceeds to step 150 in which a determination is made as to whether variable P is greater than the consecutive point threshold Pih. In one embodiment, the consecutive point threshold Pih is set to 1. In other embodiments, the consecutive point threshold Pih may be varied. The consecutive point threshold Pih represents one less than the number of consecutive points P that the current negative derivative (average) D(i) of the force of the plunger versus volume of the fluid delivered must exceed a derivative threshold D1*h* in order to indicate a possible end-of-bag (EOB) event signifying that air may be in the chamber. If the answer to the determination in step 150 is 'no,' the method proceeds to step 146, increments i applying the equation i=i+1, and then proceeds back to and repeats step 136. If the answer to the determination in step 150 is 'yes,' the method proceeds to step 152 in which the peak is confirmed, and a baseline B is taken.

The baseline B represents the average force during infusion when the chamber is filled with fluid. In one embodiment, the baseline B comprises the average force acting on the plunger over a defined baseline range occurring up to the trigger event. In one embodiment, the defined baseline range comprises the immediately previous 100 micro liters of average force data on the plunger taken immediately previous and up to the trigger event. In one embodiment, the baseline range may comprise multiple cycles of average force data. In other embodiments, the baseline range may vary. The trigger event comprises the point at which the negative derivative force D(i) acting on the plunger per the delivered volume of the fluid exiting the chamber first exceeds the derivative threshold D1*h* so long as subsequently the number of consecutive measured points P of the cycle of the plunger from the trigger event, in which the negative derivative force D(i) acting on the plunger per the delivered volume of the fluid exiting the chamber continues to exceed the derivative threshold D1*h*, exceeds the consecutive point threshold Pih. In other embodiments, the trigger event may vary. After step 152, the method proceeds to step 146, increments variable i using the equation i=i+1, and then proceeds back to and repeats step 136.

As referred to earlier, if the answer to the determination in step 140 is 'yes' and there is a confirmed peak, the method proceeds to step 142 and increments the delay points DP using the equation delay points=delay points+1. The delay points are initially set to zero. The delay points represent the number of data points taken of the cycle of the plunger since the confirmed peak. After step 142, the method proceeds to step 154 and makes a determination as to whether the differential between the baseline B and the current average force σ(i) is greater than the expected force differential Δ. The current average force σ(i) comprises the current average force on the plunger taken over a certain number of points of the cycle up to the current point of the plunger. In one embodiment, the current average force on the plunger may be calculated based on two cycles of the plunger immediately preceding and up to the current point of the plunger. In other embodiments, the current average force on the plunger may be taken over a varied range. In one embodiment, the expected force differential Δ comprises 0.15 pounds of force. In other embodiments, the expected force differential Δ may vary.

If the answer to the determination in step 154 is 'yes,' the method proceeds to step 156, confirms that an end-of-bag (EOB) or equivalent event has occurred, and proceeds through steps 146, 136, and 138 to turn on the end-of-bag alarm to indicate that air is in the chamber. This end-of-bag (EOB) event may turn off the pump. If the answer to the determination in step 154 is 'no,' the method proceeds to step 158 and makes a determination as to whether the delay points DP is greater than a Δ delay point threshold. The Δ delay point threshold comprises a defined delay range, starting from the point of the trigger event, over which the differential between the baseline B and the current average force σ(i) must exceed the expected force differential Δ in order to determine that an end-of-bag (EOB) event has occurred. In one embodiment, the Δ delay point threshold comprises 200 micro liters of delivered fluid. In other embodiments, the Δ delay point threshold may vary.

If the answer to the determination in step 158 is 'no,' the method proceeds to step 146, increments variable i using the equation i=i+1, and then proceeds back to and repeats step 136. If the answer to the determination in step 158 is 'yes,' the method proceeds to step 160, determines that there is no confirmed peak, determines that there is no end-of-bag (EOB) event, resets the delay points DP to zero, proceeds to step 146, increments variable i using the equation i=i+1, and then proceeds back to and repeats step 136. In other embodiments, one or more steps of the method 132 may be modified, not followed, or one or more additional steps may be added. Moreover, any of the variables of method 132 may be either user set, using an input device, or preset into the processor.

Figure 6:
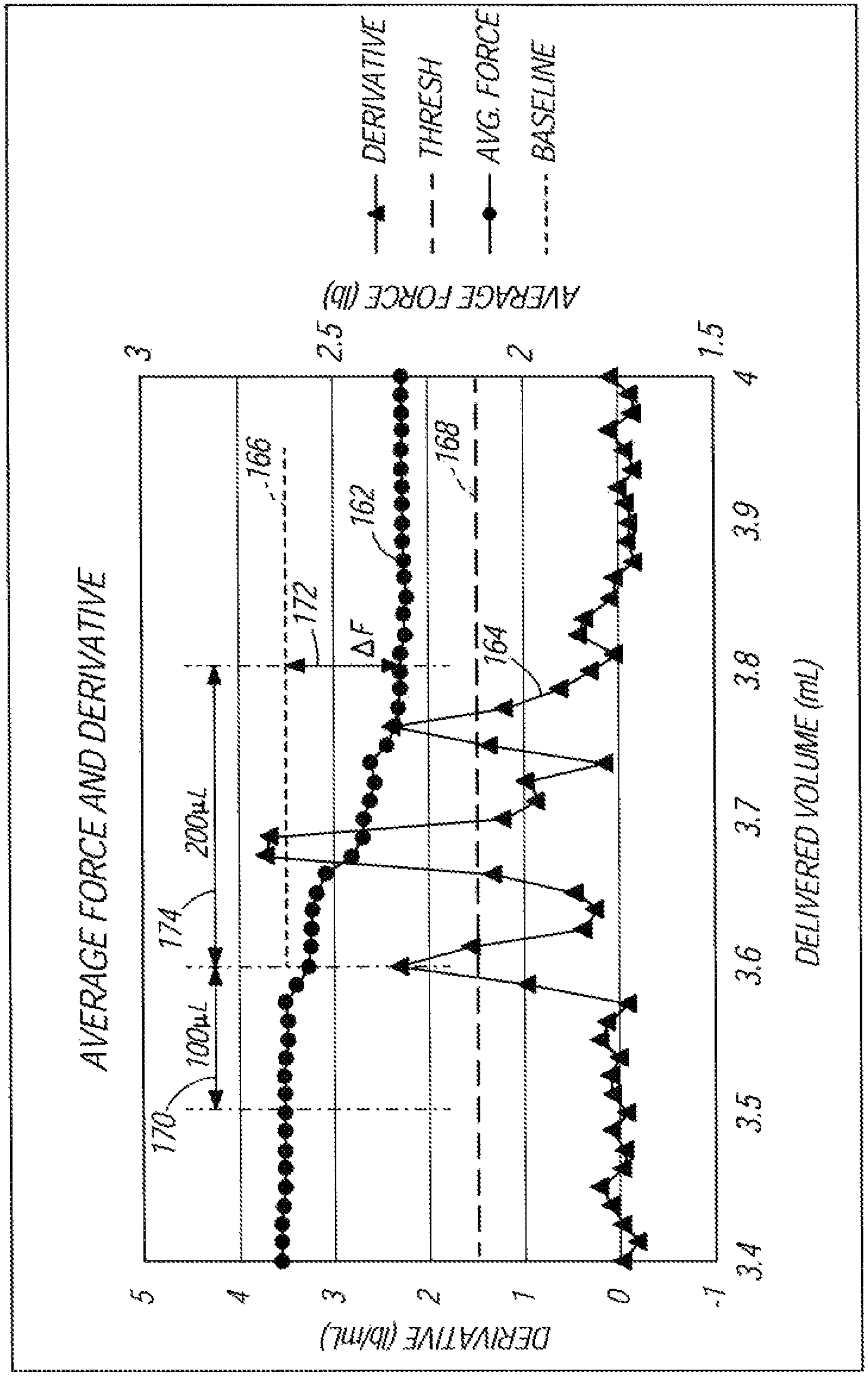
FIG. 6 illustrates a graph plotting, for a representative example, an average plunger sensor force curve, a plunger sensor force derivative curve, a baseline, a derivative threshold, a defined baseline range, an expected force differential Li, and a/:::,. delay point threshold.

FIG. 6 illustrates a graph plotting, for a representative example, an average plunger sensor force curve 162, a plunger sensor force (negative) derivative curve 164, a baseline 166, a derivative threshold 168, a defined baseline range 170, an expected force differential Δ 172, and a Δ delay point threshold 174. The right-most Y-axis represents average pounds of force on the plunger detected by a plunger force sensor, the left-most Y-axis represents a derivative (average) of the force on the plunger of FIG. 2 in pounds per milliliter, and the X-axis represents volume in milliliters of the fluid delivered from the chamber. The average plunger sensor force curve 162 comprises the average force delivered with each circle representing a measured point of the cycle of the plunger with measured data point 1 being the first circle shown in the graph. The plunger sensor force derivative curve 164 comprises the derivative force per volume delivered with each triangle representing a measured point of the cycle of the plunger with measured derivative data point 1 being the first derivative triangle shown in the graph. The baseline 166 comprises a horizontal line 166. The derivative threshold 168 comprises a horizontal line. The defined baseline range 170 comprises a horizontal distance which in this example is 100 micro liters. The expected force differential Δ 172 comprises a vertical distance. The Δ delay point threshold 174 comprises a horizontal distance which in this example is 200 micro liters.

The method of FIG. 5 may be applied to the example of FIG. 6 as follows to determine if air is contained in the chamber. In step 134, the method starts. The method then proceeds to step 136 and a determination is made that the end-of-bag (EOB) has not been detected for measured point i=1. The method then proceeds to step 140 and a determination is made that there is not a confirmed peak for measured point i=1. The method then proceeds to step 144 and a determination is made that the derivative for measured point i=1 has not exceeded the derivative threshold. The method then proceeds to step 146, increments variable i, and the method then repeats step 136. The method continues to loop in the same manner until a determination is made in step 144 that the derivative for measured point i=17 exceeds the derivative threshold. The method then proceeds to step 148 and increments variable P from O to 1. The method then proceeds to step 150 and determines that variable P which currently equals 1 is not greater than the consecutive point threshold Pih of 1. The method then proceeds to step 146, increments i to 18, and repeats steps 136, 140, and 144. In step 144, a determination in is made that the derivative of measured point i=18 exceeds the derivative threshold. The method then proceeds to step 148 and increments variable P from 1 to 2. The method then proceeds to step 150 and determines that variable P which currently equals 2 is greater than the consecutive point threshold Pih of 1. The method then proceeds to step 152, confirms a peak, and takes a baseline B for the baseline range of 100 micro liters of average force data immediately prior to and up to measured point i=17 which is the trigger event. The method then proceeds to step 146, increments variable i to 19 and proceeds back to and repeats step 136.

In step 136, a determination is made that the end-of-bag (EOB) has not been detected for measured point 19. The method then proceeds to step 140 and determines that there is a confirmed peak for measured point i=19. The method then proceeds to step 142 and increments the delay points DP to 1. The method then proceeds to step 154 and determines that the differential between the baseline B and the current average force $\sigma(i)$ for measured point i=19 is not greater than the expected force differential Δ. The method then proceeds to step 158 and determines that the delay points DP of 1 is not greater than the Δ delay point threshold comprising the number of measured points in the cycle of the plunger, starting from the trigger event, within 200 micro liters of fluid delivered from the chamber. The method then proceeds to step 146, increments i and proceeds back to and repeats step 136. The method continues to loop through steps 136, 140, 142, and 154 until it is determined in step 154 that the differential between the baseline B and the current average force $\sigma(i)$ for measured point i=23 is greater than the expected force differential Δ. The method then proceeds to step 156, confirms that an end-of-bag (EOB) event has occurred, and proceeds through steps 146, 136, and 138 to turn on the end-of-bag alarm to indicate that air is in the chamber. The end-of-bag alarm being turned on may further comprise pausing the infusion.

The method of FIG. 5 was implemented to analyze 4 72 data sets for a variety of flow rates. The testing resulted in no false positive determinations of air being in the chamber and only one occurrence of a false negative which only equated to 0.2% of the sets resulting in an incorrect result.

Figure 7:
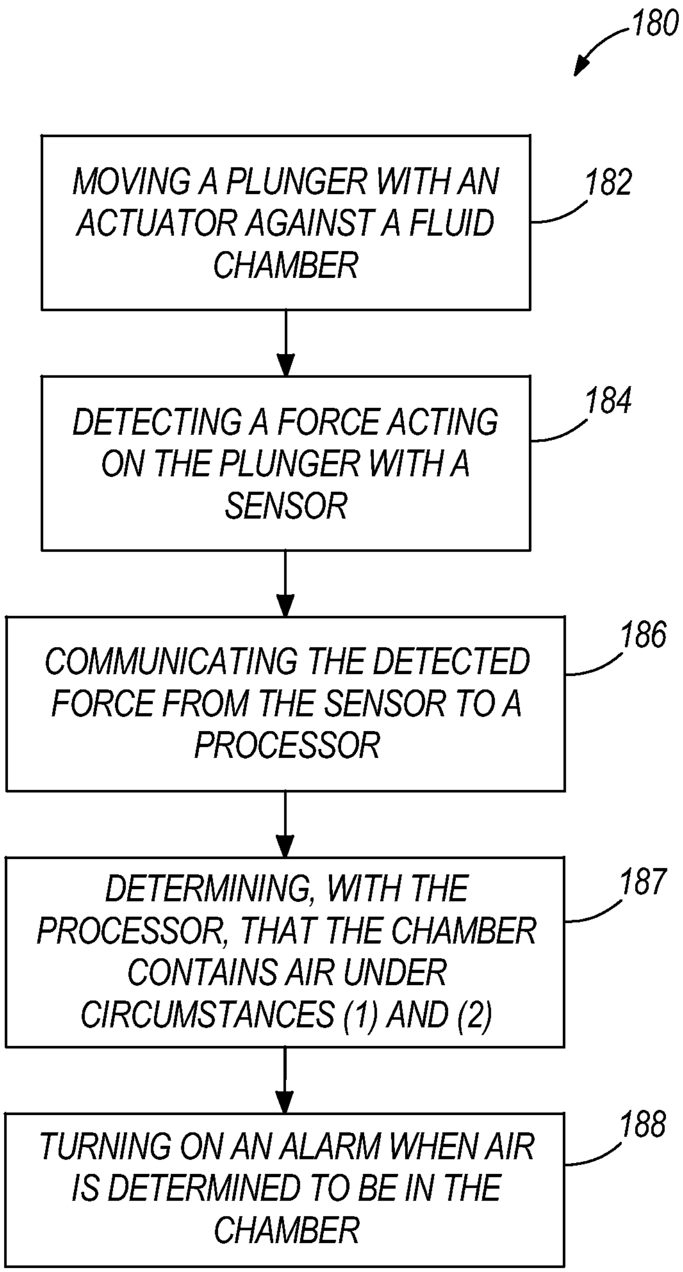
FIG. 7 illustrates a flowchart for one embodiment of a method for detecting air in a chamber of an infusion system.

FIG. 7 illustrates a flowchart for one embodiment of a method 180 for detecting air in a chamber of an infusion system. The method 180 may be implemented using the drug delivery infusion system 100 of FIG. 1 with the plunger being moved with the actuator device against the chamber containing fluid, the sensor detecting a force acting on the plunger as it moves against the chamber, the processor processing the force measurements taken by the sensor and implementing programming code stored in a non-transient memory in order to determine whether air is contained in the chamber using the algorithm set forth in method 180, and the alarm being turned on if the processor determines that air is contained in the chamber which may trigger the pump being shut down. Moreover, the method 180 may utilize the clock of the drug delivery infusion system 100 of FIG. 1 to keep time of activities of the plunger or the sensor, and may use the positional sensor to determine a position of the plunger, with each being in electronic communication with the processor. In other embodiments, the method 180 may utilize varying components to implement the method.

In step 182 a plunger is moved with an actuator device against a chamber containing fluid. In step 184 a force acting on the plunger is detected with a sensor as the plunger moves against the chamber. In step 186 a measurement of the force is electronically communicated from the sensor to a processor. In step 187 a determination is made, with the processor, that the chamber contains air when: (1) a trigger event occurs in which a change in force acting on the plunger per delivered volume of the fluid exiting the chamber exceeds a threshold; and (2) subsequent to the trigger event a differential between a baseline average force acting on the plunger and a current average force acting on the plunger exceeds an expected force differential within a defined delay range. In step 188 the processor turns on an alarm when the processor determines that the chamber contains the air. Step 188 may further comprise shutting down the pump when the alarm is turned on.

In one embodiment of step 187 step (1), which must occur for the processor to determine that the chamber contains air, may further comprise for a consecutive number of measured points of a cycle of the plunger from the trigger event the derivative force acting on the plunger per the delivered volume of the fluid exiting the chamber continuing to exceed the derivative threshold for more than a threshold number of the measured points of the cycle of the plunger against the chamber. In one embodiment of step 187 the baseline average force of step (2) may comprise the average force acting on the plunger over a defined baseline range occurring up to the trigger event. The baseline average force may further represent the chamber being filled with the fluid. In other embodiments, any of the steps of method 180 may be altered, not followed, or additional steps may be added.

In another embodiment of the disclosure, the drug delivery infusion system 100 of FIG. 1 may determine when air is present in the chamber 108 by analyzing a shape of the force profile on the plunger 107 and determining that air is contained in the chamber 108 when the shape of the force profile on the plunger 107 changes significantly from a baseline shape of a force profile representing liquid being in the chamber 108. This is because it has been discovered that when air reaches the chamber 108, the shape of the force profile on the plunger 107 during a stroke or cycle of the plunger 107 changes in a consistent manner when and after the transition is made from fluid being in the chamber 108 to air being in the chamber 108. The shape of the force profile on the plunger 107 can be used as for detecting air-in-line by discriminating the force profile shapes associated with air and fluid. The characteristics of the shape of the force profile depend on the delivery rate of the fluid being delivered from the chamber 108 with some variability related to mechanism, set, fluid type, and distal and proximal pressure.

Figure 8:
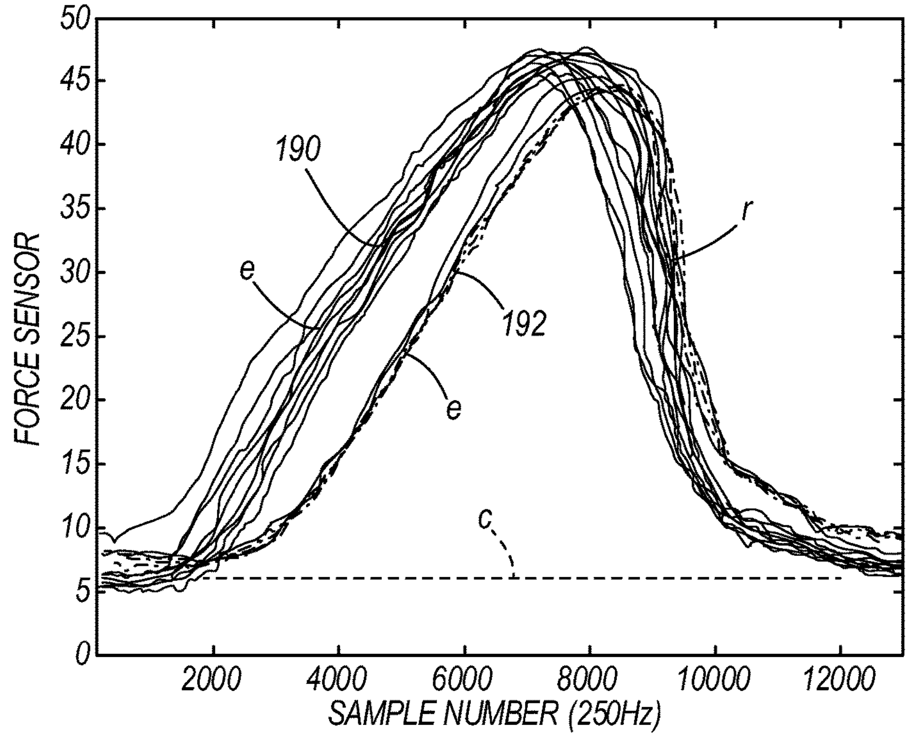
FIG. 8 illustrates a representative graph for one embodiment plotting a force sensor profile for a liquid curve and an air curve.

FIG. 8 illustrates a representative graph for one embodiment plotting a force sensor profile for a liquid curve 190 and an air curve 192. The Y-axis represents pounds of force on the plunger detected by a plunger force sensor and the X-axis represents a sample number collected at a rate of 250 Hz. Liquid curve 190 represents liquid being disposed in the chamber. Air curve 192 represents air being disposed in the chamber. As shown, the liquid curve 190 has substantially higher forces on the plunger than the air curve 192 during the expansion portion e of each cycle c of the plunger, while the difference between the curves 190 and 192 during the retraction phase r is significantly less.

Figure 9:
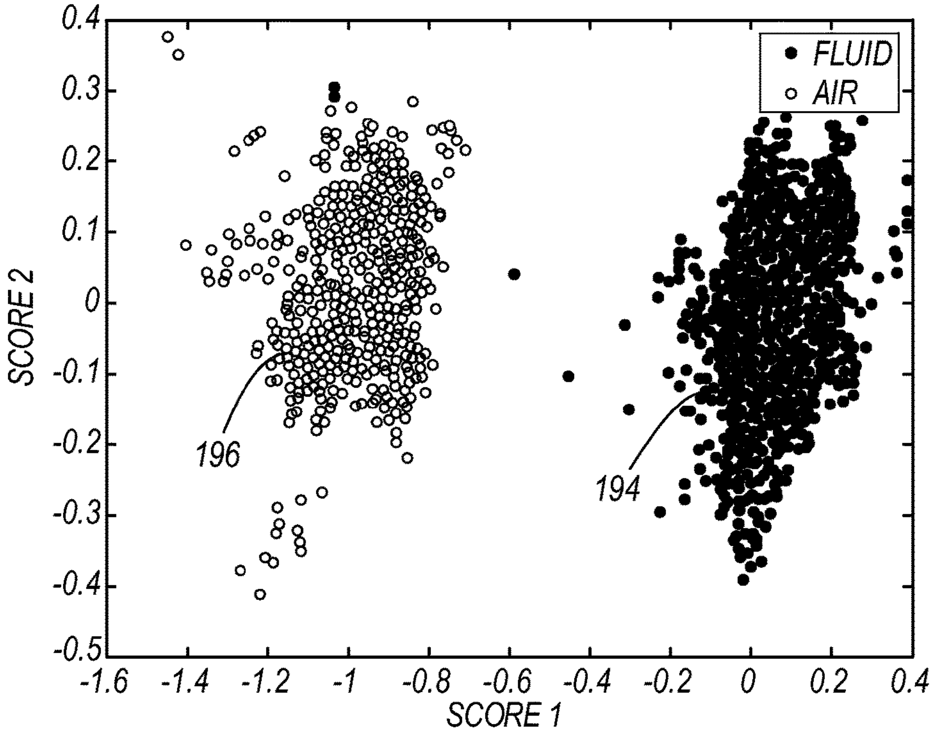
FIG. 9 illustrates a representative graph for one embodiment of a principal component analysis (PCA) which was done on a plunger force profile.

FIG. 9 illustrates a representative graph for one embodiment of a principal component analysis (PCA) which was done on a plunger force profile with points 194 representing liquid being disposed in the chamber and points 196 representing air being disposed in the chamber. The X-axis represents a first score and the Y-axis represents a second score. As shown, the points 194 representing liquid being disposed in the chamber have a higher first score than the points 196 representing air being disposed in the chamber.

Figure 10:
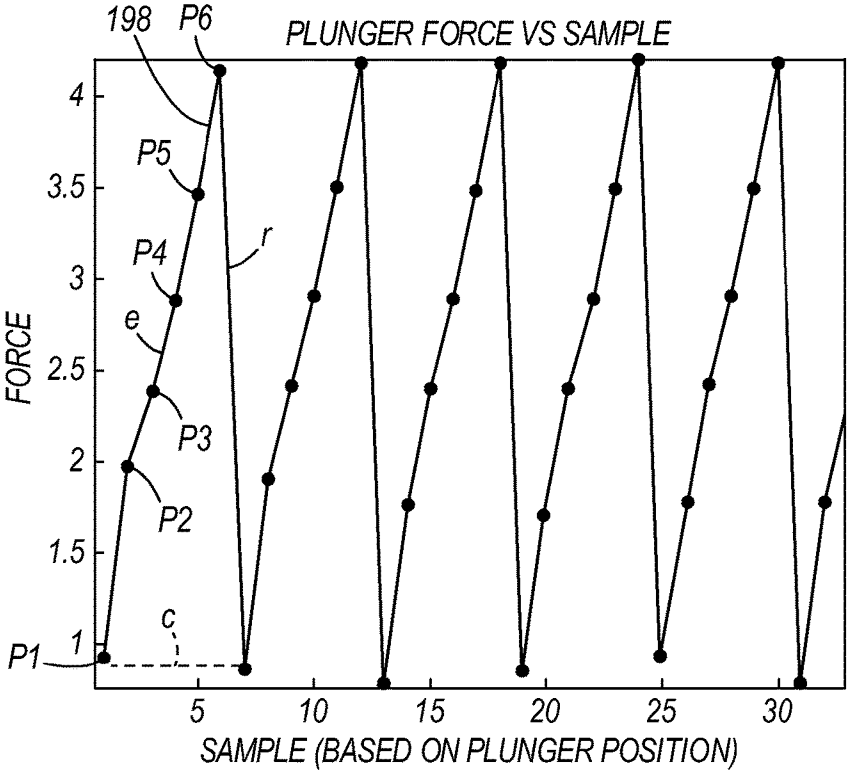
FIG. 10 illustrates a representative graph for one embodiment plotting a plunger force profile.

FIG. 10 illustrates a representative graph for one embodiment plotting a plunger force profile 198. The Y-axis represents pounds of force on the plunger detected by a plunger force sensor and the X-axis represents sample number for each cycle c of the plunger. As shown, six points p1-p6, comprising a 6 point vector pattern, are sampled at specific plunger positions during the expansion portion e of each cycle (or stroke) c of the plunger. No points are sampled during the retraction portion r of each cycle c of the plunger. This force sampling of each cycle may be used to determine whether air or liquid is contained in the chamber based on the shape of the measured force profile. The determination may be made using principle component analysis (PCA) to determine the correlation between the pattern variance of fluid versus air being in the chamber. Pre-processing may be applied to normalize the patterns across sets/needle heights and varying mechanisms. Separate analysis is performed for each separate fluid infusion rate or ranges of infusion rates. In other embodiments, a varying number of points per cycle of the plunger may be utilized, and the determination may be made using varying types of analysis.

Figure 11:
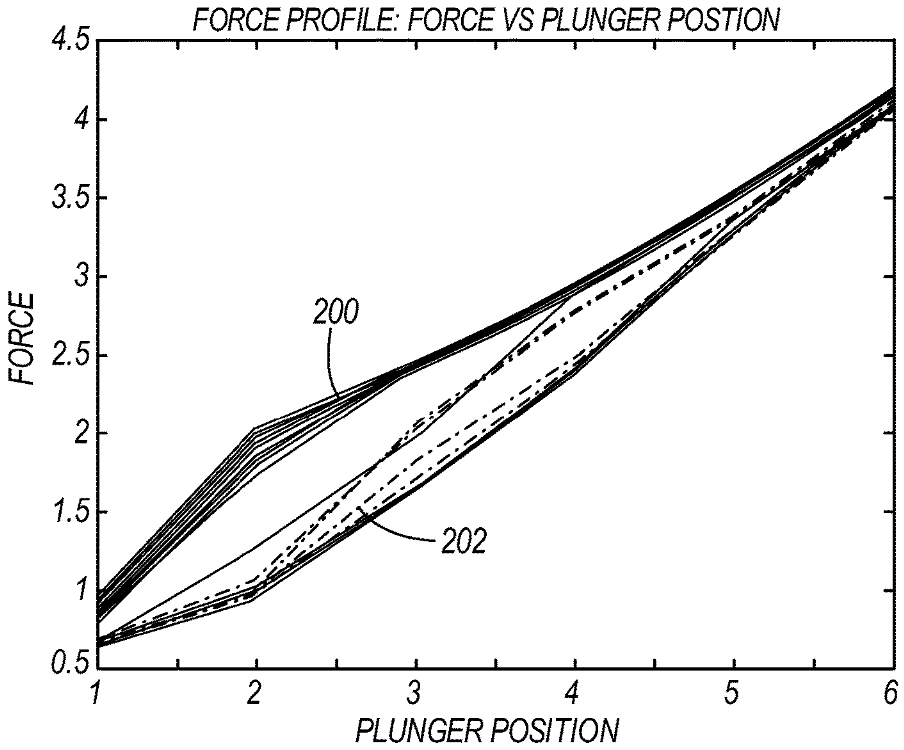
FIG. 11 illustrates a representative graph for one embodiment plotting a liquid plunger force curve and an air plunger force curve.

FIG. 11 illustrates a representative graph for one embodiment plotting a liquid plunger force curve 200 and an air plunger force curve 202. The Y-axis represents pounds of force on the plunger detected by a plunger force sensor and the X-axis represents a sample number of a cycle of the plunger. Liquid plunger force curve 200 represents liquid being disposed in the chamber. Air plunger force curve 202 represents air being disposed in the chamber. As shown, the liquid plunger force curve 200 has substantially higher forces on the plunger than the air plunger force curve 202.

Figure 13:
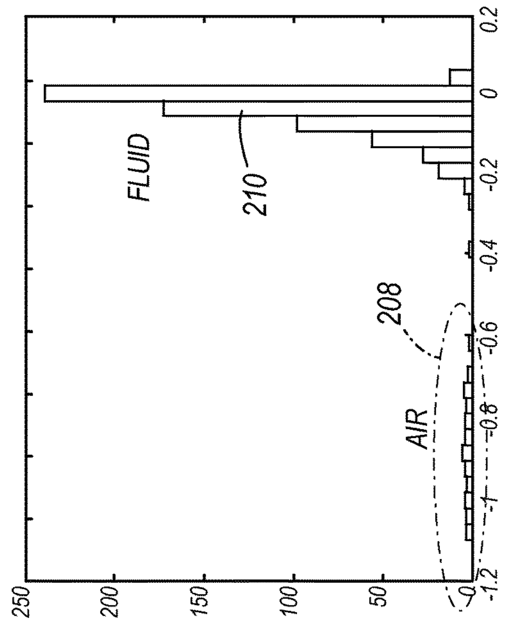
FIG. 13 illustrates a representative graph for one embodiment plotting, at an infusion rate of 550 ml/hour the distribution of the maximum absolute difference between a reference plunger force profile and subsequent profiles comprising an air curve and a liquid curve.
Figure 12:
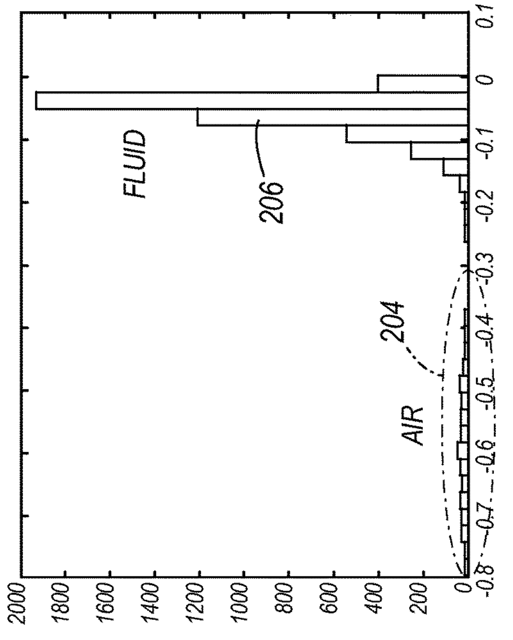
FIG. 12 illustrates a representative graph for one embodiment plotting, at an infusion rate of 20 ml/hour, the distribution of the maximum absolute difference between a reference plunger force profile and subsequent profiles comprising an air curve and a liquid curve.

FIG. 12 illustrates a representative graph for one embodiment plotting, at an infusion rate of 20 ml/hr, the distribution of the maximum absolute difference between a reference plunger force profile and subsequent profiles comprising an air curve 204 and a liquid curve 206. The Y-axis represents the number of profiles and the X-axis represents the difference associated with the point of the maximum absolute difference between the measured force profile and the baseline profile. Air curve 204 represents air being disposed in the chamber and liquid curve 206 represents liquid being disposed in the chamber. As shown, the liquid curve 206 has a substantially lower difference from the (liquid) baseline than the air curve 204. FIG. 13 illustrates a representative graph for one embodiment plotting, at an infusion rate of 550 ml/hr, the distribution of the maximum absolute difference between a reference plunger force profile and subsequent profiles comprising an air curve 208 and a liquid curve 210. The Y-axis represents the number of profiles and the X-axis represents the difference associated with the point of the maximum absolute difference between the measured force profile and the baseline profile. Air curve 208 represents air being disposed in the chamber and liquid curve 210 represents liquid being disposed in the chamber. As shown, the liquid curve 210 has a substantially lower difference from the (liquid) than the air curve 208. FIGS. 12 and 13 demonstrate a significant difference between air and fluid across varying infusion rates after the maximum difference calculation is applied for feature extraction.

Figure 14:
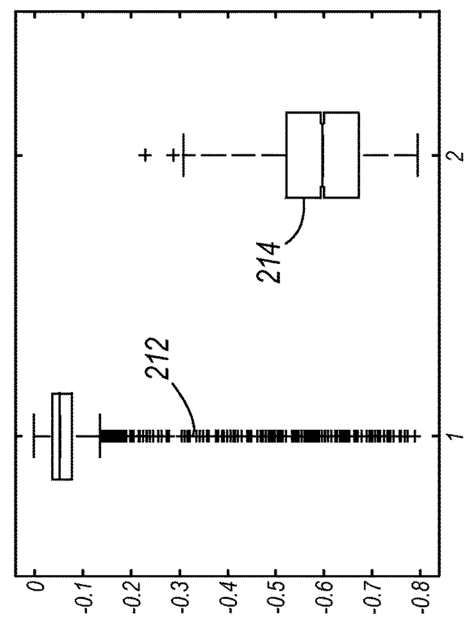
FIG. 14 illustrates a representative graph for one embodiment plotting, at an infusion rate of 20 ml/hr, an air plot and a liquid plot.

FIG. 14 illustrates a representative graph for one embodiment plotting, at an infusion rate of 20 ml/hr air depiction 212 and liquid depiction 214. The Y axis represents the difference between the observed force and the and the X axis represents two groups: (1) the group of differences associated with liquid in the plunger chamber; and (2) the difference with air in the plunger chamber Air depiction 212 represents air being disposed in the chamber and liquid depiction 214 represents liquid being disposed in the chamber. As shown, the air depiction 212 has a substantially lower (more negative) difference from the liquid baseline while the fluid 212 has a difference that is close to zero from the liquid baseline. The separation between the two groups provides the basis for a method for discriminating force measurements associated with air from those associated with fluid.

An algorithm has been discovered that normalizes a force shape profile of a plunger by determining a baseline force profile specific to each infusion program, and by using one generic feature, independent of the infusion program/rate, to assess whether air is contained in the chamber. To implement the algorithm, each force shape profile of the plunger is compared to a baseline force profile, a point-by-point difference between the force shape profile and the baseline force profile is determined, and when the minimum (most negative) difference between the force shape profile and the baseline force profile drops below a threshold a determination is made that the chamber contains air. The baseline force profile may represent liquid being in the chamber. In other embodiments, varying algorithms may be implemented to determine when air is contained in the chamber based on the force shape profile of the plunger.

Figure 15:
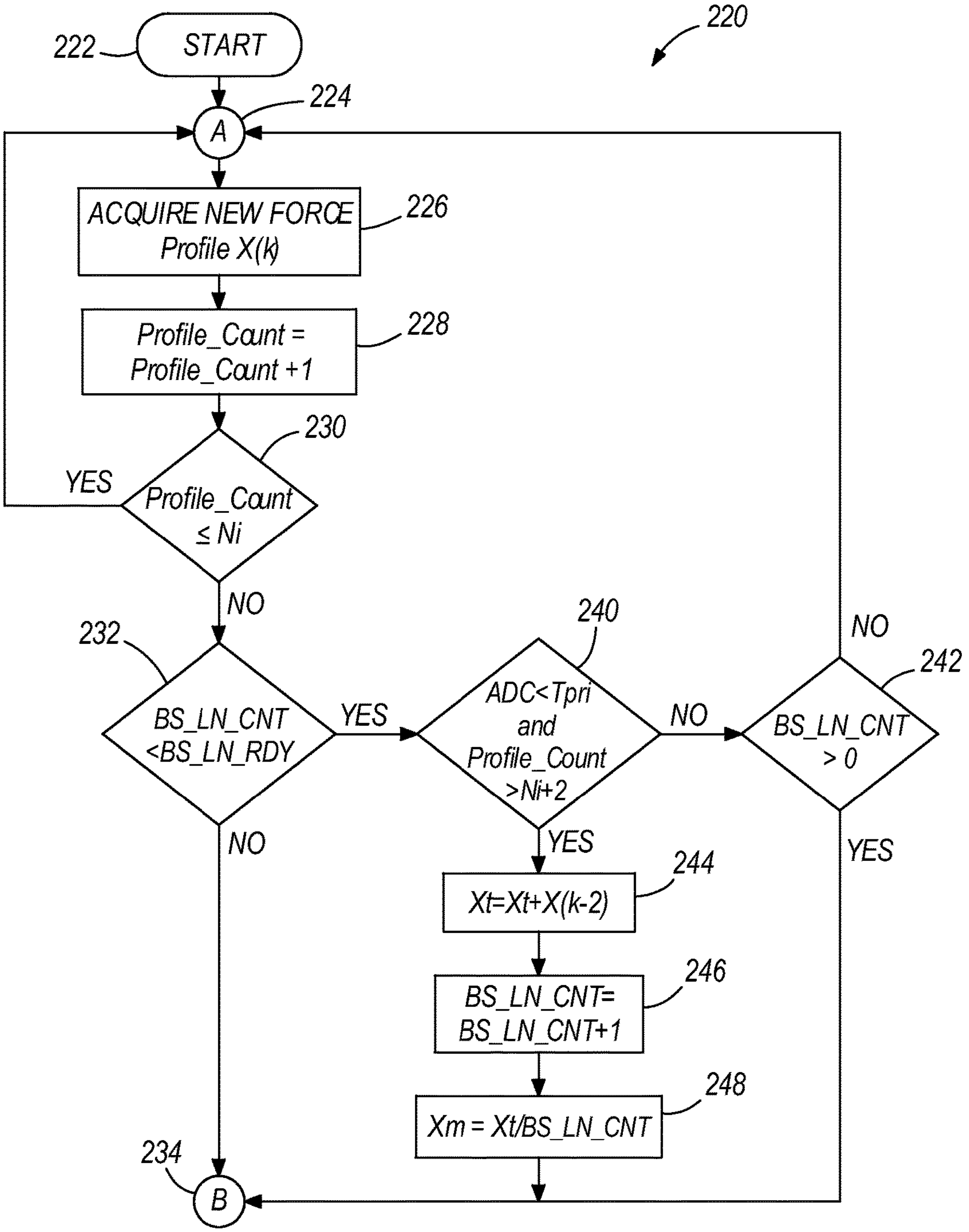
FIG. 15 illustrates one embodiment of a method, comprising a continuous flow chart, under the disclosure for determining whether air is contained in a chamber of a pump.
Figure 16:
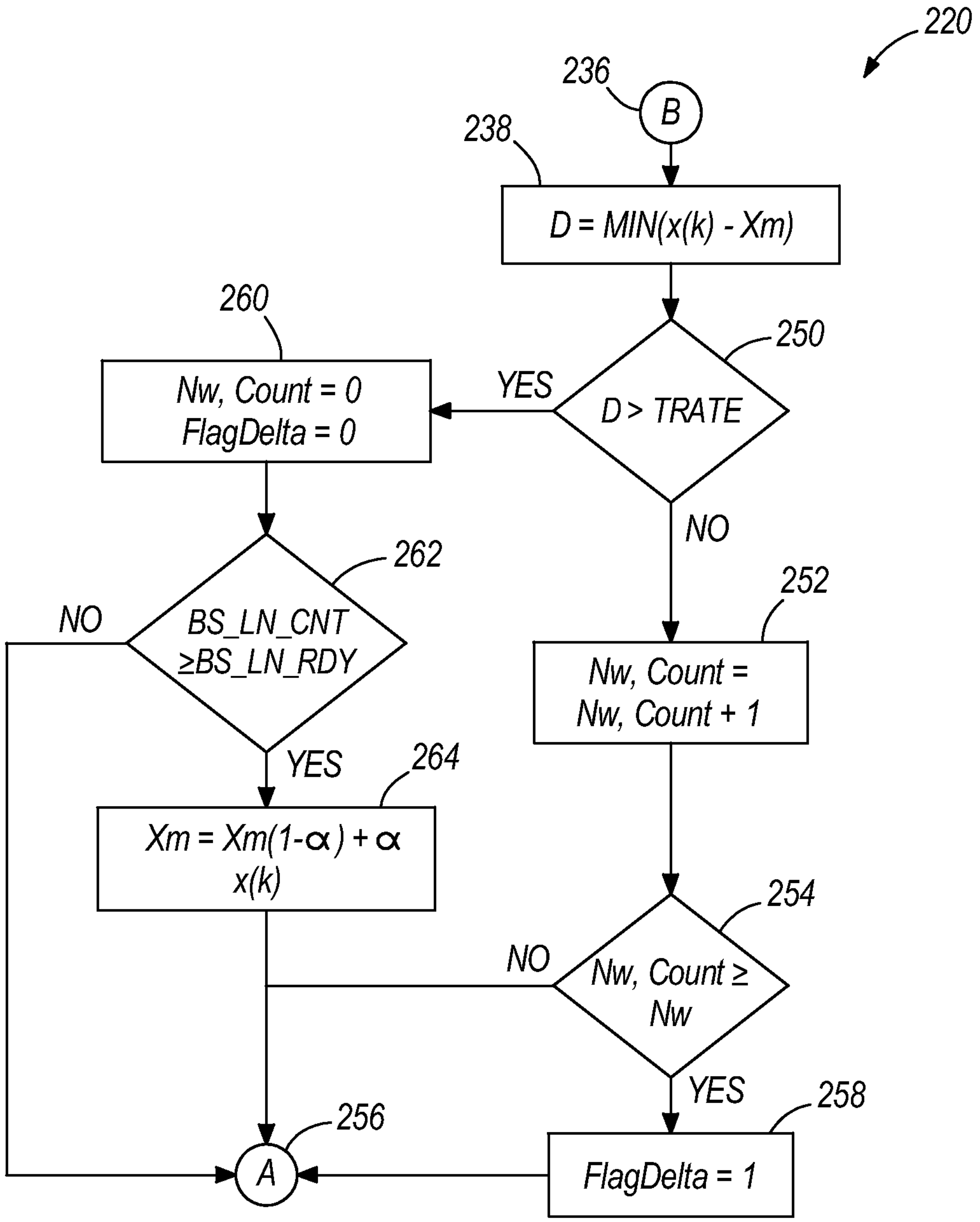
FIG. 16 illustrates a continuation of the flow chart of FIG. 15.

FIGS. 15 and 16 illustrate one embodiment of a method 220, comprising a continuous flow chart, under the disclosure for determining whether air is contained in a chamber of a pump. The method 220 may be implemented using the drug delivery infusion system 100 of FIG. 1 with the plunger being moved with the actuator device against the chamber containing fluid, the sensor detecting a force acting on the plunger as it moves against the chamber, the processor processing the force measurements taken by the sensor and implementing programming code stored in a non-transient memory in order to determine whether air is contained in the chamber using the algorithm set forth in method 220, and the alarm being turned on if the processor determines that air is contained in the chamber which may further shut down the pump. Moreover, the method 220 may utilize the clock of the drug delivery infusion system 100 of FIG. 1 to keep time of activities of the plunger or the sensor, and may use the positional sensor to determine a position of the plunger. In other embodiments, the method 220 may utilize varying components to implement the method.

In step 222, the method starts. After step 222, the method proceeds through location step 224 to step 226. In step 226, a force profile X(k) of the plunger is acquired for the first cycle of the plunger with k=1 representing the first cycle of the plunger. The force profile X(k) comprises a vector comprising the six forces on the plunger at each of the six positions/points of the plunger during the k cycle of the plunger. In other embodiments, the force profile may be acquired with a varying number of positions of the plunger. The method then proceeds to step 228 and increments the profile count PC using the equation PC=PC+1 with PC initially being O the first time through so that PC will be incremented to 1. The method then proceeds to step 230 and determines whether the profile count PC is less than or equal to the number of initial cycles of the plunger to ignore Ni which is set to Ni=2. In other embodiments, Ni may be set to other values.

If step 230 determines that the profile count PC is less than or equal to the number of initial cycles of the plunger to ignore Ni then the method proceeds back to and repeats steps 224, 226, 228, and 230 until the profile count PC is not less than or equal to the number of initial cycles of the plunger to ignore Ni at which point the method proceeds to step 232. In step 232 a determination is made as to whether the baseline count BS_LN_CNT is less than the baseline ready variable BS_LN_RDY. The baseline count BS_LN_CNT is initially set to BS_LN_CNT=0. The baseline ready variable BS_LN_RDY is set to BS_LN_RDY=5. In other embodiments, BS_LN_CNT and BS_LN_RDY may be set to other values. If step 232 determines that BS_LN_CNT is not less than BS_LN_RDY than the method proceeds through location step 234 of FIG. 15, through location step 236 of FIG. 16, to step 238 of FIG. 16 which is discussed later on.

If in step 232 a determination is made that the baseline count BS_LN_CNT is less than BS_LN_RDY than the method proceeds to step 240. In step 240 a determination is made as to whether the Analog-To-Digital-Count (ADC) at that instant is less than the primary threshold for fluid TPRI, and as to whether the profile count PC is greater than the number of initial cycles of the plunger to ignore plus 2 represented by PC being greater than Ni+2. The primary threshold for fluid TPRI is set to 3,000. In other embodiments, the primary threshold for fluid TPRI may be set to other values. If the determination in step 240 is made that either the Analog-To-Digital-Count (ADC) read by an air sensor downstream of the chamber is not less than the primary threshold for fluid TPRI (which means that air is in the chamber), or that the profile count PC is not greater than the number of initial cycles of the plunger to ignore plus 2 (there is a lag of 2 cycles due to the air sensor being located downstream of the chamber) represented by PC being greater than Ni+2, than the method proceeds to step 242, and determines whether the baseline count BS_LN_CNT is greater than 0. In other embodiments, the lag number of cycles used may vary. If step 242 determines that the baseline count BS_LN_CNT is not greater than O then the method proceeds back to location step 224 to step 226 and continues the loop. If step 242 determines that the baseline count BS_LN_CNT is greater than O then the method proceeds through location step 234 of FIG. 15, through location step 236 of FIG. 16, to step 238 of FIG. 16 which is discussed later on.

If in step 240 the determination is made that either the Analog-To-DigitalCount (ADC) read by an air sensor downstream of the chamber is less than the primary threshold for fluid TPRI (which means that liquid is in the chamber), and that the profile count PC is greater than the number of initial cycles of the plunger to ignore plus 2 (indicating that the lag of 2 cycles, due to the air sensor being located downstream of the chamber, has been completed) represented by PC being greater than Ni+2, then the method proceeds to step 244. In step 244, the accumulated baseline profile Xt is determined using the equation Xt=Xt+X(k−2) (wherein X(k−2) represents the force profile, expressed as a six point vector, for 2 cycles ago due to the air sensor being located downstream of the chamber) wherein Xt is initially set to 0 and k represents the number of the current cycle of the plunger. In other embodiments, the equation for Xt may be varied. After step 244, the method proceeds to step 246 and increments the baseline count BS_LN_CNT using the equation BS_LN_CNT=BS_LN_CNT+1. After step 246, the method proceeds to step 248 and determines the baseline force profile Xm, expressed as a 6 point vector, using the equation Xm=Xt I BS_LN_CNT which averages the force measurements on the plunger taken at times when liquid is in the chamber over the number of baseline count BS_LN_CNT cycles of the plunger. The baseline force profile Xm represents the baseline force vector for a situation in which liquid (fluid) is contained in the chamber 2 cycles prior to the current cycle due to the air sensor being located downstream of the chamber. In other embodiments, the baseline force profile Xm may be calculated using varying equations. After step 248, the method proceeds through location step 234 of FIG. 15, through location step 236 of FIG. 16, to step 238 of FIG. 16.

In step 238 of FIG. 16, the minimum distance D between the current vector force profile of the plunger and the baseline force vector is determined using the equation D=min(X(k)−Xm) where k represents the current cycle of the plunger and Xm represents the baseline force vector with D being the single minimum distance between the corresponding 6 points of the two vectors. After step 238, the method proceeds to step 250 and determines whether D is greater than a threshold for a given infusion rate Trate which is set to −0.3. In other embodiments, Trate may be set to a varying number depending on the infusion rate or other factors, such as the signal variance. Additionally, more than one value for Trate may be used to provide regions of high probability versus low probability. If a determination is made in step 250 that the minimum distance D between the current vector force profile of the plunger and the baseline force vector is not greater than the threshold for a given infusion rate Trate, which indicates that air is in the chamber, then the method proceeds to step 252.

In step 252, Nw count is incremented using the equation Nw count=Nw count+1 with Nw count initially set to 0. Nw count represents the current number of observed air cycles. After step 252, the method proceeds to step 254 and determines whether Nw count is greater than or equal to Nw with Nw representing the threshold number of consecutive observed air cycles of the plunger after which an air alarm will be turned on indicating that air is contained in the chamber. If a determination is made in step 254 that Nw count is not greater than or equal to Nw than the method proceeds through location step 256 back to location step 224 of FIG. 15 to step 226 of FIG. 15 and repeats the loop. If a determination is made in step 254 that Nw count is greater than or equal to Nw than the method proceeds to step 258, sets Flag Delta to 1 indicating that air is present in the chamber, turns on an alarm to indicate that air is present in the chamber, and proceeds through location step 256 back to location step 224 of FIG. 15 to step 226 of FIG. 15 and repeats the loop. Step 258 may further comprise shutting down the pump.

If a determination is made in step 250 that the minimum distance D between the current vector force profile of the plunger and the baseline force vector is greater than the threshold for a given infusion rate Trate, indicating that liquid is contained in the chamber, then the method proceeds to step 260. In step 260, Nw count is reset to O with Nw count representing the current number of observed air cycles, and Flag Delta is also reset to O with Flag Delta representing that air is present in the chamber. After step 260, the method proceeds to step 262 and determines whether the baseline count BS_LN_CNT is greater than or equal to the baseline ready variable BS_LN_RDY which is set to BS LN ROY=5. In other embodiments, the baseline ready variable BS_LN_RDY may be set to other values.

If a determination is made in step 262 that the baseline count BS_LN_CNT is not greater than or equal to the baseline ready variable BS_LN_RDY then the method proceeds through location step 256 back to location step 224 of FIG. 15 to step 226 of FIG. 15 and repeats the loop. If a determination is made in step 262 that the baseline count BS_LN_CNT is greater than or equal to the baseline ready variable BS_LN_RDY then the method proceeds to step 264. In step 264 the baseline force profile Xm, expressed as a 6 point vector, is calculated using an adaptive baseline force profile equation Xm=Xm*(1−a)+a*X(k) wherein a comprises a forgetting rate which determines what percentage of the calculated baseline force profile Xm comprises the preceding calculated baseline force profile Xm and what percentage of the baseline force profile Xm comprises the current force profile X(k) where X(k) is the current force profile of the plunger for the k cycle of the plunger. In one embodiment the forgetting rate a may be set to 0.1. In other embodiments, the forgetting rate a may be set to varying values. The adaptive baseline may be determined in alternate manners such as a moving average or Kalman filter.

Step 264 comprises an adaptive baseline step which allows the user to assert control over the baseline force profile Xm by controlling the forgetting rate a. In other embodiments, the forgetting rate a may be pre-programmed. In still other embodiments, varying ways may be used to calculate the baseline force profile Xm. After step 264 the method proceeds through location step 256 back to location step 224 of FIG. 15 to step 226 of FIG. 15 and repeats the loop. In other embodiments, one or more steps of the method 220 may be modified, not followed, or one or more additional steps may be added. Moreover, any of the variables of the method 220 may be either user set, using an input device, or pre-set into the processor.

Figure 17:
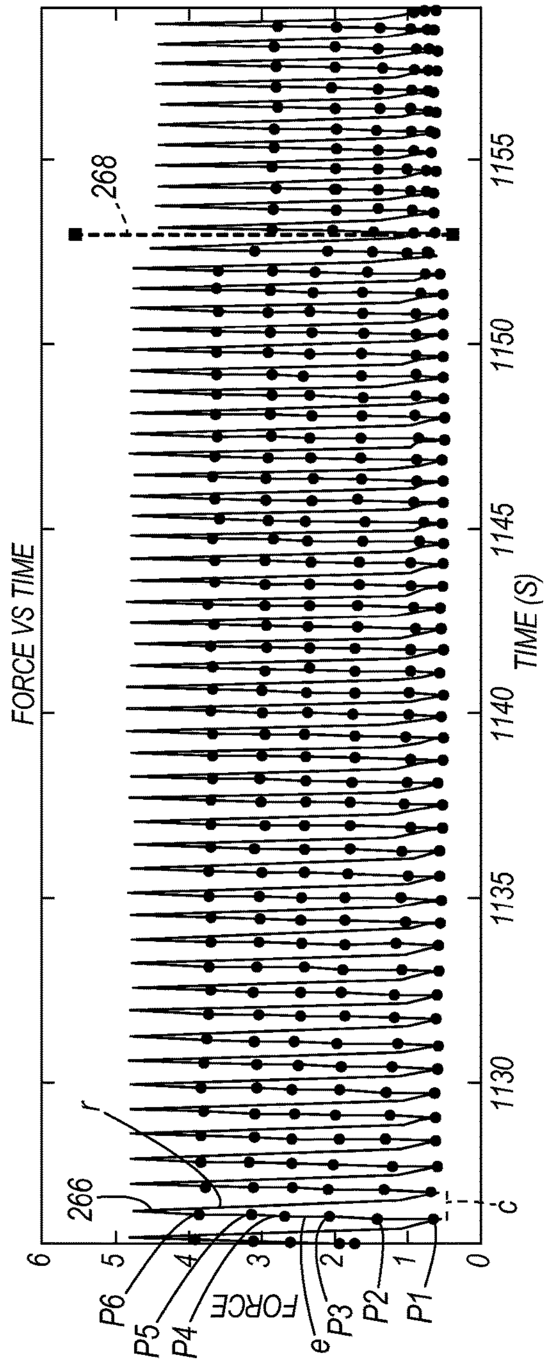
FIG. 17 illustrates a representative graph for one embodiment plotting a force sensor profile.

FIG. 17 illustrates a representative graph for one embodiment plotting a force sensor profile 266. The Y-axis represents pounds of force on the plunger detected by a plunger force sensor and the X-axis represents time in seconds. Six points p1-p6 are calculated during the expansion portion e of each cycle c of the plunger. No points are sampled during the retraction portion r of each cycle c of the plunger. Line 268 represents the point, during the fortyfifth cycle of the plunger, at which an air alarm is turned on due to air being in the chamber when the method 220 of FIGS. 15 and 16 is applied which is discussed more thoroughly below.

Figure 18:
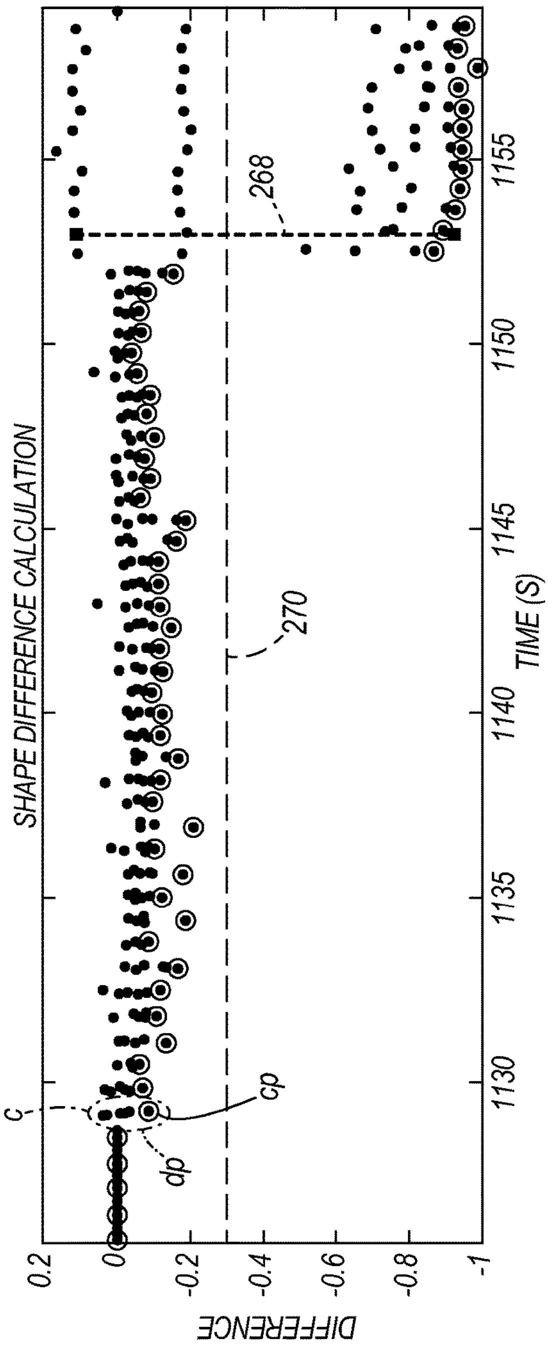
FIG. 18 illustrates a graph plotting for each cycle of the plunger of FIG. 17 six respective difference points representing the measured differences between a baseline, comprising liquid being in the chamber, and the corresponding points of each respective cycle of the plunger.

FIG. 18 illustrates a graph plotting for each cycle c of the plunger of FIG. 17 six respective difference points dp representing the measured differences between a baseline, comprising liquid being in the chamber, and the corresponding points of each respective cycle of the plunger. The Y-axis represents the differences and the X-axis represents time. The circled points cp represent the minimum difference for each cycle of the plunger between the six respective difference points dp of each cycle of the plunger and the baseline. Line 270 represents the threshold for a given infusion rate Trate which is set to −0.3. As discussed more thoroughly below, when the method 220 of FIGS. 15 and 16 is applied, the method determines that liquid is contained in the chamber during the first forty-three cycles of the plunger, determines that air is in the chamber during the forty-fourth cycle of the plunger, and after line 268, as it does in FIG. 17, turns on an air alarm during the forty-fifth cycle of the plunger representing that air is in the chamber.

Figure 19:
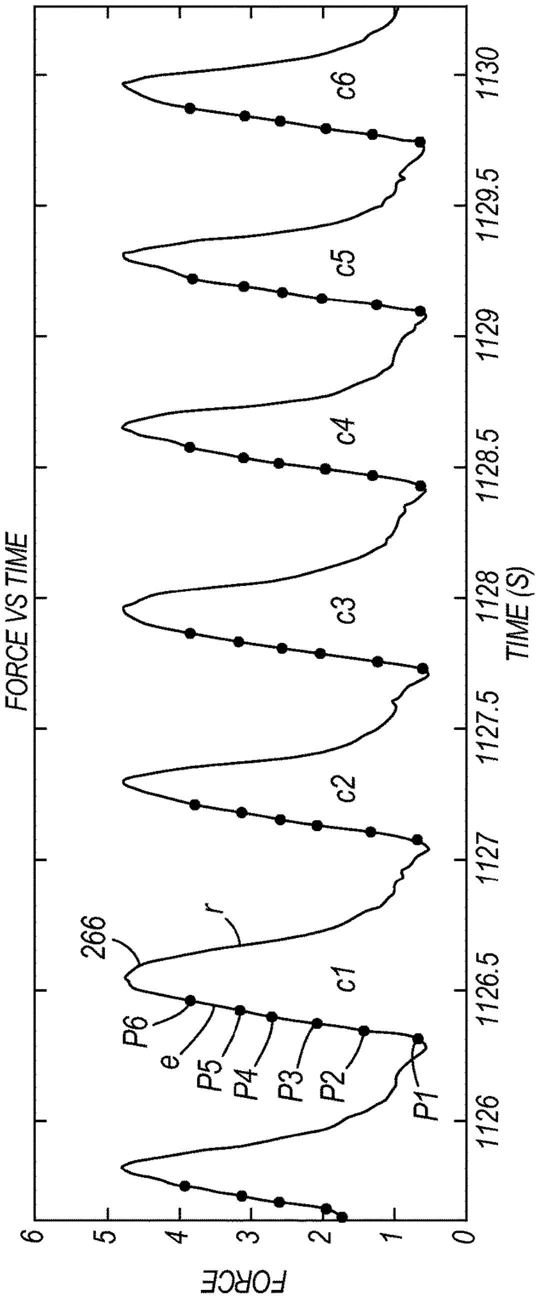
FIG. 19 illustrates a graph plotting the first six full cycles of the force sensor profile of FIG. 17.

FIG. 19 illustrates a graph plotting the first six full cycles C1-C6 of the force sensor profile 266 of FIG. 17. The Y-axis represents pounds of force on the plunger detected by a plunger force sensor and the X-axis represents time in seconds. Six points p1-p6 are calculated during the expansion portion e of each cycle c of the plunger. No points are sampled during the retraction portion r of each cycle c of the plunger.

Figure 20:
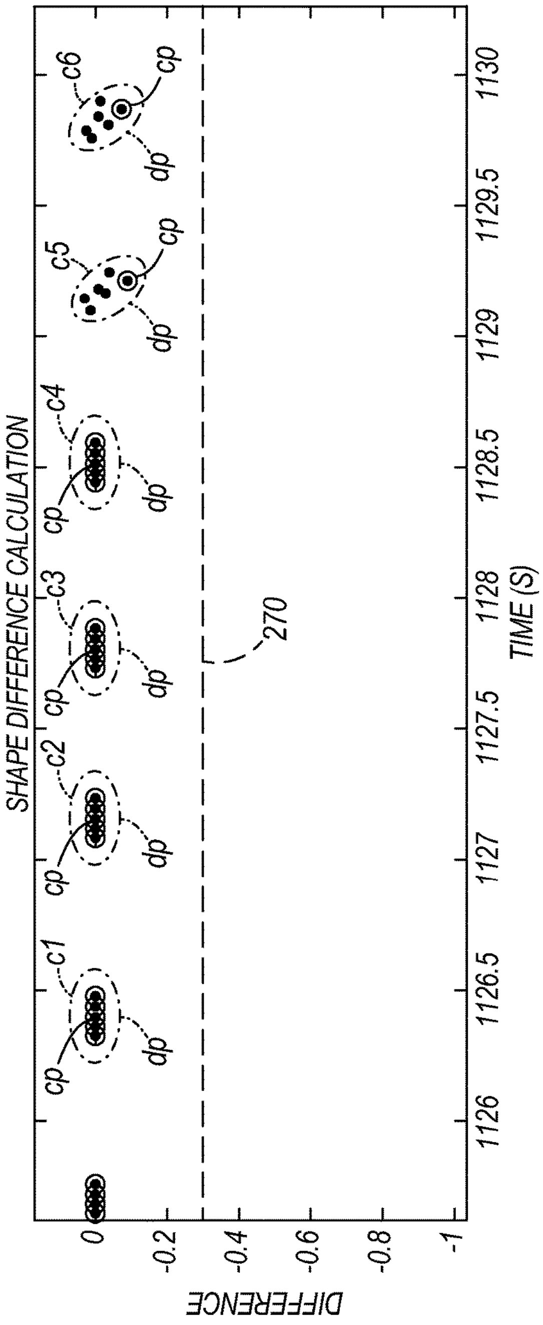
FIG. 20 illustrates a graph plotting for each of the first six full cycles of the plunger of FIG. 18 six respective difference points representing the measured differences between a baseline, comprising liquid being in the chamber, and the corresponding points of each respective cycle of the plunger.

FIG. 20 illustrates a graph plotting for each of the first six full cycles C1-C6 of the plunger of FIG. 18 six respective difference points dp representing the measured differences between a baseline, comprising liquid being in the chamber, and the corresponding points of each respective cycle of the plunger. The Y-axis represents the differences and the X-axis represents time. The circled points cp represent the minimum difference for each cycle of the plunger between the six respective difference points dp of each cycle of the plunger and the baseline. Line 270, as it does in FIG. 18, represents the threshold for a given infusion rate Trate which is set to −0.3. As discussed more thoroughly below, when the method of FIGS. 15 and 16 is applied the method determines that liquid is contained in the chamber during each of the first six full cycles C1-C6 of the plunger.

Figure 21:
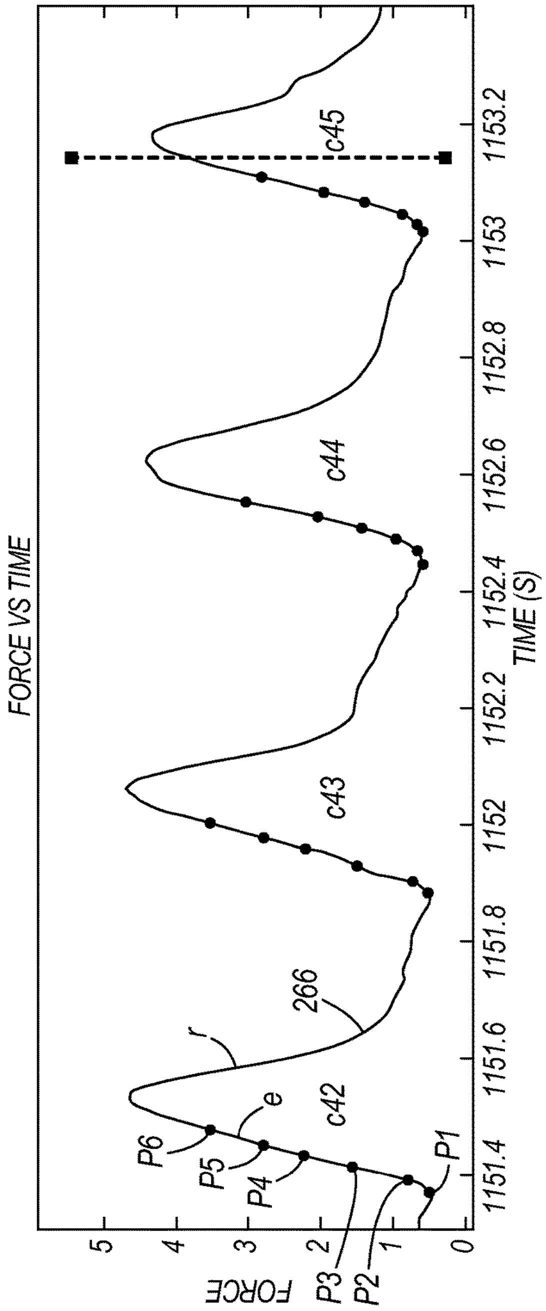
FIG. 21 illustrates a graph plotting the forty-second through forty-fifth cycles of the force sensor profile of FIG. 17.

FIG. 21 illustrates a graph plotting the forty-second through forty-fifth cycles C42-C45 of the force sensor profile 266 of FIG. 17. The Y-axis represents pounds of force on the plunger detected by a plunger force sensor and the X-axis represents time in seconds. Six points p1-p6 are calculated during the expansion portion e of each cycle c of the plunger. No points are sampled during the retraction portion r of each cycle c of the plunger.

Figure 22:
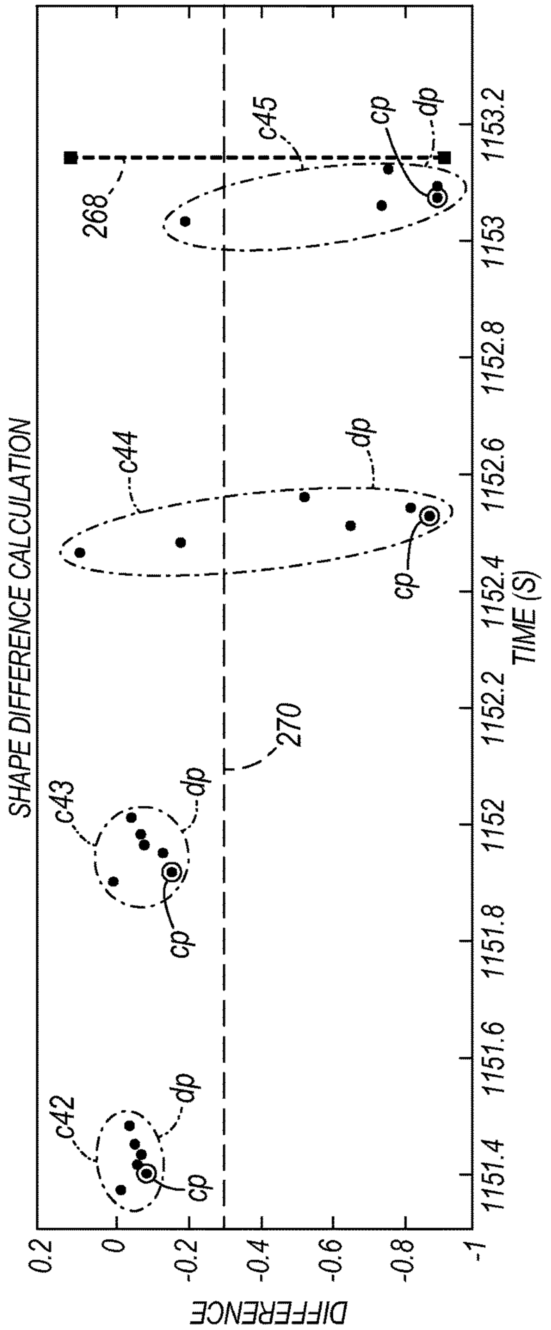
FIG. 22 illustrates a graph plotting for the forty-second through fortyfifth cycles of the plunger of FIG. 18 six respective difference points representing the measured differences between a baseline, comprising liquid being in the chamber, and the corresponding points of each respective cycle of the plunger.

FIG. 22 illustrates a graph plotting for the forty-second through fortyfifth cycles C42-C45 of the plunger of FIG. 18 six respective difference points dp representing the measured differences between a baseline, comprising liquid being in the chamber, and the corresponding points of each respective cycle of the plunger. The Y-axis represents the differences and the X-axis represents time. The circled points cp represent the minimum difference for each cycle of the plunger between the six respective difference points dp of each cycle of the plunger and the baseline. Line 270, as it does in FIGS. 18 and 20, represents the threshold for a given infusion rate Trate which is set to −0.3. As discussed more thoroughly below, when the method 220 of FIGS. 15 and 16 is applied, the method determines that liquid is contained in the chamber during the first forty-three cycles of the plunger, determines that air is in the chamber during the forty-fourth cycle of the plunger, and after line 268, as it does in FIG. 17, turns on an air alarm during the forty-fifth cycle of the plunger representing that air is in the chamber.

The method 220 of FIGS. 15 and 16 will now be applied to the example of FIGS. 17-22 to demonstrate how the method works. In the interest of efficiency, only some of the steps of the method 220 are described below. When the method 220 of FIGS. 15 and 16 is applied to the example of FIGS. 17-22, the first two cycles C1 and C2 are skipped because the profile count PC of 1 and 2 respectively is less than or equal to Ni=2. The force profiles X(k) for the third and fourth cycles C3 and C4 are acquired but not used because the profile count PC of 3 and 4 respectively is not greater than the number of initial cycles of the plunger to ignore (Ni=2) plus 2 represented by PC being greater than 4 (Ni+2=2+2=4). When the profile count PC reaches 5 at the fifth cycle C5, the accumulated baseline profile Xt is determined because the measured ADC of 1,673 is less than the primary threshold for fluid TPRI of 3,000, and the profile count PC=5 is greater than 4 (Ni+2=2+2=4). At this point in time, the baseline force profile Xm, expressed as a six point vector, is calculated using the equation Xm=Xt I BS_LN_CNT wherein Xt=Xt [which is initially set to O]+X(k−2)=O+X(5−2)=O+X(3)=X(3) [representing the force profile for the third cycle] and BS_LN_CNT=BS_LN_CNT [which is initially set to O]+1=0+1=1. Applying this equation results in the baseline force profile, expressed as a six point force vector, being Xm=(0.574252, 1.192627, 1.990768, 2.551261, 3.144921, 3.823651). The method 220 then determines the minimum distance D between the current vector force profile X(k), where k=5, of the plunger and the baseline force vector using the equation D=min(X(k)−Xm)=min(X(5)−Xm)=min ((0.574252, 1.192627, 1.990768, 2.551261, 3.144921, 3.823651)−(0.601876, 1.226866, 1.968040, 2.542253, 3.058266, 3.787412))=min ((0.574252 −0.601876), (1.92627−1.226866), (1.990768−1.968040), (2.551261−2.542253), (3.144921−3.058266), (3.823651−3.787412))=min (0.027624, 0.034239, −0.022727, −0.009008, −0.086655, −0.036239)=−0.086655. Because D=−0.086655 is greater than Trate=−0.3, the method determines that the current cycle/profile is for liquid being in the chamber, and the adaptive baseline, using the forgetting rate a, is not applied because the baseline count BS_LN_CNT=1 is not greater than or equal to the baseline ready variable BS LN ROY=5.

For the sixth cycle C6 the profile count PC increases to 6 and the accumulated baseline profile Xt is determined because the measured ADC of 1,740 is less than the primary threshold for fluid TPRI of 3,000, and the profile count PC=6 is greater than 4 (Ni+2=2+2=4). At this point in time, the baseline force profile Xm, expressed as a six point vector, is calculated using the equation Xm=Xt I BS_LN_CNT wherein Xt=Xt+X(k−2) and BS_LN_CNT=2. Applying this equation results in the baseline force profile, expressed as a six point force vector, being Xm=(0.584984, 1.234167, 1.947920, 2.556566, 3.103720, 3.818871). The method 220 then determines the minimum distance D between the current vector force profile X(k), where k=6, of the plunger and the baseline force vector using the equation D=min(X(k)−Xm)=min(X(6)−Xm)=min ((0.600387, 1.266444, 1.916179, 2.547273, 3.031686, 3.805076)−(0.584984, 1.234167, 1.947920, 2.556566, 3.103720, 3.818871))=min ((0.600387−0.584984), (1.266444−1.234167), (1.916179−1.947920), (2.547273−2.556566), (3.031686−3.103720), (3.805076−3.818871))=min (0.015402, 0.032277, −0.031741, −0.009293, −0.072035, −0.013795)=−0.072035. Because D=−0.072035 is greater than Trate=−0.3, the method determines that the current cycle/profile is for liquid being in the chamber, and the adaptive baseline, using the forgetting rate a, is not applied because the baseline count BS_LN_CNT=2 is not greater than or equal to the baseline ready variable BS_LN_RDY=5.

When the method reaches the forty-third cycle C43 (the intermediate cycle calculations are not described here in the interest of efficiency) the profile count PC increases to 43 and the accumulated baseline profile Xt is determined because the measured ADC is less than the primary threshold for fluid TPRI of 3,000, and the profile count PC=43 is greater than 4 (Ni+2=2+2=4). At this point in time, the baseline force profile Xm, expressed as a six point vector, is calculated using the equation Xm=Xt I BS_LN_CNT wherein Xt=Xt+X(k−2) and BS_LN_CNT=39. Applying this equation results in the baseline force profile, expressed as a six point force vector, being Xm=(0.507904, 0.882215, 1.642329, 2.326609, 2.893227, 3.623199). The method 220 then determines the minimum distance D between the current vector force profile X(k), where k=43, of the plunger and the baseline force vector using the equation D=min(X(k)−Xm)=min(X(43)−Xm)=min ((0.521021, 0.729376, 1.515777, 2.249448, 2.828867, 3.582641)−(0.507904, 0.882215, 1.642329, 2.326609, 2.893227, 3.623199))=min ((0.521021−0.507904), (0.729376−0.882215), (1.515777−1.642329), (2.249448−2.326609), (2.828867−2.893227), (3.582641−3.623199))=min (0.013117, −0.152839, −0.126552, −0.077161, −0.064360, −0.040558)=−0.152839. Because D=−0.152839 is greater than Trate=−0.3, the method determines that the current cycle/profile is for liquid being in the chamber, and the adaptive baseline, using the forgetting rate a, is determined because the baseline count BS_LN_CNT=39 is greater than or equal to the baseline ready variable BS_LN_RDY=5. Applying the forgetting rate a=0.100000 to calculate the adaptive baseline results in the adaptive baseline Xm=Xm*(1−a)+a*X(k)=(0.509216, 0.866931, 1.629673, 2.318893, 2.886791, 3.619144).

When the method reaches the forty-fourth cycle C44 the profile count PC increases to 44 and the accumulated baseline profile Xt is determined because the measured ADC is less than the primary threshold for fluid TPRI of 3,000, and the profile count PC=44 is greater than 4 (Ni+2=2+2=4). At this point in time, the baseline force profile Xm, expressed as a six point vector, is calculated using the equation Xm=Xt I BS_LN_CNT wherein Xt=Xt+X(k−2) and BS_LN_CNT=40. Applying this equation results in the baseline force profile, expressed as a six point force vector, being Xm=(0.509216, 0.866931, 1.629673, 2.318893, 2.886791, 3.619144). The method 220 then determines the minimum distance D between the current vector force profile X(k), where k=44, of the plunger and the baseline force vector using the equation D=min(X(k)−Xm)=min(X (44)−Xm)=min ((0.616675, 0.690732, 0.974907, 1.446447, 2.064309, 3.097704)−(0.509216, 0.866931, 1.629673, 2.318893, 2.886791, 3.619144))=min ((0.616675−0.509216), (0.690732−0.866931), (0.974907−1.629673), (1.446447−2.318893), (2.064309−2.886791), (3.097704−3.619144))=min (0.107459, −0.176199, −0.654767, −0.872446, −0.822482, −0.521439)=−0.872446. Because D=−0.872446 is not greater than Trate=−0.3, the method determines that the current cycle/profile is for air being in the chamber and increments Nw count to Nw count+1=O+1=1.

When the method reaches the forty-fifth cycle C45 the profile count PC increases to 45 and the accumulated baseline profile Xt is determined because the measured ADC is less than the primary threshold for fluid TPRI of 3,000, and the profile count PC=45 is greater than 4 (Ni+2=2+2=4). At this point in time, the baseline force profile Xm, expressed as a six point vector, is calculated using the equation Xm=Xt I BS_LN_CNT wherein Xt=Xt+X(k−2) and BS_LN_CNT=41. Applying this equation results in the baseline force profile, expressed as a six point force vector, being Xm=(0.509216, 0.866931, 1.629673, 2.318893, 2.886791, 3.619144). The method 220 then determines the minimum distance D between the current vector force profile X(k), where k=45, of the plunger and the baseline force vector using the equation D=min(X(k)−Xm)=min(X (44)−Xm)=min ((0.613084, 0.674059, 0.891756, 1.421075, 1.990083, 2.859728)−(0.509216, 0.866931, 1.629673, 2.318893, 2.886791, 3.619144))=min ((0.613084−0.509216), (0.674059−0.866931), (0.891756−1.629673), (1.421075−2.318893), (1.990083−2.886791), (2.859728−3.619144))=min (0.103868, −0.192872, −0.737917, −0.897818, −0.896708, −0.759415)=−0.897818. Because D=−0.897818 is not greater than Trate=−0.3, the method determines that the current cycle/profile is for air being in the chamber, increments Nw count to Nw count+1=1+1=2, sets FlagDelta=1, and signals an air alarm indicating that air is in the chamber.

The method of FIGS. 15 and 16 was implemented to analyze a large number of data sets for a variety of flow rates. The testing resulted in no false negative occurrences.

Figure 23:
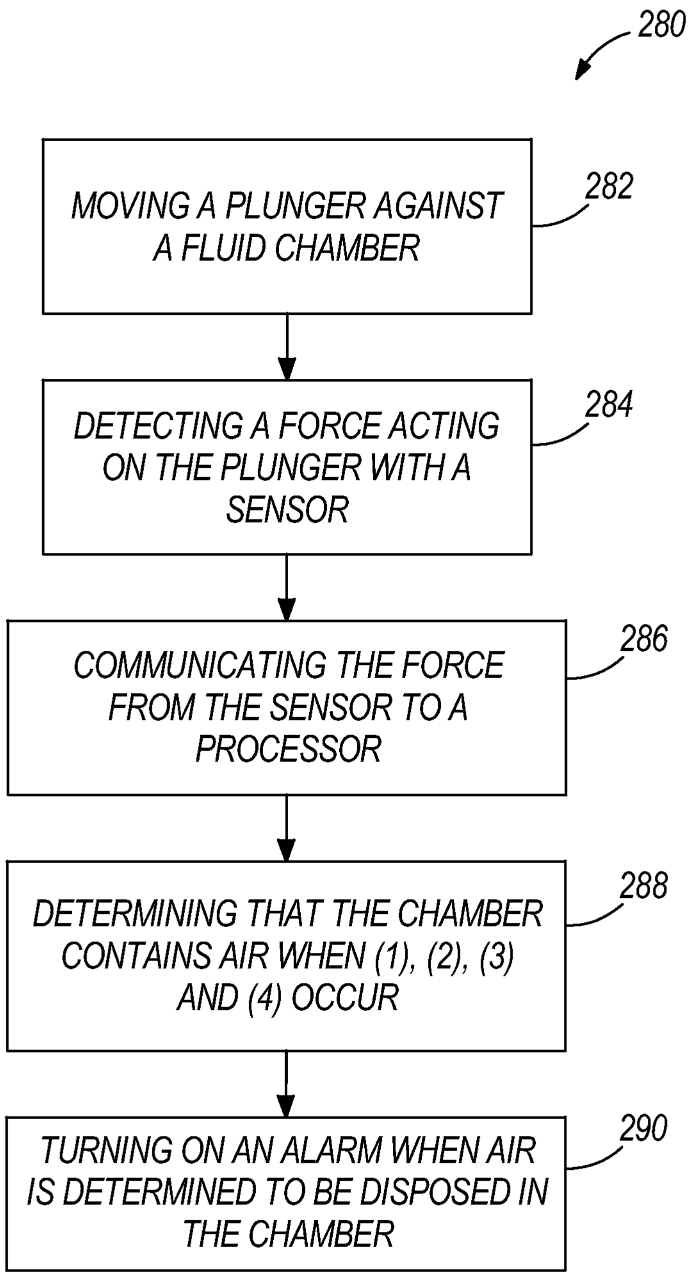
FIG. 23 illustrates a flowchart for one embodiment of a method for detecting air in a chamber of an infusion system.

FIG. 23 illustrates a flowchart for one embodiment of a method 280 for detecting air in a chamber of an infusion system. The method 280 may be implemented using the drug delivery infusion system 100 of FIG. 1 with the plunger being moved with the actuator device against the chamber containing fluid, the sensor detecting a force acting on the plunger as it moves against the chamber, the processor processing the force measurements taken by the sensor and implementing programming code stored in a non-transient memory in order to determine whether air is contained in the chamber using the algorithm set forth in method 280, and the alarm being turned on if the processor determines that air is contained in the chamber which may trigger the pump being shut down. Moreover, the method 280 may utilize the clock of the drug delivery infusion system 100 of FIG. 1 to keep time of activities of the plunger or the sensor, and may use the positional sensor to determine a position of the plunger, with each being in electronic communication with the processor. In other embodiments, the method 280 may utilize varying components to implement the method.

In step 282 a plunger is moved, with an actuator device, acting against a chamber containing fluid. In step 284, a sensor is used to detect a force acting on the plunger as it moves against the chamber. In step 286 a measurement of the force is electronically communicated from the sensor to a processor. In step 288 the processor determines: (1) a baseline force profile; (2) a current force profile representing the current force acting on the plunger against the chamber; (3) a difference between the current force profile and the baseline force profile; and (4) that the chamber contains air when the calculated difference crosses a threshold. In step 290 the processor turns on an alarm when the processor determines that the chamber contains the air. Step 290 may further comprise shutting down the pump when the alarm is turned on.

In one embodiment, the baseline force profile represents the chamber being filled with the fluid. In another embodiment, the processor determines the baseline force profile by taking force measurements at a plurality of plunger positions over a cycle of the plunger against the chamber. In an additional embodiment, the processor determines the baseline force profile by averaging force measurements taken over a plurality of cycles of the plunger against the chamber. In yet another embodiment, the processor determines the baseline force by additionally taking into account the current force profile acting on the plunger during a current cycle of the plunger against the chamber.

In still another embodiment, the processor further applies a forgetting rate, moving average or Kalman filter which controls what portion of the updated baseline force profile is made up of the average or estimated baseline force measurements and what portion of the updated baseline force profile is made up of the current force profile. In an additional embodiment, the processor determines the current force profile by taking force measurements at a plurality of plunger positions over a current cycle of the plunger against the chamber. In another embodiment, the processor calculates the difference between the current force profile and the baseline force profile by calculating respective differences between a plurality of points of the current force profile relative to a respective plurality of points of the baseline force profile, and determining a minimum difference of the respective differences or an absolute maximum difference of the respective differences. In an additional embodiment, the processor determines that the chamber contains the air when the minimum difference is less than the threshold. In still another embodiment, the processor determines that the chamber contains the air when the calculated difference is below the threshold. In other embodiments, any of the steps of the method 280 may be altered, not followed, or additional steps may be added.

Figure 24:
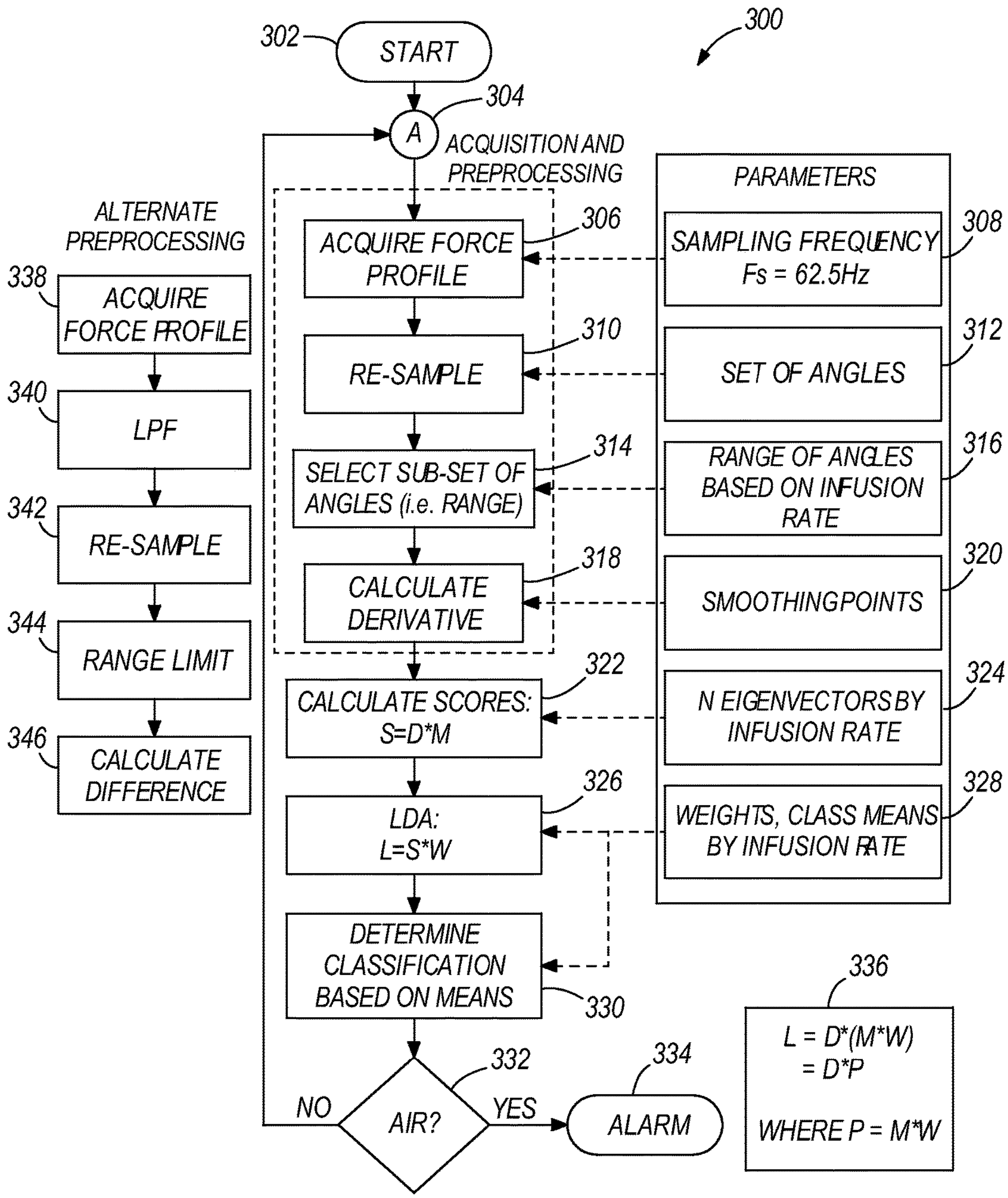
FIG. 24 illustrates one embodiment of a method, comprising a continuous flow chart, for determining whether air is contained in a chamber of a pump based upon a shape of the plunger force profile.

FIG. 24 illustrates one embodiment of a method 300, comprising a continuous flow chart, under the disclosure for determining whether air is contained in a chamber of a pump based upon a shape of the plunger force profile. The method 300 may be implemented using the drug delivery infusion system 100 of FIG. 1 with the plunger being moved with the actuator device against the chamber containing fluid, the sensor detecting a force acting on the plunger as it moves against the chamber, the processor processing the force measurements taken by the sensor and implementing programming code stored in a non-transient memory in order to determine whether air is contained in the chamber using the algorithm set forth in method 300, and the alarm being turned on if the processor determines that air is contained in the chamber which may trigger the pump being shut down. Moreover, the method 300 may utilize the clock of the drug delivery infusion system 100 of FIG. 1 to keep time of activities of the plunger or the sensor, and may use the positional sensor to determine a position of the plunger. In other embodiments, the method 300 may utilize varying components to implement the method.

In step 302, the method 300 starts. After step 302, the method proceeds through location step 304 to step 306. In step 306 a force profile over one cycle of a plunger of the chamber is acquired using the sensor. In one embodiment, as shown in box 308, the sampling frequency may be 62.5 Hz. In other embodiments, varying parameters may be used. After step 306, the method proceeds to step 310 and re-samples the force profile for the cycle of the plunger at uniform increments with respect to position or at specific positions. In one embodiment, as shown in box 312, the re-sampling may take place over a set of angles and may be performed using linear, quadratic or cubic interpolation. In other embodiments, varying parameters may be used. After step 310, the method proceeds to step 314 and selects a sub-set of angles (i.e. one or more ranges). In one embodiment, as shown in box 316, the sub-set of angles may comprise a range of angles based on the infusion rate. In other embodiments, varying parameters may be used. After step 314, the method proceeds to step 318 and calculates a derivative. In one embodiment, as shown in box 320, this step may comprise simultaneously applying a smoothing operation. In other embodiments, this step may comprise applying varying parameters. Steps 306 through 318 comprise acquisition and preprocessing steps.

After step 318, the method proceeds to step 322 and calculates scores using the equation S=D*M where D comprises the derivative and M comprises a set of N eigenvectors by infusion rate, as shown in box 324, calculated using principal component analysis. In one embodiment, N=8. In other embodiments, the scores may be calculated using varying parameters. After step 322, the method proceeds to step 326 and applies a linear determinate analysis to calculate L=S*W where L represents the linear determinate result, S represents the scores, and W, as shown in box 328, represents weights of the linear discriminate analysis. In one embodiment, as shown in box 328, this step may also consider class means by infusion rate. In other embodiments, varying parameters may be used. After step 326, the method proceeds to step 330 and determines a classification based on the result of the linear discriminate analysis. This step may also consider class means by infusion rate as shown in box 328. After step 330, the method proceeds to step 332 and determines whether air is in the chamber based on the classification. If step 332 determines that air is contained in the chamber then the method proceeds to step 334 and sounds an air alarm during which the pump may be shut down. If step 332 determines that air is not in the chamber based on the classification then the method proceeds back to location step 304.

In an alternative embodiment, instead of steps 322 and steps 326 a linear determinate analysis may be conducted, as shown in box 336, using the equation L=D*(M*W)−D*P wherein P=M*W and the variables are identical to those described above. In another alternative embodiment, instead of steps 306 through steps 318, preprocessing steps 338, 340, 342, 344, and 346 may be followed. In step 338, a force profile of the plunger over one cycle of a plunger of the chamber is acquired using the sensor. In one embodiment, as shown in box 308, the sampling frequency may be 62.5 Hz. In other embodiments, varying parameters may be used. In step 340, a low pass filter is applied. In step 342, a re-sampling is done. In one embodiment, as shown in box 312, the re-sampling may take place over a set of angles. In other embodiments, varying parameters may be used. In step 344, a range limit is applied. In one embodiment, as shown in box 316, a sub-set of angles comprising a range of angles based on the infusion rate. In other embodiments, varying parameters may be used. In step 346, a difference is calculated. In one embodiment, this difference may comprise determining differences in points of the force profile. In other embodiments, this difference may use varying parameters.

Figure 25:
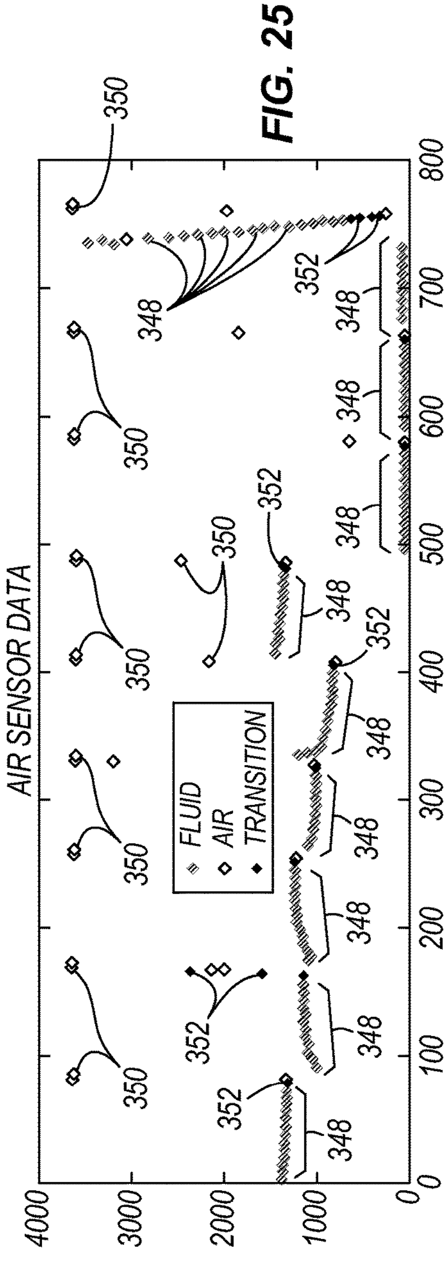
FIG. 25 illustrates a graph plotting air sensor data comprising representative points for each of fluid, air, and a transition.

FIG. 25 illustrates a graph plotting air sensor data comprising representative points for each of fluid 348, air 350, and transition 352. The Y axis represents an ADC count of the fluid of the chamber measured by a sensor and the X-axis represents sample number. The graph provides the observed air sensor ADC readings versus sample number over 1 O aggregated runs. Each run ends with a transition from fluid to air. The fluid readings (hashed symbols) 348, are clearly differentiated from those associated with air (open symbols) 350. Points that are close to or on a transition region from air to fluid are marked by solid symbols 352.

Figure 26:
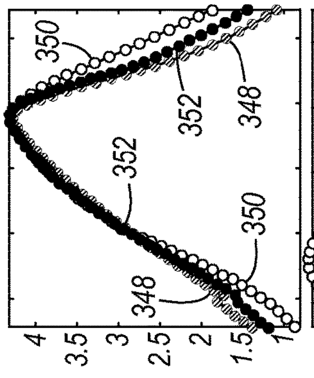
FIG. 26 illustrates a graph plotting average force profiles on the plunger corresponding to the embodiment of FIG. 28 for each of fluid, air, and a transition.

FIG. 26 illustrates a graph plotting force average profiles on the plunger corresponding to the embodiment of FIG. 25 for each of fluid 348, air 350, and transition 352. The graph demonstrates systematic differences in the average force associated with the three states (fluid 348, air 350, and transition 352) of FIG. 25. The Y-axis represents force and the X-axis represents an angular position of the motor powering the plunger.

Figure 27:
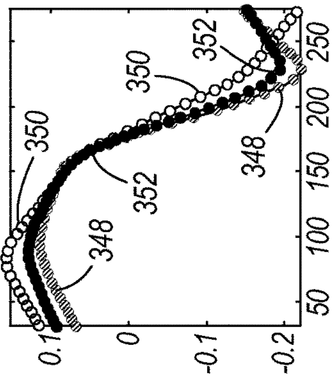
FIG. 27 illustrates a graph plotting derivatives of the force profiles on the plunger corresponding to the embodiment of FIGS. 26 and 28 for each of fluid, air, and a transition.
Figure 28:
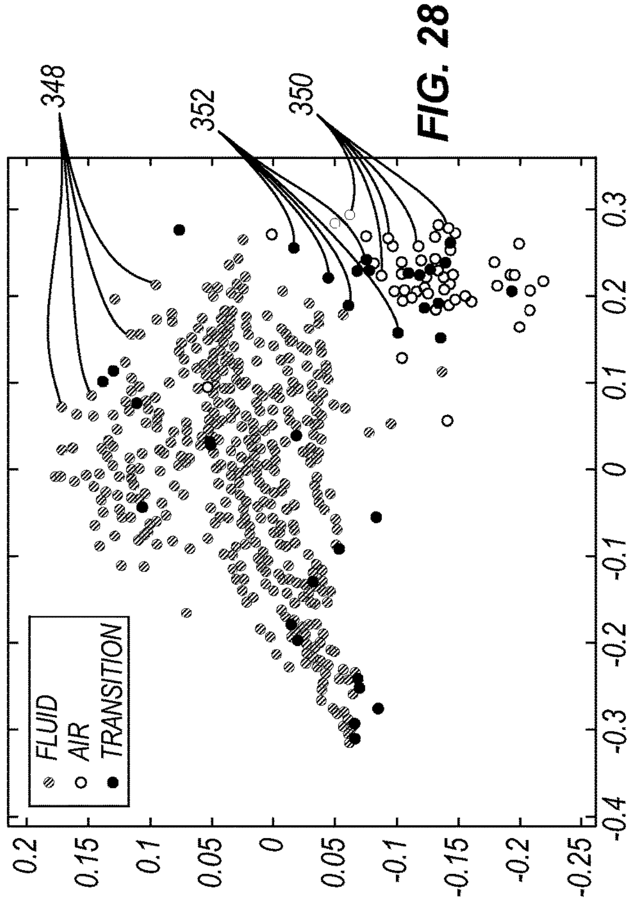
FIG. 28 illustrates a graph applying a principal component analysis plotting representative points at an infusion rate of 2 milliliters per hour.

FIG. 27 illustrates a graph plotting derivatives of the force profiles on the plunger corresponding to the embodiment of FIGS. 26 and 28 for each of fluid 348, air 350, and transition 352. The Y-axis represents a derivative of the force and the X-axis represents an angular position of the motor powering the plunger. The graph demonstrates that the systematic differences between the three states of FIG. 28 can be enhanced and differentiated from mechanism specific variation through the application of the first derivative.

FIG. 28 illustrates a graph applying a principal component analysis to plot representative points at an infusion rate of 2 milliliters per hour, with hashed symbols representing fluid points 348, open symbols representing points associated with air 350, and solid points representing transitional (indeterminant) points 352. The Y-axis represents score 4 and the X-axis represents score 2. The two dimensional view provided in the plot demonstrates a good separation across multiple actuators, fluids, and sets.

Figure 29:
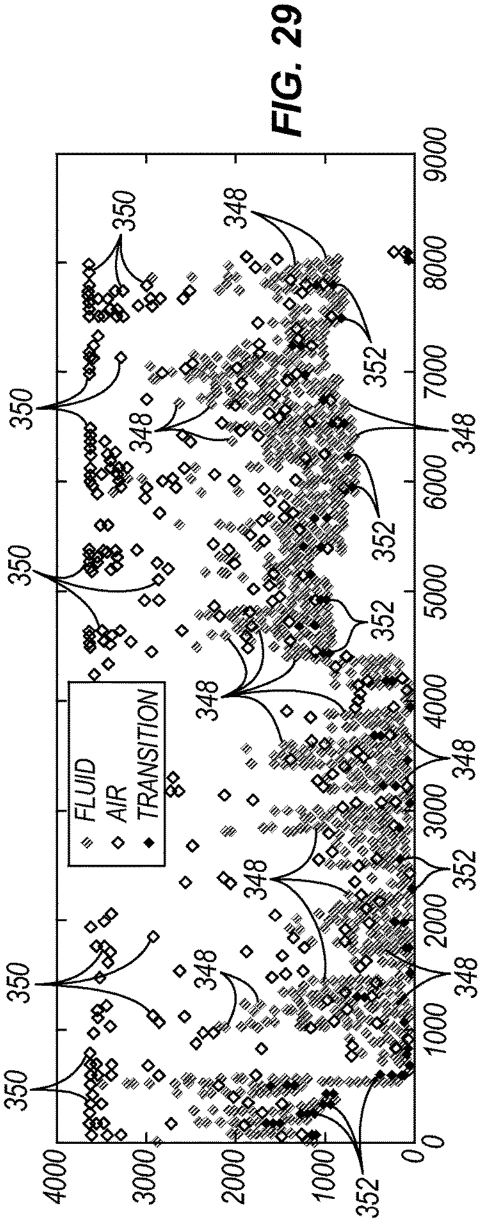
FIG. 29 illustrates a graph plotting air sensor data comprising representative points for each of fluid, air, and a transition.

FIG. 29 illustrates a graph plotting air sensor data comprising representative points for each of fluid 348, air 350, and transition 352. The Y axis represents an ADC count of the fluid of the chamber measured by a sensor and the X-axis represents sample number. The graph provides the observed air sensor ADC readings versus sample number over 10 aggregated runs. Each run ends with a transition from fluid to air. The fluid readings (hashed symbols) 348, are clearly differentiated from those associated with air (open symbols)

350. Points that are close to or on a transition region from air to fluid are marked by solid symbols 352.

Figure 30:
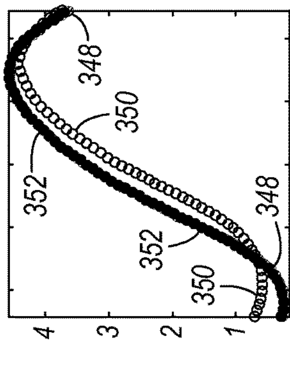
FIG. 30 illustrates a graph plotting average force profiles on the plunger corresponding to the embodiment of FIG. 32 for each of fluid, air, and a transition.
Figure 32:
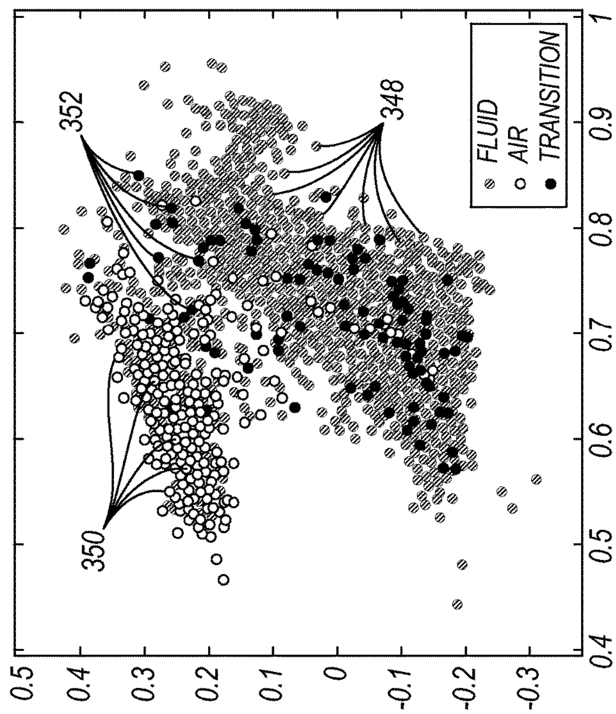
FIG. 32 illustrates a graph applying a principal component analysis plotting representative points at an infusion rate of 1,000 milliliters per hour.

FIG. 30 illustrates a graph plotting force average profiles on the plunger corresponding to the embodiment of FIG. 32 for each of fluid 348, air 350, and transition 352. The graph demonstrates systematic differences in the average force associated with the three states (fluid 348, air 350, and transition 352) of FIG. 29. The Y-axis represents force and the X-axis represents an angular position of the motor powering the plunger.

Figure 31:
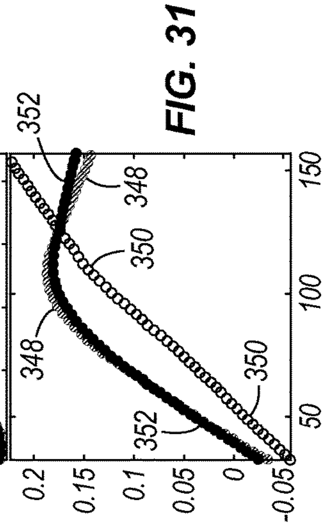
FIG. 31 illustrates a graph plotting derivatives of the force profiles on the plunger corresponding to the embodiment of FIGS. 30 and 32 for each of fluid, air, and a transition.

FIG. 31 illustrates a graph plotting derivatives of the force profiles on the plunger corresponding to the embodiment of FIGS. 30 and 32 for each of fluid 348, air 350, and transition 352. The Y-axis represents a derivative of the force and the X-axis represents an angular position of the motor powering the plunger. The graph demonstrates that the systematic differences between the three states of FIG. 32 can be enhanced and differentiated from mechanism specific variation through the application of the first derivative.

FIG. 32 illustrates a graph applying a principal component analysis to plot representative points at an infusion rate of 1,000 milliliters per hour, with hashed symbols representing fluid points 348, open symbols representing points associated with air 350, and solid points representing transitional (indeterminant) points 352. The Y-axis represents score 4 and the X-axis represents score 2. The two dimensional view provided in the plot demonstrates a good separation across multiple actuators, fluids, and sets.

Figure 33:
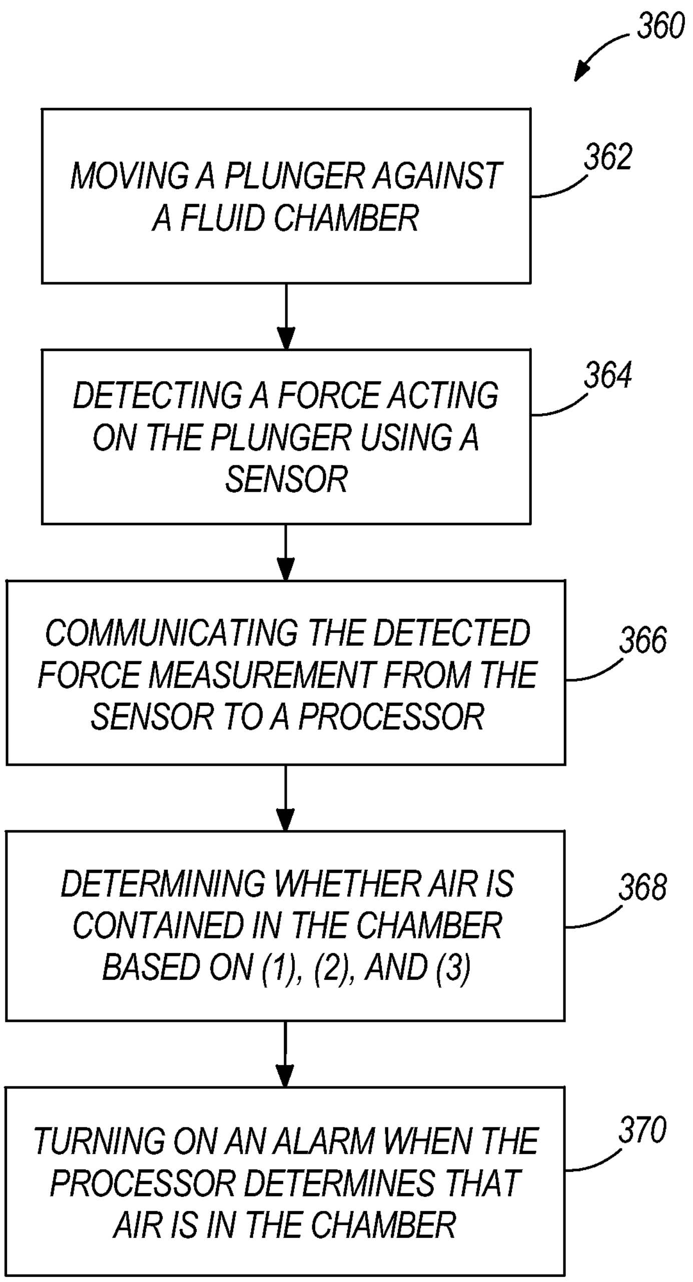
FIG. 33 illustrates a flowchart for one embodiment of a method for detecting air in a chamber of an infusion system.

FIG. 33 illustrates a flowchart for one embodiment of a method 360 for detecting air in a chamber of an infusion system. The method 360 may be implemented using the drug delivery infusion system 100 of FIG. 1 with the plunger being moved with the actuator device against the chamber containing fluid, the sensor detecting a force acting on the plunger as it moves against the chamber, the processor processing the force measurements taken by the sensor and implementing programming code stored in a non-transient memory in order to determine whether air is contained in the chamber using the algorithm set forth in method 360, and the alarm being turned on if the processor determines that air is contained in the chamber which may trigger the pump being shut down. Moreover, the method 360 may utilize the clock of the drug delivery infusion system 100 of FIG. 1 to keep time of activities of the plunger or the sensor, and may use the positional sensor to determine a position of the plunger, with each being in electronic communication with the processor. In other embodiments, the method 360 may utilize varying components to implement the method.

In step 362 a plunger is moved, with an actuator device, against a chamber containing fluid. In step 364 a sensor is used to detect a force acting on the plunger as it moves against the chamber. In step 366 a measurement of the force is electronically communicated from the sensor to a processor. In step 368 the processor: (1) preprocesses a force profile detected by the sensor; (2) extracts features from the force profile; and (3) classifies the force profile as being an air force profile or a liquid force profile based on the extracted features of the force profile. In step 370 the processor turns on an alarm when the processor determines that the chamber contains the air. Step 370 may further comprise shutting down the pump when the alarm is turned on.

In one embodiment, the processor classifies the force profile as being the air force profile or the liquid force profile without applying signal normalization to normalize to a baseline force profile. In another embodiment, the processor further applies a signal normalization to normalize the force profile relative to a baseline force profile. In an additional embodiment, the processor preprocesses the force profile detected by the sensor by: acquiring the force profile; re-sampling the force profile for a set of angles; selecting a sub-set of angles for the force profile; and calculating a derivative of the force profile based on the force profile at the sub-set of angles. In still another embodiment, the processor preprocesses the force profile detected by the sensor by: acquiring the force profile; applying a low pass filter to the force profile; re-sampling the force profile for a set of angles; applying a range limit to the force profile; and calculating a difference of the force profile.

In another embodiment, the processor extracts the features from the force profile by at least one of calculating scores of the force profile or applying a linear discriminate analysis to the force profile. In yet another embodiment, the processor calculates the scores of the force profile by multiplying a derivative of the force profile by a set of eigenvectors, and applies the linear discriminate analysis by multiplying the scores by weights. In an additional embodiment, the processor extracts the features from the force profile using an equation L=D*(M*W)−D*M*W, wherein L=a linear discriminate analysis, D=a derivative, M=a set of eigenvectors, and W=weights. In another embodiment, the processor classifies the force profile as being the air force profile or the liquid force profile based on means of a linear discriminate analysis applied to the force profile. In other embodiments, any of the steps of the method 360 may be altered, not followed, or additional steps may be added.

In another embodiment, features of the force profile are determined preferably on the basis of force changes versus displacement or position but may also be calculated on the basis of time. The features are a characteristic of the profile that is related to the presence of air or other condition that is desired to be known. For example, features may include: the scores from an abstract factor analysis, such as principal components analysis (PCA); the peak magnitude of the force profile; the phase shift with respect to time or position of the force profile; the maximum or minimum value of the first derivative with respect to position; the correlation coefficient of the force profile with exemplary profiles representing air and fluid; the distance (e.g., Euclidean or Mahalanobis distance) between the observed profile and a set of template profiles; ratios and/or differences between one or more points or averaged regions in the force profile; the correlation between the force profile and additional sensor readings (e.g., proximal and distal pressure); variance of the force profile from the mean; and a difference of the force profile from the mean.

Additionally, the features may be viewed as a set of residuals which represent the difference between the force profile or the derivative of the force profile and the expected value. The expected value may be determined using adaptive filtering, such as Kalman filtering, or as a moving or exponentially weighted moving average. In this scheme, a set of channels are defined which represent the observed force profile at a particular position through time. One or more channels are subjected to analysis through time to detect changes in their expected level on the basis of a model, an averaged profile, and/or a problematic network. When either the residual level exceeds a pre-determined threshold or the probability of an air/fluid transition increases beyond a set level, air is indicated in the pumping chamber.

In the case of the derivative based algorithm, an alternate embodiment involves a series of channels as describe above. Each channel is separately filtered through time using a moving average, spike rejection filter and/or a lowpass filter. This provides a multiplicity of signals that vary through time. The set of signals is then subject to the derivative based algorithm in which change detection occurs using an event detection and change confirmation method, as described previously. Since each channel provides an indication of the fluid chamber status, a method is employed to combine the indicators and provide one final indicator. The preferred method is to always utilize the channel that provides the reading that is most associated with air. For example, this may comprise the channel that experienced the high derivative and greatest change through time. Alternately, aggregation of the signals can occur using a voting algorithm, fuzzy logic, decision trees, support vector machines or Bayesian networks.

In another embodiment, the multiple channels described above may be subjected to an N-th order Kalman filter and used to generate a residual from an expected value. A change is detected when the residual exceeds a pre-set threshold. In other embodiments, other methods may be utilized.

Figure 34:
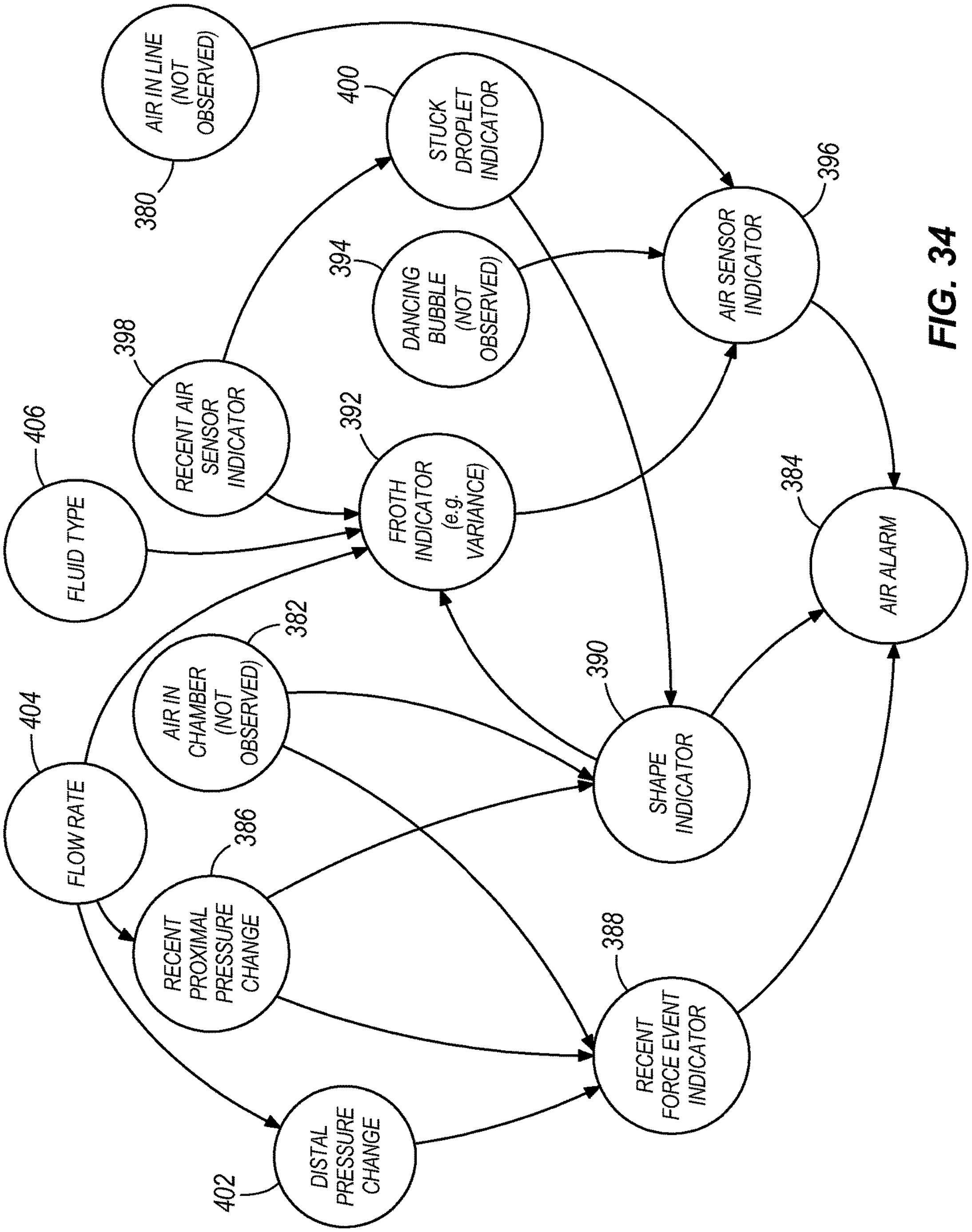
FIG. 34 illustrates a flowchart of a Bayesian network showing a combination of algorithm sensors and a priori information which may be used to produce an indication of air-in-line or air in a chamber.

FIG. 34 illustrates a flowchart of a Bayesian network showing a combination of algorithm sensors and a priori information which may be used to produce an indication of air-in-line or air in a chamber. For instance, any of the following air devices, tests, or algorithms may be utilized individually or collectively in different numbers or weights to identify air-in-line 380 or air in the chamber 382 to sound an air alarm 384: a recent proximal pressure change 386; a recent force event indicator 388; a shape indicator 390; a froth indicator (e.g. variance) 392; a dancing bubble indicator 394; an air sensor indicator 396; a recent air sensor indicator 398; a stuck droplet indicator 400; a distal pressure change 402; a flow rate 404; or a fluid type 406. In conjunction with these different tests, the following patents and patent applications are hereby incorporated by reference in full: U.S. Pat. No. 7,981,082; U.S. Ser. No. 61/460,766; and U.S. Ser. No. 61/525,587. The systems, methods, and algorithms/tests of any of the listed incorporated by reference patents may be utilized in conjunction with the systems, methods, and algorithms/tests of the instant disclosure. For example, the air indicator or air alarm as described herein may be used to qualify alarms from other sensors and thereby reduce the probability of nuisance alarms.

One or more systems/methods of the disclosure more accurately detects air in the line of an infusion device than many current systems and methods. The systems/methods of the disclosure may be combined with existing systems/methods for detecting air in an infusion system to improve the reliability of air detection systems. The disclosure allows for the combination of the output of a force sensor signal with one or more air sensors to improve the reliability of existing air detection systems/methods. In doing so, the disclosed system/method does not require additional hardware modifications but instead leverages the acquired force signal. Additionally, the disclosure does not necessarily require the replacement of existing software modules for air detection but adds an additional safety layer to improve the robustness of existing air detection systems and methods.

It should be understood, of course, that the foregoing relates to exemplary embodiments of the disclosure and that modifications may be made without departing from the scope of the disclosure as set forth in the following claims.

What is claimed is:

1. A system for detecting air in a chamber of an infusion system, the infusion system comprising a pump and a plunger moveably disposed against the chamber, the chamber configured to hold fluid, the system comprising:
- an actuator device configured to move the plunger against the chamber;
- a sensor configured to detect a force acting on the plunger as it moves against the chamber; and
- one or more hardware processors configured to:
  - determine a change in force per unit volume of the fluid at a first time during infusion;
  - determine the change in force per unit volume satisfies a threshold at the first time;
  - determine a difference between a first average force acting on the plunger prior to the first time and a second average force acting on the plunger after a delay time from the first time;
  - determine the difference satisfies a force differential; and
  - detect a presence of air in the chamber based on the determination of the difference satisfying the force differential and the determination of the change in force satisfying the threshold.

2. The system of claim 1, wherein the determination of the change in force per unit volume satisfying the threshold further comprises determining the change in force per unit volume crosses the threshold more than once in a time period after the first time, wherein the time period is less than or equal to the delay time.

3. The system of claim 1, wherein the change in force per unit volume comprises a change in derivative of force with respect to per unit volume.

4. The system of claim 1, wherein the delay time is measured with respect to volume of fluid delivered.

5. A system for detecting air in a chamber of an infusion system, the infusion system comprising a pump and a plunger moveably disposed against the chamber, the chamber configured to hold fluid, the system comprising one or more hardware processors configured to:
- receive a measurement of force acting on the plunger as it moves against the chamber;
- determine a change in force per unit volume of the fluid at a first time during infusion;
- determine the change in force per unit volume satisfies a threshold at the first time;
- determine a difference between a first average force acting on the plunger prior to the first time and a second average force acting on the plunger after a delay time from the first time;
- determine the difference satisfies a force differential; and
- detect a presence of air in the chamber based on the determination of the difference satisfying the force differential and the determination of the change in force satisfying the threshold.

6. The system of claim 5, wherein the determination of the change in force per unit volume satisfying the threshold further comprises determining the change in force per unit volume crosses the threshold more than once in a time period after the first time, wherein the time period is less than or equal to the delay time.

7. The system of claim 5, wherein the change in force per unit volume comprises a change in derivative of force with respect to per unit volume.

8. The system of claim 5, wherein the delay time is measured with respect to volume of fluid delivered.

9. A method for detecting air in a chamber of an infusion system, the infusion system comprising a pump and a plunger moveably disposed against the chamber, the chamber configured to hold fluid, the method comprising:
- receiving a measurement of force acting on the plunger as it moves against the chamber;

determining a change in force per unit volume of the fluid at a first time during infusion;

determining the change in force per unit volume satisfies a threshold at the first time;

determining a difference between a first average force acting on the plunger prior to the first time and a second average force acting on the plunger after a delay time from the first time;

determining the difference satisfies a force differential; and detecting a presence of air in the chamber based on the determination of the difference satisfying the force differential and the determination of the change in force satisfying the threshold.

10. The method of claim 9, wherein the determination of the change in force per unit volume satisfying the threshold further comprises determining the change in force per unit volume crosses the threshold more than once in a time period after the first time, wherein the time period is less than or equal to the delay time.

11. The method of claim 9, wherein the change in force per unit volume comprises a change in derivative of force with respect to per unit volume.

12. The method of claim 9, wherein the delay time is measured with respect to volume of fluid delivered.

13. The method of claim 9, further comprising determining a force profile of the plunger and detecting the presence of air based on a change in a shape of the force profile.

14. The method of claim 13, further comprising classifying the force profile based on a linear discriminate analysis.

15. The method of claim 13, further comprising normalizing the determined force profile.

16. The method of claim 13, wherein the force profile comprises a vector corresponding to varying number of positions of the plunger.

* * * * *